US010583111B2

(12) United States Patent
Zhang et al.

(10) Patent No.: US 10,583,111 B2
(45) Date of Patent: Mar. 10, 2020

(54) METHOD FOR PREVENTING OR TREATING DISEASES ASSOCIATED WITH THE INHIBITION OF EGFR

(71) Applicant: ONQUALITY PHARMACEUTICALS CHINA LTD., Shanghai (CN)

(72) Inventors: Shiyi Zhang, Shanghai (CN); Zhaoyu Wu, Shanghai (CN); Chao Liu, Shanghai (CN); Leying Chen, Shanghai (CN); Xin Zhao, Shanghai (CN); Zhehui Gong, Shanghai (CN); Rui Xing, Shanghai (CN); Songxuan Sun, Shanghai (CN); Jie Luo, Shanghai (CN)

(73) Assignee: ONQUALITY PHARMACEUTICALS CHINA LTD., Shanghai (CN)

( * ) Notice: Subject to any disclaimer, the term of this patent is extended or adjusted under 35 U.S.C. 154(b) by 0 days.

(21) Appl. No.: 16/424,382

(22) Filed: May 28, 2019

(65) Prior Publication Data
US 2019/0282536 A1  Sep. 19, 2019

Related U.S. Application Data

(63) Continuation of application No. PCT/CN2018/120343, filed on Dec. 11, 2018.

(30) Foreign Application Priority Data

Dec. 13, 2017 (CN) .......................... 2017 1 1328090

(51) Int. Cl.
| | | |
|---|---|---|
| A61K 31/5375 | (2006.01) | |
| A61K 31/517 | (2006.01) | |
| A61K 31/435 | (2006.01) | |
| A61K 31/34 | (2006.01) | |
| A61K 39/395 | (2006.01) | |
| A61P 17/00 | (2006.01) | |
| A61K 9/06 | (2006.01) | |
| A61K 9/00 | (2006.01) | |

(52) U.S. Cl.
CPC ............ *A61K 31/34* (2013.01); *A61K 9/0014* (2013.01); *A61K 9/06* (2013.01); *A61P 17/00* (2018.01)

(58) Field of Classification Search
CPC .............. A61K 31/5375; A61K 31/517; A61K 31/435; A61K 39/395
USPC ......... 514/231.5, 259.5, 267, 466; 424/143.1
See application file for complete search history.

(56) References Cited

U.S. PATENT DOCUMENTS

| | | |
|---|---|---|
| 4,322,433 A | 3/1982 | Leslie et al. |
| 4,450,175 A | 5/1984 | Warshaw |
| 4,654,209 A | 3/1987 | Leslie et al. |
| 5,504,117 A | 4/1996 | Gorfine |
| 6,492,398 B1 | 12/2002 | Vyas |
| 6,620,818 B1 | 9/2003 | Davis |
| 6,780,849 B2 | 8/2004 | Herrmann et al. |
| 6,979,688 B2 | 12/2005 | Ford |
| 6,987,129 B2 | 1/2006 | Mak et al. |
| 7,402,557 B2 | 7/2008 | Miller et al. |
| 7,696,247 B2 | 4/2010 | Herrmann et al. |
| 8,729,056 B2 | 5/2014 | Ishizaka et al. |
| 8,784,408 B2 | 7/2014 | DeLand et al. |
| 8,795,263 B2 | 8/2014 | DeLand et al. |
| 9,271,956 B2 | 3/2016 | Auclair |
| 9,427,605 B2 | 8/2016 | Peters |
| 9,428,582 B2 | 8/2016 | Edvardsen et al. |
| 9,480,707 B2 | 11/2016 | Perricone |
| 9,700,579 B2 | 7/2017 | Ehrlich et al. |
| 2002/0049188 A1 | 4/2002 | Azarnoff et al. |
| 2003/0157037 A1 | 8/2003 | Bunger et al. |
| 2003/0203915 A1 | 10/2003 | Fang et al. |
| 2006/0030622 A1 | 2/2006 | Mak et al. |
| 2007/0172847 A1 | 7/2007 | Bonavida et al. |
| 2008/0045909 A1 | 2/2008 | Fossel |
| 2009/0048219 A1 | 2/2009 | Garvey |
| 2009/0203050 A1 | 8/2009 | Bonavida et al. |
| 2010/0016446 A1 | 1/2010 | Gonda et al. |
| 2011/0077260 A1 | 3/2011 | Ford |
| 2011/0190244 A1 | 8/2011 | Zalcberg |
| 2011/0196353 A1 | 8/2011 | DeLand et al. |
| 2013/0225690 A1 | 8/2013 | Perez-Soler et al. |
| 2014/0011820 A1 | 1/2014 | Rodemer |
| 2014/0336268 A1 | 11/2014 | Salentine et al. |
| 2015/0313901 A1 | 11/2015 | Ford |
| 2015/0335597 A1 | 11/2015 | Pui et al. |

(Continued)

FOREIGN PATENT DOCUMENTS

| | | |
|---|---|---|
| CN | 1568943 A | 1/2005 |
| CN | 103446261 B | 4/2015 |

(Continued)

OTHER PUBLICATIONS

Arriola, E. et al., Management of the adverse events of afatinib: a consensus of the recommendations of the Spanish expert panel, Future Oncol., 11(2): 267-277 (2015).
Aw, D. C-W. et al., Management of epidermal growth factor receptor tyrosine kinase inhibitor-related cutaneous and gastrointestinal toxicities, Asia-Pac J Clin Oncol., 14: 23-31. (2018).
BIDIL® (isosorbide dinitrate and hydralazine hydrochloride), Highlights of Prescribing Information, 11 pages (Revised Mar. 2019).
Califano, R. et al., Expert Consensus on the Management of Adverse Events from EGFR Tyrosine Kinase Inhibitors in the UK, Drugs, 75: 1335-1348 (2015).

(Continued)

*Primary Examiner* — Raymond J Henley, III
(74) *Attorney, Agent, or Firm* — Choate, Hall & Stewart LLP; Brenda Herschbach Jarrell; Xiaodong Li

(57) ABSTRACT

The present application provides a use of a nitric oxide releasing agent in preparing a medicament, wherein the medicament is used for preventing or treating EGFR inhibition associated epithelial diseases in a subject. The present application further provides a pharmaceutical composition or a kit comprising EGFR inhibitor and nitric oxide releasing agent.

22 Claims, 13 Drawing Sheets

(56) References Cited

U.S. PATENT DOCUMENTS

| | | |
|---|---|---|
| 2016/0039852 A1 | 2/2016 | Russell et al. |
| 2016/0101114 A1 | 4/2016 | Lacouture et al. |
| 2016/0151427 A1 | 6/2016 | Whitlock et al. |
| 2017/0216441 A1 | 8/2017 | Muni |
| 2017/0354649 A1 | 12/2017 | Wang et al. |

FOREIGN PATENT DOCUMENTS

| | | |
|---|---|---|
| CN | 105381070 A | 3/2016 |
| CN | 107158287 A | 9/2017 |
| CN | 107412455 A | 12/2017 |
| CN | 107617010 A | 1/2018 |
| EP | 2251688 A1 | 11/2010 |
| EP | 2368549 A1 | 9/2011 |
| WO | WO-95/32715 A1 | 12/1995 |
| WO | WO-96/27372 A1 | 9/1996 |
| WO | WO-99/38506 A2 | 8/1999 |
| WO | WO-00/10559 A1 | 3/2000 |
| WO | WO-00/52013 A2 | 9/2000 |
| WO | WO-01/89572 A1 | 11/2001 |
| WO | WO-02/13982 A1 | 2/2002 |
| WO | WO-2006/100154 A1 | 9/2006 |
| WO | WO-2006/113479 A2 | 10/2006 |
| WO | WO-2009/114745 A1 | 9/2009 |
| WO | WO-2010/011650 A1 | 1/2010 |
| WO | WO-2010/125143 A1 | 11/2010 |
| WO | WO-2010/148572 A1 | 12/2010 |
| WO | WO-2011/000218 A1 | 1/2011 |
| WO | WO-2011/022652 A1 | 2/2011 |
| WO | WO-2011/022680 A2 | 2/2011 |
| WO | WO-2011/047256 A1 | 4/2011 |
| WO | WO-2012/082976 A1 | 6/2012 |
| WO | WO-2012/153331 A2 | 11/2012 |
| WO | WO-2013/009535 A1 | 1/2013 |
| WO | WO-2013/029009 A1 | 2/2013 |
| WO | WO-2013/083695 A1 | 6/2013 |
| WO | WO-2013/085784 A1 | 6/2013 |
| WO | WO-2013/138075 A1 | 9/2013 |
| WO | WO-2013/157891 A1 | 10/2013 |
| WO | WO-2014/047140 A1 | 3/2014 |
| WO | WO-2014/134502 A1 | 9/2014 |
| WO | WO-2015/095640 A1 | 6/2015 |
| WO | WO-2015/182905 A1 | 12/2015 |
| WO | WO-2015/197524 A1 | 12/2015 |
| WO | WO-2016/022170 A1 | 2/2016 |
| WO | WO-2016/210230 A1 | 12/2016 |
| WO | WO-2017/029647 A1 | 2/2017 |
| WO | WO-2017/154001 A1 | 9/2017 |
| WO | WO-2017/165440 A1 | 9/2017 |
| WO | WO-2017/223182 A1 | 12/2017 |

OTHER PUBLICATIONS

Chu, C-Y. et al., Taiwanese Dermatological Association consensus for the prevention and management of epidermal growth factor receptor tyrosine kinase inhibitor-related skin toxicities, Journal of the Formosan Medical Association, 116: 413-423 (2017).

dilatrate® -SR (isosorbide dinitrate), Drug Summary, 8 pages (Revised Oct. 2014).

Hirsh, V., Managing treatment-related adverse events associated with EGFR tyrosine kinase inhibitors in advanced non-small-cell lung cancer, Current Oncology, 18(3): 126-138 (2011).

Isordil® Titradose™ (isosorbide dinitrate), Drug Summary, 8 pages (Revised Jan. 2015).

Kozuki, T., Skin problems and EGFR-tyrosine kinase inhibitor, Japanese Journal of Clinical Oncology, 46(4): 291-298 (2016).

Lacouture, M.E. et al., Clinical practice guidelines for the prevention and treatment of EGFR inhibitor-associated dermatologic toxicities, Support Care Cancer, 19: 1079-1095 (2011).

NITRO-BID, Savage Laboratories, Drug Summary, 2 pages (Revised Sep. 2011).

RECTIV ® (nitroglycerin), Highlights of Prescribing Information, 4 pages (Revised Nov. 2016).

Thatcher, N. et al., Expert Consensus on the Management of Erlotinib-Associated Cutaneous Toxicity in the U.K., The Oncologist, 14: 840-847 (2009).

Zhang, Y-h. and Peng, S-x. Advances in the study of nitric oxide-donating drugs, Acta Pharmaceutica Sinica, 44(11): 1200-1210 (2009). English Abstract.

METHOD FOR PREVENTING OR TREATING DISEASES ASSOCIATED WITH THE INHIBITION OF EGFR

INVENTION FIELD

The present application relates to a method of preventing or treating EGFR-inhibition associated diseases.

BACKGROUND

Mutation or overexpression of epidermal growth factor receptor (EGFR) has been found to be associated with a variety of cancers, and patients suffering from such tumours can be treated by EGFR-inhibiting therapy (e.g., administering EGFR inhibitor). However, this type of therapy will cause severe side effects (especially, in skin, facial organs, and gastrointestinal tract). It has been reported that skin side effects occur in greater than 50% of patients treated with EGFR inhibitors (e.g., see Heidary et al., Journal of the American Academy of Dermatology, 58 (4): 545, 2008). Various side effects of EGFR-inhibiting therapy can result in medicament withdrawal or dose reduction, and can compromise the patient's life quality.

There is no successful therapeutic regimen in the art controlling the side effects caused by EGFR-inhibiting therapy. Thus, there is an urgent need for therapeutic regimens capable of controlling these side effects successfully.

SUMMARY OF THE INVENTION

The present application relates to a method or use of preventing or treating an EGFR inhibition associated disease. The present application provides a use of nitric oxide releasing agent in preparing medicament, wherein the medicament is used for preventing or treating an EGFR inhibition associated epithelial disease in a subject. The present application also provides a drug, a pharmaceutical composition or kit comprising the nitric oxide releasing agent, a method of preventing or treating a disease or disorder associated with inhibition of EGFR in a subject using the nitric oxide releasing agent, and the like. The present application has discovered that the use of a nitric oxide releasing agent can effectively prevent or treat an EGFR-inhibition associated disease or disorder.

In one aspect, the present application provides a use of nitric oxide releasing agent in preparing medicament, wherein the medicament is used for preventing or treating an EGFR-inhibition associated epithelial disease or disorder in a subject.

In some embodiments, the EGFR inhibition is caused by administration of an EGFR inhibitor.

In some embodiments, the EGFR inhibitor comprises a medicament for treating cancers.

In some embodiments, the EGFR inhibitor acts directly on an EGFR protein and/or nucleic acid for encoding an EGFR protein.

In some embodiments, the EGFR inhibitor comprises a small molecular EGFR inhibitor, a protein macromolecule that binds specifically to EGFR, an RNAi or antisense oligonucleotide that inhibits expression of an EGFR protein and antisense oligonucleotide that inhibits expression of an EGFR protein. In some embodiments, the small molecular EGFR inhibitor is selected from the following group: a small molecular EGFR inhibitor that binds reversibly to EGFR, a small molecular EGFR inhibitor that binds irreversibly to EGFR, and/or a small molecular EGFR inhibitor that binds specifically to mutant EGFR.

In some embodiments, the EGFR inhibitor comprises Cetuximab, Gefitinib, Erlotinib, Icotinib, Sapitinib, Afatinib, Lapatinib, Vandetanib, Neratinib, Brigatinib, Panitumumab, Necitumumab, Nimotuzumab, Tesevatinib, Allitinib, Theliatinib, Rociletinib, Canertinib, AZD3759, YZJ-0318, Neptinib, Naquotinib, PF-06747775, SPH1188-11, Poziotinib, Epitinib, Varlitinib, Alflutinib, HM61713, CK-101, Pyrotinib, Larotinib, HS-10296, AP32788, Simotinib, GMA204, Virlitinib, Yinlitinib, Nazartinib, Rociletinib, Olmutinib, Osimertinib, Dacomitinib, Avitinib and/or EAI045.

In some embodiments, the EGFR inhibitor is administered in combination with one or more other therapies.

In some embodiments, the epithelial disease is directly caused by EGFR inhibition.

In some embodiments, the epithelial disease comprises epithelial cell disease and/or endothelial cell disease.

In some embodiments, the epithelial cell comprises skin epithelial cell, oral epithelial cell, stomach epithelial cell and/or small intestine epithelial cell.

In some embodiments, the endothelial cell comprises vascular endothelial cell.

In some embodiments, the epithelial disease comprises EGFR-inhibition associated rash, EGFR-inhibition associated acne, EGFR-inhibition associated skin pruritus, EGFR-inhibition associated hand-foot syndrome, EGFR-inhibition associated alopecia, EGFR-inhibition associated hair changes, EGFR-inhibition associated erythema, EGFR-inhibition associated skin exfoliation, EGFR-inhibition associated herpes, EGFR-inhibition associated hirsutism, EGFR-inhibition associated hyperpigmentation, EGFR-inhibition associated nail disorders, EGFR-inhibition associated paronychia and schizonychia, EGFR-inhibition associated xerosis cuits, EGFR-inhibition associated hypersensitivity, EGFR-inhibition associated mucositis, EGFR-inhibition associated nasopharyngitis, EGFR-inhibition associated epistaxis, EGFR-inhibition associated xerostomia, EGFR-inhibition associated cheilitis, EGFR-inhibition associated oral ulcer and/or EGFR-inhibition associated gastrointestinal mucosal injury. In some embodiments, the epithelial disease comprises EGFR-inhibition associated rash.

In some embodiments, the severity grading of epithelial disease is Grade 1 or above, Grade 2 or above, Grade 3 or above, Grade 4 or above, or Grade 5, as evaluated in accordance with NCI-CTCAE V5.0.

In some embodiments, the nitric oxide releasing agent is capable of producing at least one of $NO^+$, $NO^-$, $N_2O$, $NO$, $N_2O_3$, $NO_2$, $NO_3^-$ and $NO_2^-$. In some embodiments, the nitric oxide releasing agent is capable of directly or indirectly producing NO.

In some embodiments, the nitric oxide releasing agent comprises NO.

In some embodiments, the nitric oxide releasing agent comprises organic molecule, inorganic molecule, polymer or nanomaterial and/or ammonia oxidizing microorganism (AOM).

In some embodiments, the nitric oxide releasing agent comprises organic molecule, wherein organic molecule comprises nitroglycerin, isosorbide mononitrate, butanediol mononitrate, pentaerythritol tetranitrate, isosorbide dinitrate, trolnitrate, nicorandil, nitro dihydroxyl methyl butanol, 5-amino-3-(4-morpholinyl)-1,2,3-oxadiazole, isoamyl nitrite, 3,3-di (aminoethyl)-1-hydroxyl-2-carbonyl-1-triazene (NOC-18), sulfo NONOate disodium salt, S-Nitrosoglutathione, S-Nitroso-N-acetylpenicillamine, 4-Phenyl-3- furoxancarbonitrile, (±)-(E)-4-Ethyl-2-[(E)-hydroxyimino]-5-nitro-3-hexenamide, Streptozocin, NG-Hydroxy-L-arginine acetate salt, $O_2$-(2,4-Dinitrophenyl) 1-[(4-ethoxycarbonyl)piperazin-1-yl]diazen-1-ium-1,2-diolate, N-nitrosodibutylamine, 3-morpholinosydnonimine (SIN-1), Linsidomine, Molsidomine, 3-(4-acetylphenyl)sydnone, Diethylamine NONOate/AM and/or Itramin.

In some embodiments, the nitric oxide releasing agent comprises organic molecule, wherein the organic molecule comprises nitroglycerin, isosorbide mononitrate and/or isosorbide dinitrate. In some embodiments, the EGFR-inhibition associated epithelial disease is an EGFR-inhibition associated rash or EGFR-inhibition associated pruritus. In some embodiments, the EGFR-inhibition associated rash or EGFR-inhibition associated pruritus is relieved by at least 10%.

In some embodiments, the nitric oxide releasing agent comprises inorganic molecule, wherein the inorganic molecule comprises nitryl complex, metal nitrosyl complex, metal nitrosamino complex, nitrate and/or nitrite. In some embodiments, the nitric oxide releasing agent comprises inorganic molecule, wherein the inorganic molecule comprises sodium nitroprusside. In some embodiments, the EGFR-inhibtion associated epithelial disease is EGFR-inhibition associated rash or EGFR-inhibition associated pruritus. In some embodiments, the rash or pruitus is relieved by at least 10%.

In some embodiments, the nitric oxide releasing agent comprises polymer or nanomaterial, wherein the polymer or nanomaterial comprises S-nitrosothiolsilica nanosphere, S-nitrosoethanedithiol chitin and/or oligo-propylenediamine grafted chitosan NONOate.

In some embodiments, the nitric oxide releasing agent comprises an ammonia oxidizing microorganism (AOM), and the ammonia oxidizing microorganism (AOM) comprises an ammonia oxidizing bacterium (AOB). In some embodiments, the nitric oxide releasing agent comprises an ammonia oxidizing microorganism (AOM), and the ammonia oxidizing microorganism (AOM) comprises *Nitrosomonas, Nitrosococcus, Nitrosospira, Nitrosocystis, Nitrosolobus*, and/or *Nitrosovibrio*.

In some embodiments, the nitric oxide releasing agent has a molecular weight less than or equal to 2000 Daltons, less than or equal to 1500 Daltons, less than or equal to 1200 Daltons, less than or equal to 1000 Daltons, less than or equal to 900 Daltons, less than or equal to 800 Daltons, less than or equal to 700 Daltons, less than or equal to 600 Daltons, less than or equal to 500 Daltons, less than or equal to 400 Daltons, less than or equal to 300 Daltons, less than or equal to 200 Daltons and/or less than or equal to 100 Daltons.

In some embodiments, the nitric oxide releasing agent comprises the following one or more groups: diazeniumdiolate, hydroxyldiazenesulfonic acid, S-nitrosothiol, furoxan, oxime, N-nitrosoamine, N-hydroxylguanidine, nitrate, nitrite, nitric ester, nitrous acid ester, sydnonimine, sydnone, oxatriazol-5-imine, oxatriazol-5-one, hydroxylamine, dioxadiazocyclobutene, N-hydroxylnitrosoamine, N-nitrosoimine, hydroxylurea and metal nitrosamino complex.

In some embodiments, the drug is prepared for topical administration. In some embodiments, the site of the topical administration is not the occurrence site of cancer or potential metastatic site of cancer.

In some embodiments, the concentration of the nitric oxide releasing agent in the drug is from about 0.0001% (w/w) to about 50% (w/w).

In some embodiments, the topical administration is transdermal administration.

In some embodiments, the medicament is prepared as an ointment.

In some embodiments, the medicament further comprises one or more other active components.

In some embodiments, the drug does not substantially affect the therapeutic effect of the EGFR inhibitor.

In some embodiments, the subject comprises a human or a non-human animal. In some embodiments, the non-human animal comprises a monkey, a chicken, a goose, a cat, a dog, a mouse, and/or a rat.

In some embodiments, the subject comprises a cancer patient. In some embodiments, the inhibition of EGFR is caused by administration of an EGFR inhibitor to the subject. In some embodiments, the cancer patient has been, is being, and/or will be administered with an EGFR inhibitor. In some embodiments, the nitric oxide releasing agent is administered before, simultaneously with, or after the subject receives the EGFR inhibitor.

In another aspect, the present application further provides a nitric oxide releasing agent for use in preventing or treating an EGFR-inhibition associated disease or disorder.

In another aspect, the present application further provides a method of preventing or treating an EGFR-inhibition associated disease or disorder in a subject, which comprises administering an effective amount of a nitric oxide releasing agent for preventing or treating to the subject.

In another aspect, the present application further provides a pharmaceutical composition or kit comprising: 1) an EGFR inhibitor; and 2) a nitric oxide releasing agent.

In some embodiments, in the pharmaceutical composition or kit, the EGFR inhibitor and the nitric oxide releasing agent are not mixed with each other.

In some embodiments, the EGFR inhibitor and the nitric oxide releasing agent are each independently present in a separate container.

In some embodiments, the nitric oxide releasing agent is prepared for transdermal administration.

In some embodiments, the nitric oxide releasing agent in the pharmaceutical composition or kit is prepared for topical administration. In some embodiments, the administration site of the topical administration is not the occurrence site of cancer or potential metastatic site of cancer.

In some embodiments, the nitric oxide releasing agent is prepared as an ointment.

In some embodiments, the concentration of the nitric oxide releasing agent is from about 0.0001% (w/w) to about 50% (w/w).

In some embodiments, the nitric oxide releasing agent in 2) of the pharmaceutical composition or kit is capable of preventing or treating a disease or disorder caused by the EGFR inhibitor in 1).

In some embodiments, the nitric oxide releasing agent in 2) of the pharmaceutical composition or kit does not substantially affect the therapeutic effect of the EGFR inhibitor in 1).

In some embodiments, the nitric oxide releasing agent in 2) of the pharmaceutical composition or kit is administered before, simultaneously with, or after the subject receives the EGFR inhibitor in 1).

Other aspects and advantages of the present application will be readily apparent to those skilled in the art from the following detailed description. Only the exemplary embodiments of the present application are shown and described in the following detailed description. As will be appreciated by those skilled in the art, the present application will be able to make modifications to the specific embodiments disclosed herein without departing from the spirit and scope of the invention. The drawings in the present specification and the description in the specification are merely illustrative and not restrictive.

BRIEF DESCRIPTION OF THE DRAWINGS

Specific features of the invention as set forth in this application are set forth in the appended claims. The features and advantages of the inventions of the present application can be better understood by referring to the exemplary embodiments and the accompanying drawings. A brief description of the drawing is as follows:

DETAILED DESCRIPTION

Figure 1:
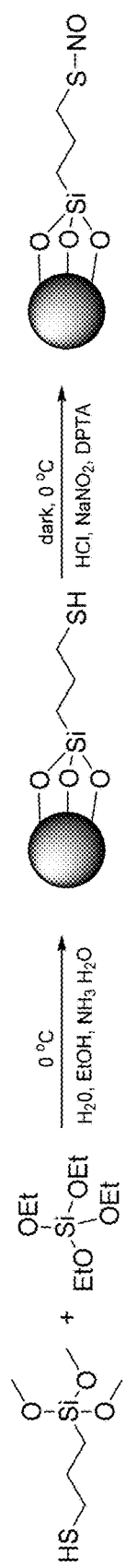
FIG. 1 depicts an exemplary synthesis route of S-nitrosothiolsilica nanosphere.
Figure 2:
FIG. 2 depicts an exemplary synthesis route of S-nitrosoethanedithiolchitin.
Figure 3:
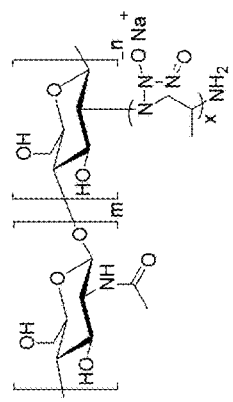
FIG. 3 depicts an exemplary synthesis route of an oligopropylenediamine grafted chitosan NONOate.
Figure 3:
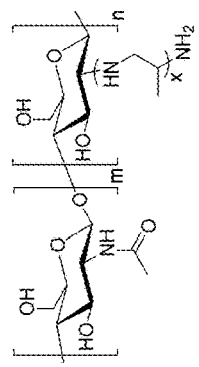
Figure 3:
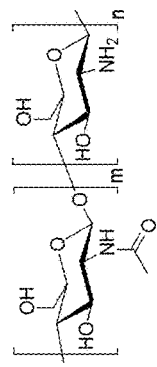

The embodiments of the present invention are described below by way of specific embodiments, and those skilled in the art can readily appreciate other advantages and effects of the present invention from the disclosure of the present specification. An aspect of the present application relates to a method of preventing or treating EGFR inhibition-associated epithelial diseases comprising administering an effective amount of a nitric oxide releasing agent to an subject in need thereof.

EGFR and EGFR Inhibition

The term "EGFR" as used herein generally refers to Epidermal Growth Factor Receptor, also known as ErbB1 or HER1, that is a 170 kDa transmembrane glycoprotein encoded by c-erbB1 proto-oncogene. EGFR is a member of the human epidermal growth factor receptor (HER) family of receptor tyrosine kinase (RTK), and the family further comprises HER2 (ErbB2), HER3 (ErbB3) and HER4 (ErbB4). EGFR signaling is initiated by ligand binding, and then signal transduction cascade is initiated by inducing conformational changes in the receptor with other ErbB family members, homodimerization or heterodimerization, and trans-autophosphorylation of receptor (see, Ferguson et al., Annu Rev Biophys, 37: 353-73, 2008), thereby finally affecting a variety of cell functions (e.g., cell proliferation and survival). The expression of EGFR or the increased kinase activity thereof is associated with a series of human cancers (see, Mendelsohn et al., Oncogene 19: 6550-6565, 2000; GrUnwald et al., J Natl Cancer Inst 95: 851-67, 2003; Mendelsohn et al., Semin Oncol 33: 369-85, 2006). It has been reported that the increased expression of EGFR is found in numerous cancers, such as, glioma, breast cancer, ovarian cancer, cervical cancer, and the like.

The term "EGFR inhibition" as used herein comprises the decreased EGFR activity, expression or quantity caused by any reasons (e.g., by treatment or the physical conditions of the subject itself). In some embodiments, the by EGFR inhibition is meant that the EGFR activity, expression or quantity is decreased by at least 10%. In some embodiments, the by EGFR inhibition is generally meant that the EGFR activity or quantity is decreased by at least 20%, 40%, 50%, 80%, 90%, 95% or more. In some embodiments, the decrease is based on the comparison with the standard value of the same type of a subject (e.g., the same type of healthy persons or the same type of patients). In some embodiments, the decrease is based on the comparison with the value of the same subject earlier.

EGFR Inhibitor

In some embodiments, the EGFR inhibition is caused by administration of an EGFR inhibitor.

The term "EGFR inhibitor" as used herein generally refers to any EGFR inhibitor that has been known in the art or will be found in the future, including any substance that causes an inhibition of a biological activity associated with the EGFR activity in a subject (including any inhibition of the downstream biological effect caused by the binding of EGFR with its natural ligand(s)) when the substance is administered to the subject. In some embodiments, the EGFR inhibitor comprises any reagent capable of blocking the EGFR activity or any downstream biological effect thereof.

The EGFR inhibitor may be identified or screened by well-known methods in the art, e.g., by detecting the expression level of EGFR after administering the compound to be tested. The expression level of EGFR may be detected by well-known methods in the art, e.g., immunohistochemistry, PCR, RT-PCR, in situ hybridization, Southern blot, Western blot, Northern blot, spectrophotometry and ELISA, etc.

In some embodiments, the EGFR inhibitor is used for treating cancers in the subject.

The term "cancer" as used herein generally refers to any medical condition, which is mediated by the growth, proliferation, or metastasis of tumors or malignant cells, and causes solid tumors or non-solid tumors (e.g., leukemia). The cancers as described in the present application may comprise, but are not limited to, the epithelial malignant tumor (epithelium-derived cancer), lung cancer (e.g., non-small-cell lung cancer), breast cancer, the skin cancer, bladder cancer, colon cancer, gastrointestinal (GI) cancer, prostate cancer, pancreas cancer, uterus cancer, cervical cancer, ovarian cancer, esophageal cancer, head and neck cancer, stomach cancer and laryngeal cancer.

In some embodiments, the EGFR inhibitor may block the kinase activity of EGFR receptor by directly binding to the intracellular domain of EGFR receptor; or reduce or block the biological activity of the EGFR receptor by occupying the ligand binding sites or a portion thereof so that the EGFR receptor cannot access its natural ligand; or reduce the EGFR activity by adjusting the dimerization of EGFR polypeptide or adjusting the interaction between the EGFR polypeptide with other proteins to increase the ubiquitination and endocytosis of EGFR.

In some embodiments, the EGFR inhibitor may be a non-specific EGFR inhibitor, i.e., such inhibitor inhibits other target proteins in addition to EGFR.

In some embodiments, the EGFR inhibitor acts directly on EGFR proteins or nucleic acids encoding EGFR proteins. In some embodiments, the EGFR inhibitor acts directly on EGFR proteins. When describing an inhibitor and a target protein, the term "act directly on" as used herein means that the inhibitor may directly bind to the target protein without the aid of any other molecule (including covalently binding and non-covalently binding).

In some embodiments, the EGFR inhibitor may be a small molecular EGFR inhibitor, a protein macromolecule that binds specifically to EGFR (e.g., antibody or fragment of antigen-binding thereof) or an RNAi or antisense oligonucleotide that inhibit expression of EGFR proteins. In some embodiments, the EGFR inhibitor may be a small molecular EGFR inhibitor or a protein macromolecule that binds specifically to EGFR (e.g., antibody or fragment of antigen-binding thereof).

The term "nucleic acid" as used herein generally refers to a polynucleotide molecule consisting of monomeric nucleotides. Nucleic acids comprise ribonucleic acid (RNA), deoxyribonucleic acid (DNA), single-stranded deoxyribonucleic acid (ssDNA), double-stranded deoxyribonucleic acid (dsDNA), short interfering ribonucleic acid (siRNA) and micro RNA (miRNA). Other non-limiting examples of polynucleotides comprise gene, gene fragment, exon, intron, messenger RNA (mRNA), transfer RNA, ribosome RNA, ribozyme, cDNA, shRNA, single-stranded short or long RNA, recombinant polynucleotide, branched polynucleotide, plasmid, vector, isolated DNA of any sequence, control region, isolated RNA of any sequence, nucleic acid probe and primer. Nucleic acids may be linear or cyclic.

The term "RNAi" as used herein generally refers to RNA interference technology, which involves a process where exogenous or endogenous double-stranded RNA molecules or small RNAs inhibit the expression or translation of genes by targeting and specifically degrading mRNA. RNAi comprises two types of small RNA: microRNA (miRNA) and short interfering RNA (siRNA), which may bind to other mRNA molecules, thereby increasing or decreasing their activity, for instance, preventing mRNA from being translated to proteins. In eukaryotic animals, the RNAi pathways cleaves long double-stranded RNA (dsRNA) into double-stranded siRNA fragments having about 20-23 nucleotides in length by RNaseIII enzyme (e.g., Dicer, DCL or Drosha). Each siRNA is resolved into two single-stranded RNAs (ssRNA), i.e., passenger chain and guide chain. The passenger chain is degraded, while the guide chain is integrated into an RNA-induced silencing complex (RISC). When the guide chain is complementary to the mRNA molecule, RISC cleaves the mRNA molecule, thereby causing the degradation of the mRNA molecule.

The term "oligonucleotide" as used herein generally refers to an oligomer or polymer of ribonucleic acid (RNA) or deoxyribonucleic acid (DNA) or any mimetic or structurally modified nucleic acid thereof. The term comprises naturally oligonucleotides consisting of nucleobases, ribose and covalent nucleoside (backbone), and non-naturally oligonucleotides having similar function. The modified or substituted oligonucleotide is generally superior to the naturally occurring forms as they have e.g., increased affinity to target nucleic acid, increased cell uptake, and increased stability in the presence of nuclease.

The term "antisense oligonucleotide" as used herein generally refers to a single stranded oligonucleotide having a nucleobase sequence that may at least partially hybridize with the corresponding region or fragment of the target nucleic acid. The antisense oligonucleotide in accordance with the present invention may comprise about 8 to about 50 nucleobases (i.e., about 8 to about 50 linked nucleotides). For example, an antisense oligonucleotide may comprise about 12 to about 30 nucleobases. In some embodiments, the antisense oligonucleotide modifies the precursor of the target mRNA, resulting in different splice variants. In some embodiments, the antisense oligonucleotide regulates the expression of one or more different target proteins.

In some embodiments, the antisense oligonucleotide can be modified, and comprises modified ribose, modified internucleotide bond, and/or modified nucleobases. For instance, one or more of a plurality of nucleotides can be modified, e.g., one or more modified nucleotides comprise modified ribose, and/or one or more modified nucleotides comprise modified nucleobases. In some embodiments, the at least a modified ribose can be bicyclic pentose. In some embodiments, at least one modified ribose can comprise 2'-O-methoxyethyl pentose. In some embodiments, the modified nucleobases can be 5-methylcystein. In some embodiments, one or more internucleotide bonds of the antisense oligonucleotides can be modified internucleotide bond. In some embodiments, the modified internucleotide bond may be phosphonothioate internucleotide bond.

The term "small molecular EGFR inhibitor" as used herein generally comprise a small molecular EGFR inhibitor that binds reversibly to EGFR (e.g., Gefitinib, Erlotinib, Sapitinib and Icotinib), a small molecular EGFR inhibitor that binds irreversibly to EGFR (e.g., Afatinib, Dacomitinib, Lapatinib (such as Tykerb®, GW572016 GlaxoSmithKline), Vandetanib (such as ZACTIMA™, ZD6474), Lenvatinib, Canertinib, Varlitinib, and Neratinib) and/or a small molecular EGFR inhibitor that binds specifically to mutant EGFR (e.g., Osimertinib, Nazartinib, Rociletinib, Olmutinib, Avitinib and EAI045).

In some embodiments, the EGFR inhibitor may comprise, but is not limited to, small molecular compound, e.g., those described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008 and 5,747,498, and those described in PCT Patent Application WO98/14451, WO98/50038, WO99/09016 and WO99/24037, which are incorporated herein by reference in their entity.

The small molecular EGFR inhibitor may further comprise PD 183805 (Cl 1033, 2-acrylamide, N-[4-[(3-chloro-4-fluorophenyl)amino]-7-[3-(4-morpholinyl)propoxyl]-6-quinazolinyl]-dihydrochloride, Pfizer, Inc.), ZM105180 (6-amino-4-(3-methylphenyl-amino)-quinazolinyl, Zeneca), BIBX-1382 (N-8-(3-chloro-4-fluorophenyl)-N-2-(1-methylpiperidin-4-yl)-pyrimido[5,4-d]pyrimidin-2,8-diamine, Boehringer Ingelheim), PKI-166 ((R)-4-[4-[(1-phenylethyl)amino]-1H-pyrrolo[2,3-d]pyrimidin-6-yl]-phenol), (R)-6-(4-hydroxylphenyl)-4-[(1-phenylethy)amino]-7H-pyrrolo[2,3-d]pyrimidine), CL-387785 (N-[4-[(3-bromophenyl)amino]-6-quinazolinyl]-2-butyne), EKB-569 (N-(4-((3-chloro-4-fluorophenyl)amino)-3-cyano-7-ethoxy-6-quinolyl)-4-(dimethylamino)-2-but enamide) (Wyeth), Imatinib, STI-571, LFM-A13, PD153035, piceatannol, PP1, AEE788, SU4132, SU6656, Semazanib, SU6668, ZD6126AG1478 (Sugen), and/or AG1571 (SU5271; Sugen).

The protein macromolecule that binds specifically to EGFR may be an EGFR targeting antibody, an antibody variant, a fusion protein, derivative or a fragment thereof. In some embodiments, the protein macromolecule that binds specifically to EGFR is an antibody or its fragment of antigen-binding that binds specifically to EGFR.

The term "specifically binding" as used herein, when used to describe an EGFR inhibitor, generally means that the EGFR inhibitor may recognize EGFR in a complex mixture, and the binding constant of the inhibitor to EGFR is at least 2 times as compared with the binding constant of the inhibitor to other non-specifically binding proteins. In some embodiments, the dissociation constant of the EGFR inhibitor to EGFR may be less than or equal to $10^{-6}$ or $10^{-7}$ M. In some embodiments, the dissociation constant of the EGFR inhibitor to EGFR may be less than or equal to $10^{-7}$ M or $10^{-8}$ M.

The term "fragment of antigen binding" as used herein generally refers to an antibody fragment formed by an antibody fragment containing one or more CDRs but not having an intact antibody structure. Examples of antigen-binding fragments comprise, but are not limited to, Fab fragment, Fab' fragment, F(ab')$_2$ fragment, Fv fragment, single-stranded antibody molecule (scFv), scFv dimer, camelized single domain antibody, and nanobody. The fragment of antigen-binding may bind to the same antigen as the parent antibody.

The "Fab" fragment of an antibody generally refers to the antibody portion formed by a light chain (including a variable region and a constant region) and the variable region and the first constant region of a heavy region linked by disulfide bond.

The "Fab'" fragment generally refers to a Fab fragment including a portion of hinge region.

The "F(ab')$_2$" fragment generally refers to a dimer of Fab'.

The "Fv" fragment of an antibody is comprised of the variable region of a light chain and the variable region of a heavy chain.

The "single-stranded antibody molecules" or "scFv" generally refers to an engineering antibody formed by the variable region of a light chain and the variable region of a heavy chain linked directly or by a peptide chain. The details can be founded in, e.g., Huston J S et al., Proc Natl Acad Sci USA, 85:5879 (1988).

"scFv dimer" generally refers to a polymer formed by two scFvs.

"Camelized single domain antibody" (also known as "heavy chain antibody" or "HCAb (Heavy-chain-only antibodies, HCAb)") generally refers to an antibody containing two heavy chain variable regions but not containing light chain (Riechmann L. and Muyldermans S., J Immunol Methods. December 10; 231 (1-2):25-38 (1999); Muyldermans S., J Biotechnol. June; 74 (4):277-302 (2001); WO94/04678; WO94/25591; U.S. Pat. No. 6,005,079). The heavy chain antibody was initially derived from camelid (camel, dromedary and llama). Although the light chain is deleted, the camelized antibody has all the functions of antigen-binding (see Hamers-Casterman C. et al., Nature. 363 (6428):446-8 (1993); Nguyen VK. et al., Immunogenetics. 54 (1):39-47 (2002); Nguyen VK. et al., Immunology. 109 (1):93-101 (2003)), which are incorporated hereby by reference in their entity.

"Nanobody" generally refers to a polymer comprised of one heavy chain variable region from a heavy chain antibody and two constant regions CH2 and CH3.

In some embodiments, the antibody of the present invention may be a full human antibody, humanized antibody, chimeric antibody, murine antibody or rabbit antibody. In some embodiments, the antibody of the present invention may be polyclonal antibody, monoclonal antibody or recombinant antibody. In some embodiments, the antibody of the present invention may be monospecific antibody, bispecific antibody or polyspecific antibody. In some embodiments, the antibody of the present invention may be further labelled. In some embodiments, the antibody or fragment of antigen-binding thereof may be a full human monoclonal antibody, which is optionally produced by genetically modified rats, e.g., genetically modified rats having inactivated endogenous rat immunoglobulin gene expression and carrying recombinant human immunoglobulin locus with J locus deletion and C-kappa mutation, and which may also be expressed by modified cells (e.g., CHO cells).

The term "full human" as used herein, when used in reference to an antibody or fragment of antigen binding, generally means that the amino acid sequence of the antibody or fragment of antigen-binding corresponds to the amino acid sequence produced by a human or human immune cells, or the amino acid sequence of an antibody derived from a non-human source e.g., generally modified non-human animals utilizing a human antibody library, or other sequences encoding a human antibody.

The term "humanized" as used herein, when used in reference to an antibody or fragment of antigen binding, generally means an antibody or fragment of antigen-binding derived from the CDR of a non-human animal, from the FR region of human, and from a constant region of human (when applicable). In some embodiments, the humanized antibody or fragment of antigen-binding may be used as a therapeutic reagent for human due to the reduced immunogenicity thereof. In some embodiments, the non-human animal may be mammal (e.g., mouse, rat, rabbit, goat, sheep, cavy, and hamster). In some embodiments, the humanized antibody or fragment of antigen-binding may consist essentially of a human sequence, except that the CDR sequence is non-human.

The term "chimeric" as used herein, when used in reference to an antibody or a fragment of antigen-binding, generally means an antibody or fragment of antigen-binding in which at least a portion of a heavy chain and/or a light chain are derived from one species, and the remainder portion of the heavy chain and/or the light chain are derived from different species. In some embodiments, the chimeric antibody may contain a constant region derived from human and a variable region derived from a non-human animal (e.g., mouse or rabbit).

Exemplary protein macromolecules that bind specifically to EGFR may comprise Panitumumab, Necitumumab, Nimotuzumab, Cetuximab, ABX-EGF (human) (Abgenics, San Francisco, Calif.), h-R3 (humanized), MDX-447 (bispecific, EGFR-CK64), MAb 579 (ATCC CRL HB 8506), MAb 455 (ATCC CRL HB8507), MAb 225 (ATCC CRL 8508) and/or MAb 528 (ATCC CRL 8509) (see U.S. Pat. No. 4,943,533) and variants thereof; reconstructed human 225 (H225) (see WO 96/40210); IMC-11F8 (a full-length human antibody targeting EGFR) (Imclone); an antibody targeting EGFR mutation 2 as described in U.S. Pat. No. 5,212,290; a humanized chimeric antibody binding to EGFR as described in U.S. Pat. No. 5,891,996; EMD 55900 (Stragliotto et al., Eur. J. Cancer 32A:636-640 (1996)); HuMax-EGFR (GenMab); full human antibodies E1.1, E2.4, E2.5, E6.2, E6.4, E2.11, E6.3 and E7.6.3 as described in U.S. Pat. No. 6,235,883; mAb 806 or humanized mAb 806 (Johns et al., J. Biol. Chem. 279 (29):30375-30384 (2004)).

In some embodiments, the EGFR inhibitor may comprise Cetuximab, Gefitinib, Erlotinib, Icotinib, Sapitinib, Afatinib, Lapatinib, Vandetanib, Neratinib, Brigatinib, Panitumumab, Necitumumab, Nimotuzumab, Tesevatinib, Allitinib, Theliatinib, Rociletinib, Canertinib, Mubritinib, AZD3759, YZJ-0318, Neptinib, Naquotinib, PF-06747775, SPH1188-11, Poziotinib, Epitinib, Varlitinib, Alflutinib, HM61713, CK-101, Pyrotinib, Larotinib, HS-10296, AP32788, Simotinib, GMA204, Virlitinib, Yinlitinib, Nazartinib, Rociletinib, Olmutinib, Osimertinib, Dacomitinib, Avitinib and/or EAI045. In some embodiments, the EGFR inhibitor may comprise Cetuximab, Gefitinib, Erlotinib, Icotinib, Sapitinib, Afatinib, Lapatinib, Vandetanib, Lenvatinib, Neratinib, Canertinib, Varlitinib, Nazartinib, Rociletinib, Olmutinib, Osimertinib and/or EAI045.

EGFR Inhibitor Administered in Combination with Other Cancer Therapies

In some embodiments, the EGFR inhibitor may be administered in combination with one or more of other cancer therapies. The other cancer therapies may be conventional means for treating cancers in the art, e.g., cytotoxic anticancer agents, immunotherapeutic anticancer agents, or hormonotherapeutic anticancer agents. In accordance with the present application, a medicament for treating cancers may also be used in combination with radiotherapy or surgery therapy. In some embodiments, the EGFR inhibitor and the additional anticancer agents, when used in combination, may be simultaneously administered to a subject, or individually administered at intervals.

In some embodiments, the EGFR inhibitor of the present application may be administered together with one or more of additional anticancer agents. In some embodiments, the one or more of additional anticancer agents may be administered separately from the EGFR inhibitor of the present invention as part of a multi-dose regimen (e.g., administered sequentially or in separate overlapping regimens). In some embodiments, these anticancer agents may be a part of a single dosage form, which may be mixed with the EGFR inhibitor of the present invention to form a single composition. In another embodiment, these agents may be approximately simultaneously administered with the EGFR inhibitor as separate doses. When the EGFR inhibitor of the present invention is simultaneously administered with the one or more of additional anticancer agents, the EGFR inhibitor is administered at a dose level of about 1-99% (e.g., about 5-95%, about 1%, about 5%, about 10%, about 20%, about 30%, about 40%, about 50%, about 60%, about 70%, about 80%, about 90%, about 95% or about 99%) in relation to the total dosage.

The cytotoxic anticancer agents for use in the treatment of cancers may comprise alkylating agents such as nitrogen mustard, nitrogen mustard N-oxide hydrochloride, chlorambucil, cyclophosphamide, ifosfamide, thiotepa, isothiocyanate, busulfan, nimustine hydrochloride, mituoxiva, melphalan, dacarbazine, ranimustine, promethamine sodium phosphate, diethylenetriamine, carmustine, lomustine, streptozotocin, pipobroman, ethoglucid, carboplatin, cisplatin, miriplatin, nedaplatin, oxaliplatin, tenetamide, omustine, dichloropyridine, Flupitstein, Prednisetine, pumitepa, ribomustin hydrochloride, temozolomide, diclofenac, trovafloxacin, zinstatin simvastatin, penems, cystemustine and bizelesin; antimetabolites such as mercaptopurine, 6-mercaptopurine riboside, thioinosine, methotrexate, pemetrexed, Vortioxetin, cytarabine, Tizanidine Hydrochloride, 5-FU and its derivatives (e.g., fluorouracil, tegafur, UFT, Doxycycline, carmofur, capecitabine, etc.), aminopterin, zolathiamine, calcium leucovorin, bronchopneumonia bacteria, calcium folate, L-carnitine calcium fumarate, Cladribine, emitefore, Fludarabine, Gemcitabine, hydroxylurea, pentostatin, piritrexim, iodouridine, mitotane, thiazole furan, oseltamivir and bendamustine; antitumor antibiotics such as actinomycin D, actinomycin C, mitocymin C, chromomycin A3, bleomycin hydrochloride, bleomycin sulfate, cetirizine hydrochloride, rubicin hydrochloride, mitoxantrone hydrochloride and idarubicin hydrochloride; and vegetable-derived cytotoxic anticancer agents such as, etoposide, etoposide phosphate, vinblastine sulfate, vincristine sulfate, teniposide, paclitaxel, docetaxel and vinorelbine etc.; and/or VEGF inhibitor such as, Bevacizumab, and those VEGF inhibitors as disclosed in PCT Patent Application WO 2005/012359, WO 2005/044853, WO 98/45332, WO 96/30046, WO 94/10202, U.S. Pat. Nos. 7,060,269, 6,582,959, 6,703,020, 6,054,297, U.S. Patent Application US2006/009360, US2005/0186208, US2003/0206899, US2003/0190317, US2003/0203409 and US2005/0112126.

The immunotherapeutic anticancer agents for use in the treatment of cancers may comprise bubinini, Crestatin, Benzofurazan, lentinan, ubenimex, interferon, interleukin, macrophage colony stimulating factor, granulocyte colony stimulating factor, erythrogenin, lymphotoxin, BCG vaccine, *corynebacterium*, everolimus, levamisole, polysaccharide K, procodazole and immune checkpoint inhibitor (e.g., CTLA4 inhibitor, TIM-3 inhibitor, PD-1 inhibitor (e.g., Nivolumab, Pembrolizumab, Pidilizumab, AMP514 (Amplimmune), AMP-224, and other PD-1 inhibitors as disclosed in PCT Patent Application WO2006/121168, WO2009/114335, WO2009/101611, U.S. Pat. No. 8,609,089, U.S. Patent Application US2010/028330, US2012/0114649) and/or PD-L1 inhibitor (e.g., atezolizumab, aceluma, durvalumab, YW243.55.570, MPDL3280A, MEDI-4736, MSB-0010718C, MDX-1105, and other PD-L1 inhibitors as disclosed in PCT Patent Application WO2010/077634 and U.S. Pat. No. 7,943,743)).

The hormonotherapeutic anticancer agents for use in the treatment of cancers may comprise urinastatin, diethylstilbestrol, chlorinated costen, medroxyprogesterone, megestrol acetate, cyproterone acetate, danazol, allylestrenol, progesterone, mepartricin, raloxifene or meloxifene, levolfloxacin, antiestrogen (e.g., tamoxifen citrate, toremifene citrate, etc.), contraceptive, prostacyclin, testolactone, aminosuccinimide, LH-RH agonist (e.g., goserelin acetate, buserelin, leuprorelin, etc.), droloxifene, epiandrostanol, ethinyloestradiol sulfonate, flubendazole, anastrozole, letrozole, exemestane, vorozole, antiandrogen (e.g., flutamide, biculutamide, nilutamide, etc.), 5α-reductase inhibitor (e.g., finasteride, epristeride), corticosterodes (e.g., dexamethasone, prednisolone, betamethasone, triamcinolone, etc.) and androgen synthesis inhibitor (e.g., abiraterone, etc.).

Epithelial Diseases

The term "epithelial/epithelium" as used herein generally comprises one or more layers of free and surface-closed cells covering the overall body, including skin, mucus, cavity, slurry, and gland spaces. All the epithelial layers comprise two special domains: a top domain facing a mucosa (or cavity) space, and a basolateral membrane facing a chorion (or deep layer) space. Thus, an important function of the epithelial tissue is to provide a proper barrier to isolate and control a variety of biological processes between the two spaces. The epithelium tissues are comprised of epithelial cells and endothelial cells. Epithelial cells may comprise cutaneous epithelial cells, oral epithelial cells, gastric epithelial cells, and/or intestinal epithelial cells.

The term "epithelial diseases" as used herein generally refers to diseases caused by lesions of epithelial and/or endothelial cells (e.g., epithelial and/or endothelial cell lesions associated with inhibition of EGFR or by administration of EGFR inhibitors). In some embodiments, the "epithelial diseases" may comprise diseases or disorder selected from the following group: EGFR-inhibition associated rash, EGFR-inhibition associated acne, EGFR-inhibition associated skin pruritus, EGFR-inhibition associated alopecia, EGFR-inhibition associated hand-foot syndrome, EGFR-inhibition associated hair changes, EGFR-inhibition associated erythema, EGFR-inhibition associated skin exfoliation, EGFR-inhibition associated herpes, EGFR-inhibition associated hirsutism, EGFR-inhibition associated hyperpigmentation, EGFR-inhibition associated nail disorders, EGFR-inhibition associated paronychia and schizonychia, EGFR-inhibition associated xerosis cuits, EGFR-inhibition associated hypersensitivity, EGFR-inhibition associated mucositis, EGFR-inhibition associated nasopharyngitis, EGFR-inhibition associated epistaxis, EGFR-inhibition associated xerostomia, EGFR-inhibition associated cheilitis, EGFR-inhibition associated oral ulcer and/or EGFR-inhibition associated gastrointestinal mucosal injury. For example, the epithelial tissue disease can comprise hand-foot syndrome associated with inhibition of EGFR. For example, the epithelial tissue disease can comprise rash associated with inhibition of EGFR.

In the present application, the term "hand and foot syndrome" is also known as Hand-Foot Syndrome (HFS). It was first described in 1984 by Jacob Lokich and Cery Moor of the Harvard Medical School in New England. The typical clinical manifestations are progressive. The main clinical manifestations are heat, pain, and erythema swelling. In severe cases, it develops into desquamation, ulcers, and severe pain. The pathological manifestations of HFS mainly include, for example, basal keratinocyte vacuolar degeneration, perivascular lymphocytes infiltration of skin, keratinocyte apoptosis, and skin edema. For example, HFS may include feeling dull of the palms and soles, or erythema of the extremities caused by chemotherapy. Tumor patients may experience symptoms during chemotherapy or molecular targeted therapy (such as EGFR inhibitors).

Hand-foot syndrome (HFS) currently has a variety of grading methods, among which the National Cancer Institute (NCI) grading standards are more commonly used. This grading classifies hand-foot syndrome into three grades: grade 1 is mild skin changes or dermatitis with sensation abnormalities (such as fingerprint disappearance, hyperpigmentation, erythema, peeling, paresthesia, dysesthesia, skin numbness, etc.), but do not affect daily activities; grade 2 is the same skin changes of grade 1, accompanied by pain, mildly affecting daily activities, the skin surface is intact; grade 3 is ulcerative dermatitis or skin changes with severe pain, which seriously affects daily life and has obvious tissue damage (such as desquamation, blisters, hemorrhage, edema, etc.).

In addition, the World Health Organization (WHO) classifies HFS as four grades: grade 1 is a feeling of dysesthesia, paresthesia or tingling in the hands and feet; grade 2 is discomfort when holding subjects and walking, painless swelling, or erythema. grade 3 is painful erythema and swelling of the palms and soles, erythema and periungual swelling; grade 4 is desquamation, ulceration, blistering and severe pain.

Depending on the locations where the diseases occur, the epithelial diseases may be classified into epithelial cell diseases and/or endothelial cell diseases. In some embodiments, the EGFR-inhibition associated epithelial cell diseases may be classified into skin epithelial cell diseases (e.g., rash, acne, rosacea, atopic dermatitis, contact dermatitis, seborrheic dermatitis, lupus, scleroderma, pemphigus, pigmentation, black spot, leukoderma, urticaria, tinea corporis, the skin pruritus, alopecia, hair changes, erythema, paronychia and schizonychia, xerosis cuits, hypersensitivity and psoriasis), EGFR-inhibition associated oral epithelial cell diseases (e.g., pemphigus, herpetic labialis, herpetic stomatitis, granulomatous cheilitis, oral ulcer, pemphigoid, xerostomia syndrome, Bechet disease and oral sarcoidosis, etc.), EGFR-inhibition associated stomach epithelial cell diseases (e.g., gastritis, intestinal metaplasia, gastric perforation, gastric fistula, gastric ulcer and gastrointestinal polyp) or EGFR-inhibition associated small intestine epithelial cell diseases (e.g., enteritis, Crohn's disease, enterobrosis, intestinal fistula, enterelcosis, ulcerative colitis and NSAIDs bowel disease).

In some embodiments, the epithelial cell diseases may be skin epithelial cell diseases. In some embodiments, the skin epithelial cell diseases may be rash and pruritus.

The term "rash" as used herein refers to a skin change capable of affecting the color, appearance, or texture of skin. The rash may be localized at only a part of the body, or affect the overall skin. The rash may also comprise urticaria.

In some embodiments, the endothelial cell may be vascular endothelial cell. In some embodiments, the endothelial cell diseases may be vascular endothelial cell diseases. The vascular endothelial cell diseases may comprise endothelial dysfunction which may manifest as an imbalance in the production or the reduced bioavailability and/or a relative contribution to endothelium-derived relaxation and contraction of nitric oxide. The vascular endothelial cell disease may comprise, but be not limited to, EGFR-inhibition associated degenerative vascular diseases (e.g., atherosclerosis, media arteriosclerosis and arteriolosclerosis (e.g., hyalinizative arteriolosclerosis and proliferative arteriolosclerosis)), EGFR-inhibition associated inflammatory vascular diseases (e.g., infectious arteritis, arteritis syphilitica, giant cell arteritis, thromboangiitis obliterans and rheumatic arteritis), EGFR-inhibition associated functional vascular diseases (e.g., Raynaud's disease, acrocyanosis and erythema acrodynia) and EGFR-inhibition associated congenital vascular diseases (e.g., congenital arteriovenous fistula) and the like.

The severity grading of epithelial diseases may be based on the Common Adverse Event Terminology Criteria (CTCAE) issued by U.S. National Cancer Institute, which is the standard classification and severity grading criteria for adverse events in cancer treatment clinal trials and other oncology settings (NCI-CTCAE V5.0). In some embodiments, the severity grading of epithelial diseases may be grade 1 or above, grade 2 or above, grade 3 or above, grade 4 or above, or grade 5 as evaluated in accordance with NCI-CTCAE V5.0.

Nitric Oxide Releasing Agent

Nitric oxide synthase (NOS) is an enzyme capable of acting on some nitrogen-containing substances in cells to generate nitric oxide (NO). NOS comprises three subtypes, which are inducible nitric oxide synthase (iNOS), isotype nitric oxide synthase found in endothelial cells (eNOS) and isotype nitric oxide synthase found in brain and nerve cells (nNOS). NOS produces NO by oxidizing L-Arg in mammals and some bacteria.

The term "nitric oxide releasing agent" as used herein generally refers to any substance capable of directly or indirectly contributing to, producing and/or releasing nitric oxide and/or stimulating the endogenous production of nitric oxide in the body. In some embodiments, the nitric oxide releasing agent may directly contribute to, produce and/or release nitric oxide. In some embodiments, the nitric oxide releasing agent contributes to, produces and/or releases nitric oxide by stimulating other substances. In some embodiments, the nitric oxide releasing agent serves as a reactant of a chemical or enzyme-catalyzed reaction and contributes to, produces and/or releases nitric oxide via such reaction. In some embodiments, the nitric oxide releasing agent serves a reactant of a chemical or enzyme-catalyzed reaction, and stimulates other substances to contribute to, produce and/or release nitric oxide via such reaction. In some embodiments, the nitric oxide releasing agent may comprise NO.

The nitric oxide releasing agents may be identified or screened by methods well known in the art, e.g., it is possible to detecting the ability of the compound to be tested for contributing, producing, releasing and/or directly or indirectly transferring nitric oxide and/or stimulating the endogenous production of nitric oxide in the body by detecting the levels of nitrite, NO, $NO_2^-$ and/or S-nitrosothiol. Any method known in the art may be used to detect the level of nitrite, NO, $NO_2^-$ and/or S-nitrosothiol. In some embodiments, the nitric oxide releasing agents may be identified or screened by detecting nitrite, e.g., analyzing nitrite by Griess Analysis (Molecular Probes), which is on the basis of reacting nitrite with p-aminobenzenesulfonic acid, followed by detecting the reaction product via spectrophotometry. It is also possible to carry out the measurement by reducing nitrite/nitrate to NO in a reflux chamber at 95° C. by a highly sensitivity chemiluminescence technology. In some embodiments, it is possible to identify or screen the nitric oxide releasing agents by detecting the Hb-NO level in blood. It is known that NO binds closely to hemoglobin (Hb), and the interaction between NO and Hb is known as the primary pathway of NO metabolism in blood vessels. Thus, the Hb-NO level in blood is a good indicator of the endogenous production of NO. In some embodiments, it is possible to determine the paramagnetic hemoglobin-NO adduct (Hb-NO) in the whole blood and the erythrocytes by electron paramagnetic response (EPR) spectroscopy so as to identify or screen the nitric oxide releasing agents. In some embodiments, it is possible to identify or screen the nitric oxide releasing agents by amperometry of NO-specific electrode. This method requires inserting a NO electrode into the living body or sample. In some embodiments, it is possible to identify or screen the nitric oxide releasing agents by detecting S-nitrosothiol. In EcoMedics CLD 88 Exhalyzer (Annex, Herts, UK), the S-nitrosothiol of a protein is measured by using chemiluminescence detection (Feelisch, M. et al., Concomitant S-, N-, and heme-nitros(yl)ation in biological tissues and fluids: implications for the fate of NO in vivo. FASEB. J 16, 1775-85 (2002)). In some embodiments, it is possible to indirectly detect the NO level so as to identify or screen the nitric oxide releasing agents. For instance, an EndoPAT method is used to perform a non-invasive endothelial function detection to measure the NO level. The particular detection method may be found in U.S. Pat. No. 9,696,324. It is also possible to indicate the NO level in serum by means of specifically reducing $NO_3^-$ to $NO_2^-$ bp using a nitrate reductase, reacting $NO_2^-$ with a color developer to generate a colored substance, and measuring the absorbance, thereby identifying or screening the nitric oxide releasing agents.

In some embodiments, the nitric oxide releasing agent may be capable of contributing to, producing and/or releasing at least one of $NO^+$, $NO^-$, $N_2O$, NO, $N_2O_3$, $NO_2$, $NO_3^-$ and $NO_2^-$. In some embodiments, the nitric oxide releasing agent may be capable of contributing to, producing and/or releasing at least one nitric oxide in a redox manner ($NO^+$, $NO^-$ and NO). In some embodiments, the nitric oxide releasing agent may be capable of directly or indirectly producing NO upon administration to the subject. Nitric oxide may be released from the nitric oxide releasing agents via any suitable mechanism, including the reaction with a proton source (e.g., a proton donator, such as, water) and/or thermal degradation.

In some embodiments, the nitric oxide releasing agent completes the release of nitric oxide or contributes to nitric oxide such that the biological activity of the nitric oxide species may be achieved at the intended action site.

In some embodiments, the nitric oxide releasing agent may comprise one or more NO-donating groups selected from the following group: diazeniumdiolate, hydroxydiazenene sulfonic acid, S-nitrosothiol, furoxan, oxime, N-nitrosamine, N-hydroxy guanidine, nitrate, nitrite, nitric ester, nitrous acid ester, sydnonimine, sydnone, oxatriazole-5-imine, oxatriazole-5-one, hydroxylamine, dioxadiazacyclobutene, N-hydroxynitrosamine, N-nitroso imine, hydroxyureas and/or metal nitrosamino complexes. For example, the nitric oxide releasing agent may comprise the following one or more NO-donating groups: diazeniumdiolate, N-diazeniumdiolate, hydroxyldiazenesulfonic acid, S-nitrosothiol, furoxan, oxime, nitrosoamine, nitric ester, nitrous acid ester, sydnonimine, N-hydroxy-guanidine, nitric acid, nitrous acid, sydnonimine, sydnone, oxatriazole-5-imine, oxatriazol-5-one, hydroxylamine, dioxadiazacyclobutene, N-hydroxy-nitrosoamine, N-nitrosoimine, hydroxylurea, metal nitrosamino complex, hydroxynitrosamine, nitrosothiol, hydroxylamine, hydroxylurea, N-nitroso-N-acetypenicillamine (SNAP), minoxidil, organic nitric acid, metal-NO complex, thionine, furanose and/or benzofuran.

For example, the nitric oxide releasing agent may have one or more NO donor groups selected from Table 1:

TABLE 1

| \multicolumn{3}{c}{NO donor groups} | | |
| No. | Compound Name | Compound Structure |
| --- | --- | --- |
| 1 | Diazeniumdiolate | 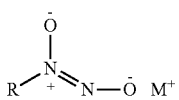 |
| 2 | O²-substituted diazeniumdiolate | 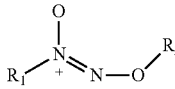 |
| 3 | Hydroxydiazene sulfonic acid | 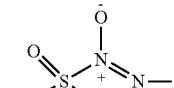 |
| 4 | S-nitrosothiol | 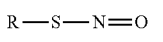 |
| 5 | Furoxan | 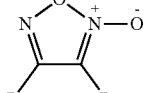 |
| 6 | Oxime | 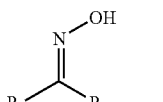 |
| 7 | N-nitrosamine | 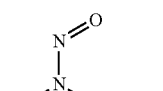 |
| 8 | N-hydroxyguanidine | 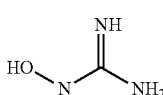 |
| 9 | Nitrate | 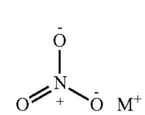 |

TABLE 1-continued

NO donor groups

| No. | Compound Name | Compound Structure |
|---|---|---|
| 10 | Nitric ester | O=N(+)(O−)−O−R |
| 11 | Nitrite | O=N−O− M+ |
| 12 | Nitrous acid ester | O=N−O−R |
| 13 | Sydnonimine | HN=C−O−N=N(+)(R$_2$)−C(R$_1$)= (ring) |
| 14 | Sydnone | O=C−O−N=N(+)(R$_2$)−C(R$_1$)= (ring) |
| 15 | Oxatriazole-5-imine | HN=C−O−N=N(+)(R)−N= (ring) |
| 16 | Oxatriazole-5-one | O=C−O−N=N(+)(R)−N= (ring) |
| 17 | Hydroxylamine | $H_2N-OH$ |
| 18 | Dioxadiazacyclobutene | N=N, O−O (4-membered ring) |
| 19 | N-hydroxynitrosamine | R−N(OH)−N=O |
| 20 | N-nitroso imine | R$_1$R$_2$C=N−N=O |
| 21 | N-hydroxyurea | HO−NH−C(=O)−NH$_2$ |
| 22 | Metal nitrosamino complex | $M_aX_b[N(=O)-NH_2]_n$ |

In some embodiments, the nitric oxide releasing agent may be organic molecules, inorganic molecules, polymers or nanomaterials, ammonia-oxidizing microorganisms (AOM) and any combination thereof. The "polymer" as used herein refers to any compound having a molecular weight of 500 Daltons or above. Accordingly, any compound having a molecular weight of 500 Daltons or below may be referred as "small molecule".

In some embodiments, the small molecule nitric oxide releasing agent may be an organic molecule or an inorganic molecule.

In some embodiments, the nitric oxide releasing agent is an organic molecule, which may comprise nitroglycerin, isosorbide mononitrate, butanediol mononitrate, pentaerythritol tetranitrate, isosorbide dinitrate, trolnitrate, nicorandil, nitro dihydroxyl methyl butanol, 5-amino-3-(4-morpholinyl)-1,2,3-oxadiazole, isoamyl nitrite, 3,3-di (aminoethyl)-1-hydroxyl-2-carbonyl-1-triazene (NOC-18), sulfo NONOate disodium salt, S-nitrosoglutathione, S-Nitroso-N-acetylpenicillamine, 4-Phenyl-3-furoxancarbonitrile, (±)-(E)-4-Ethyl-2-[(E)-hydroxyimino]-5-nitro-3-hexenamide, streptozocin, NG-Hydroxy-L-arginine acetate salt, $O_2$-(2,4-Dinitrophenyl) 1-[(4-ethoxycarbonyl)piperazin-1-yl]diazen-1-ium-1,2-diolate, N-nitrosodibutylamine, 3-morpholino-sydnonimine (SIN-1), linsidomine, molsidomine, 3-(4-acetylphenyl)sydnone, diethylamine NONOate/A M and/or itramin and those described in U.S. Pat. No. 5,650,442. In some embodiments, the nitric oxide releasing agent may comprise nitroglycerin, isosorbide mononitrate or isosorbide dinitrate.

In the present application, when the nitric oxide releasing agent comprises nitroglycerin, isosorbide mononitrate and/or isosorbide dinitrate, it may be used to prepare medicaments of preventive or therapeutic epithelial tissue disease associated with EGFR inhibition (e.g., an EGFR inhibition associated rash or EGFR inhibition associated pruritus). For example, an EGFR inhibition associated rash or EGFR inhibition associated pruritus may be at least 10% relieved.

In some embodiments, the nitric oxide releasing agent may be an inorganic molecule, which comprises nitryl complex, nitrosyl complex (metal nitrosyl complex), metal nitrosamino complex, nitrate, nitrite, and sodium nitroprusside. In some embodiments, the nitric oxide releasing agent can be sodium nitroprusside.

In the present application, when the nitric oxide releasing agent may be sodium nitroprusside, it can be used for the preparation of a medicament for preventing or treating an epithelial tissue disease associated with EGFR inhibition (for example, an EGFR-inhibition associated rash or EGFR-inhibition associated pruritus). For example, an EGFR-inhibition associated rash or EGFR-inhibition associated pruritus is at least 10% relieved.

In some embodiments, the nitric oxide releasing agent may be a polymer containing a NO-donating group. For example, the NO donor group may comprise the NO donor group described in Table 1. Any suitable polymer may be used, including crosslinked or uncross linked polymer, dendritic polymer, metal compound, organic metal compound, inorganic compound and other polymer support. The NO-releasing polymers comprise, e.g., NO-releasing co-condensation silica, such as, diazoxide disulfate-functionalized polysiloxane, NO-releasing zeolite (see, U.S. Patent Application US2006/0269620 or US2010/0331968), NO-releasing metal organic framework (MOF) (see, U.S. Patent Application US2010/0239512 or US2011/0052650), NO-releasing multi-donor compound (see, U.S. Patent Application US2014/0171395), NO-releasing dendritic polymer or metal structure (see, U.S. Patent Application US2009/0214618), NO-releasing coating (see, U.S. Patent Application US2011/0086234), and the compounds described in U.S. Patent Application US2010/0098733 and PCT Patent Application WO2012/100174, the disclosure of which are hereby incorporated by reference in their entity. In some embodiments, the nitric oxide releasing agent is a nanomaterial containing NO-donating group(s), e.g., nanocrystal that is a co-condensation siloxane network formed by silica dioxide.

In particular, the NO-releasing polymers further may comprise S-nitrosothiolsilica nanospheres, S-nitrosoethanedithiolchitin, oligo-propylenediamine grafted chitosan nucleophilic complexes, the nitric oxide releasing agents manufactured by Novan Inc. (e.g., SB204, SB206, SB208, SB414 or NVN3100) and those disclosed in U.S. Pat. Nos. 8,282,967, 8,956,658, 8,962,029, 9,403,851, 9,403,852, 9,187,501, 8,399,005, 8,981,139, 9,713,652, 9,238,038, 9,669,041, 8,591,876, 9,526,738, 9,737,561, 9,427,605, U.S. Patent Application US2009/0214618, US2012/0021055, US2012/0034169, US2014/0005426, US2014/0058124, US2015/0182543, US2016/0060279, US2014/0065200, US2015/0225488, US2010/0297200, US2013/0196951, US2013/0344334, US2014/0017121, US2011/0086234, US2014/0134321, US2010/0098733, US2012/0230921, US2014/0171395, US2016/0083339, US2016/0199295, US2014/0255318, US2017/0246205, US2012/0136323, US2012/0156163, US2014/0057001, US2012/0134951, US2017/0056437, US2017/0312307, US2017/0216197, US2015/0024052, US2008/0311163, US2016/0256366, US2015/0111973, US2017/0196905, PCT Patent Application WO2017/079268, WO2004/009253, WO2017/151905, WO2016/160089 and WO2017/019614.

In the present application, the oligo-propylene diamine grafted chitosan nucleophilic complex may comprise an azothanondiol salt. For example, the nitric oxide releasing agent may be an oligopropylene diamine grafted chitosan NONOate. In the present application, NONOate may refer to a compound comprising the formula $R^1R^2N$—$(NO^-)$—$N=O$, wherein both $R^1$ and $R^2$ are alkyl.

In the present application, the nitric oxide releasing agent may comprise an ammonia oxidating microorganism (AOM), and the ammonia oxidation microorganism (AOM) may comprise an ammonia oxidizing bacteria (AOB). For example, the ammonia oxidizing microorganism (AOM) may comprise *Nitrosomonas*, Nitrosococcus, Nitrosospira, Nitrosocystis, Nitrosolobus and/or Nitrosovibrio. For example, the ammonia oxidizing microorganism (AOM) may comprise a nitric oxide-releasing microbial population of AOBiome, LLC (e.g., AOB101, AOB102, AOB103, AOB201, AOB201, or AOB203), and U.S. Pat. Nos. 7,820,420B2, 9,738,870B2, WO2017004534A2, U.S. Ser. No. 10/078,054B2, US2017189454A1, US20170191109A1, US20180092948A1, WO2018057710A1, WO2018017583A1, WO2018111888A1, US20070148136A1, US2005106126A1, US20170037363A1, CN1997731A, US20170189454A1 and WO2017004557A1.

In some embodiments, the nitric oxide releasing agent may have a molecular weight of less than 2000, less than 1500, less than 1200, less than 1000, less than 900, less than 800, less than 700, less than 600, less than 500, less than 400, less than 300, less than 200 or less than 100 Daltons. For example, the nitric oxide releasing agent may have a molecular weight less than or equal to 2000 Daltons, less than or equal to 1500 Daltons, less than or equal to 1200 Daltons, less than or equal to 1000 Daltons, less than or equal to 900 Daltons, less than or equal to 800 Daltons, less than or equal to 700 Daltons, less than or equal to 600 Daltons, less than or equal to 500 Daltons, less than or equal to 400 Daltons, less than or equal to 300 Daltons, less than or equal to 200 Daltons and/or less than or equal to 100 Daltons.

In some embodiments, the nitric oxide releasing agent may be transdermal absorbed. In some embodiments, the nitric oxide releasing agent is positively charged, electrically neutral, or negatively charged under physiological conditions. In some embodiments, the nitric oxide releasing agent has a log P ranging from 1 to 5. In some embodiments, the nitric oxide releasing agent has a log P ranging from 1.5 to 3.5.

Method of Prevention and Treatment

The method in accordance with the present invention comprises administering to a subject in need thereof an effective amount of nitric oxide releasing agents, so as to prevent or treat EGFR inhibition-associated epithelial diseases.

The term "prevention" as used herein generally refers to the prevention of occurrence, recurrence, or spread of diseases or one or more symptoms thereof. In the context of the present application, the "prevention" may be interchangeably used with the "preventive treatment". In some embodiments, the "prevention" refers to the treatment of providing a patient suffering from the diseases or disorders as described in the present invention with the medicament in accordance with the present invention with or without administration of other medicaments as described in the present application prior to the occurrence of any symptom. In some embodiments, the patients having a family history of particular diseases may be deemed as candidates of the preventive regimen. In some embodiments, the patients having a history of symptom recurrence are also potential subjects of prevention.

The term "treatment" as used herein generally refers to eliminate or improve one or more symptoms associated with the diseases. In some embodiments, the treatment generally refers to eliminate or ameliorate a disease by administering one or more therapeutic agents to the patients with such disease. In some embodiments, the "treatment" may be administering a medicament in the presence or absence of other therapeutic medicament(s) after the occurrence of a particular disease.

The term "subject" as used herein generally refers to a human or non-human animal (including mammal) in need of diagnosing, prognosing, improving, preventing and/or treating diseases, especially those in need of treatment or prevention by using a nitric oxide releasing agent. The subject can include a cancer patient. For example, the cancer patient may have been, being, and/or will be administered an EGFR inhibitor. For example, the EGFR inhibitor may be an EGFR inhibitor as described herein.

In some embodiments, the subject may be a human or non-human mammal. The non-human mammal may comprise any mammalian species other than human, e.g., livestock (e.g., cow, pig, sheep, chick, rabbit or horse), or rodents (e.g., rat and mouse), or primate (e.g., gorilla and monkey), or domestic animal (e.g., dog and cat). The "subject" may be male or female, and may also be at different ages. The human "subject" may be Caucasian, African, Asian, Semite, or other races, or hybrids of various races. The human "subject" may be elderly, adult, adolescent, child, or infant.

In some embodiments, after administration of the nitric oxide releasing agent of the present application, the severity of the epithelial tissue disease of the subject may be relieved. In some embodiments, the relief may mean that the severity grading of the epithelial diseases of the subject was decreased, e.g., from Grade 5 to Grade 1 (e.g., from Grade 5 to Grade 4, from Grade 5 to Grade 3, from Grade 5 to Grade 2, from Grade 4 to Grade 3, from Grade 4 to Grade 2, from Grade 4 to Grade 1, from Grade 3 to Grade 2, from Grade 3 to Grade 1 or from Grade 2 to Grade 1) as evaluated in accordance with the standard of NCI-CTCAE V5.0. In some embodiments, the amelioration generally means that the occurrence or development of the epithelial disease in the subject is delayed.

In some embodiments, by administering to an subject in need thereof an effective amount of the nitric oxide releasing agents of the present application, the severity grading of rash or pruritus of the subject may be decreased from Grade 5 to Grade 1 (e.g., from Grade 5 to Grade 4, from Grade 5 to Grade 3, from Grade 5 to Grade 2, from Grade 4 to Grade 3, from Grade 4 to Grade 2, from Grade 4 to Grade 1, from Grade 3 to Grade 2, from Grade 3 to Grade 1 or from Grade 2 to Grade 1).

In some embodiments, the nitric oxide releasing agent as used in the method of the present application may be nitroglycerin, isosorbide mononitrate or isosorbide dinitrate, and the epithelial disease to be prevented or treated is rash or pruritus. In some embodiments, by administering to an subject in need thereof an effective amount of nitroglycerin, isosorbide mononitrate or isosorbide dinitrate, the severity grading of rash or pruritus of the subject may be decreased from Grade 5 to Grade 1 (e.g., from Grade 5 to Grade 4, from Grade 5 to Grade 3, from Grade 5 to Grade 2, from Grade 4 to Grade 3, from Grade 4 to Grade 2, from Grade 4 to Grade 1, from Grade 3 to Grade 2, from Grade 3 to Grade 1 or from Grade 2 to Grade 1).

In some embodiments, the nitric oxide releasing agent as used in the method of the present invention may be sodium nitroprusside, and the epithelial disease to be prevented or treated is rash or pruritus. In some embodiments, by administering to a subject in need thereof an effective amount of sodium nitroprusside, the severity grading of rash or pruritus of the subject may be decreased from Grade 5 to Grade 1 (e.g., from Grade 5 to Grade 4, from Grade 5 to Grade 3, from Grade 5 to Grade 2, from Grade 4 to Grade 3, from Grade 4 to Grade 2, from Grade 4 to Grade 1, from Grade 3 to Grade 2, from Grade 3 to Grade 1 or from Grade 2 to Grade 1).

The term "effective amount" as used herein generally refers to an amount of medicament capable of ameliorating or eliminating diseases or symptoms of the subject, or preventively inhibiting or prohibiting the occurrence of diseases or symptoms. The effective amount may be an amount of medicament capable of ameliorating one or more diseases or symptoms to some extent in the subject; an amount of medicament capable of partially or completely restoring the biological or biochemical parameters associated with the causes of diseases or symptoms to normal; and/or an amount of medicament capable of reducing the possibility of the occurrence of diseases or symptoms.

Therapeutically effective amount of the nitric oxide releasing agent as provided in the present application may depend on a variety of factors which are well known in the art, e.g., the activity of the particular compound, body weight, age, sex, diet, excretion rate, medical history, current therapy, time of administration, dosage form, administration mode, administration route, combination of medicaments, health conditions or cross infection potential of the subject, allergy, hypersensitivity, and side effects, and/or degree of epithelial disease development. The skilled man in the art (e.g., physicians or veterinarians) may decrease or increase the administration dosage in portion in accordance with these or other conditions.

The effective amount in humans may be derived from the effective amount in the laboratory animals. For instance, Freireich et al. describe the relation between the dosages in animals and humans (milligrams per square meter of body surface) (Freireich et al., Cancer Chemother. Rep. 50, 219 (1966)). The body surface area may be approximately determined in accordance with the height and body weight of the patient. See, e.g., Scientific Tables, Geigy Pharmaceuticals, Ardsley, N.Y., 537 (1970).

In some embodiments, the nitric oxide releasing agent as provided by the present application may be administered in an therapeutically effective amount of about 0.0001 mg/kg to about 10 mg/kg (e.g., about 0.0001 mg/kg to about 10 mg/kg, about 0.005 mg/kg to about 10 mg/kg, about 0.01 mg/kg to about 10 mg/kg, about 0.02 mg/kg to about 10 mg/kg, about 0.05 mg/kg to about 10 mg/kg, about 0.1 mg/kg to about 10 mg/kg, about 0.15 mg/kg to about 10 mg/kg, about 0.2 mg/kg to about 10 mg/kg, about 0.25 mg/kg to about 10 mg/kg, about 0.3 mg/kg to about 10 mg/kg, about 0.35 mg/kg to about 10 mg/kg, about 0.4 mg/kg to about 10 mg/kg, about 0.45 mg/kg to about 10 mg/kg, about 0.5 mg/kg to about 10 mg/kg, about 0.55 mg/kg to about 10 mg/kg, about 0.6 mg/kg to about 10 mg/kg, about 0.65 mg/kg to about 10 mg/kg, about 0.7 mg/kg to about 10 mg/kg, about 0.75 mg/kg to about 10 mg/kg, about 0.8 mg/kg to about 10 mg/kg, about 0.85 mg/kg to about 10 mg/kg, about 0.9 mg/kg to about 10 mg/kg, about 0.95 mg/kg to about 10 mg/kg, about 1 mg/kg to about 10 mg/kg, about 2 mg/kg to about 10 mg/kg, about 5 mg/kg to about 10 mg/kg, about 6 mg/kg to about 10 mg/kg, about 8 mg/kg to about 10 mg/kg or about 9 mg/kg to about 10 mg/kg). In some embodiments, the nitric oxide releasing agent is administered in an amount of about 5 mg/kg or less. In some embodiments, the dosage is 1 mg/kg or less, 0.5 mg/kg or less, 0.1 mg/kg or less, 0.05 mg/kg or less or 0.01 mg/kg or less. A certain dosage may be divided into multiple doses, e.g., once per day, twice or more per day, once per week, once per two weeks, once per three weeks, once per month, or once per two or more months. In some embodiments, the dosage may vary over the treatment progress. For instance, in some embodiments, the initial dosage may be higher than the subsequent dosage. In some embodiments, the dosage may be adjusted in accordance with the response of the subject over the treatment progress. When improving the conditions of the subject, the nitric oxide releasing agent of the present invention may be administered in a maintenance dose. Then, the dose and/or the frequency of administration may be reduced to a level for maintaining the improved conditions when the symptoms are ameliorated to the desired level. In some embodiments, the agent may be administered at intervals depending on the conditions of disease in the subject.

In the medicament of the present application, the concentration of the nitric oxide releasing agent may be from about 0.0001% (w/w) to about 50% (w/w), for example, may be about 0.0001% (w/w) to about 90% (w/w), about 0.0001% (w/w) to about 80% (w/w), about 0.0001% (w/w) to about 70% (w/w), about 0.0001% (w)/w) to about 60% (w/w), about 0.0001% (w/w) to about 50% (w/w), about 0.0001% (w/w) to about 40% (w/w), about 0.0001% (w/w) to about 30% (w/w), about 0.0001% (w/w) to about 20% (w/w), about 0.0001% (w/w) to about 10% (w/w), from about 0.0001% (w/w) to about 5% (w/w), from about 0.0001% (w/w) to about 1% (w/w), from about 0.0001% (w/w) to about 0.5% (w/w), about 0.0001% (w/w) to about 0.1% (w/w), about 0.0001% (w/w) to about 0.05% (w/w), about 0.0001% (w/w) to about 0.01% (w/w), about 0.0001% (w/w) to about 0.005% (w/w), about 0.0001% (w/w) to about 0.005% (w/w) or about 0.0001% (w/w) to about 0.0001% (w/w).

The nitric oxide releasing agent as described in the present application may be administered in a manner well known in the art, e.g., by injection (e.g., subcutaneous, intraperitoneal, intraarticular, intraarterial, intrathecal, intrasternal, intrathecal, intralesional, intracranial, intramuscular, intracutaneous and intravenous injection or infusion) or non-injection (e.g., oral, nasal, sublingual, vaginal, rectal, or topical administration). The nitric oxide releasing agent as disclosed in the present application may be administered in a form of the pharmaceutical composition or kit of the present application.

In some embodiments, the administration of the nitric oxide releasing agent may be topical administration. The site of the topical administration is not the occurrence site of cancer or potential metastatic site of cancer. For example, the administration portion may not be the primary site of cancer. As another example, the administration portion may not be a metastatic site of cancer. For example, the metastatic site may comprise sites of cancer metastasis occurrence resulting from lymphatic metastasis, vascular metastasis, and/or implantative metastasis. In some embodiments, the transfer site may comprise bone, brain, liver, stomach, and/or lung. As another example, the administration portion may not be a recurrence site of cancer.

In some embodiments, the nitric oxide releasing agent may be administered transdermally.

In some embodiments, the nitric oxide releasing agent as described in the present invention may be administered together with an EGFR inhibitor. In some embodiments, the nitric oxide releasing agent is administered before, simultaneously with, or after the administration of an EGFR inhibitor to the subject. In some embodiments, the nitric oxide releasing agent may be separately administered from the EGFR inhibitor as a part of a multi-dose regimen. In other embodiments, the nitric oxide releasing agent may be simultaneously administered with the EGFR inhibitor. In the embodiments of simultaneous administration, these nitric oxide releasing agents may be a part of a single dosage form, which is mixed with the currently disclosed EGFR inhibitor to form a single composition. In some embodiments, these nitric oxide releasing agents may be approximately simultaneously administered with the EGFR inhibitor as a separate dose. When the EGFR inhibitor as disclosed in the present invention is simultaneously administered with the nitric oxide releasing agent, the nitric oxide releasing agent is administered in an dosage level of about 0.001-10% (e.g., about 0.005-10%, about 0.005-8%, about 0.01-10%, about 0.05-10%, about 0.1-10%, about 0.2-10%, about 0.3-10%, about 0.4-10%, about 0.5-10%, about 0.6-10%, about 0.7-10%, about 0.8-10%, about 0.9-10%, about 0.95-10%, about 1-10%, about 2-10%, about 3-10%, about 5-10%, about 6-10%, about 8-10% or about 9-10%) in relation to the total dosage. In the embodiments in which the nitric oxide releasing agent and the EGFR inhibitor are administered at intervals, the nitric oxide releasing agent may be separately administered before or after the administration of the EGFR inhibitor. The time intervals may be 1 min, 2 mins, 5 mins, 10 mins, 20 mins, 30 mins, 45 mins, 1 hr, 2 hrs, 3 hrs, 4 hrs, 5 hrs, 6 hrs, 12 hrs, 18 hrs, 1 day, 2 days, 3 days, 1 week, 2 weeks, 3 weeks, 1 month, 2 months, 3 months or longer.

In some embodiments, the EGFR inhibitor of the present invention may be administered in the same administration route as the nitric oxide releasing agent or administered in a different route. In some embodiments, the EGFR inhibitor is systemically administered or topically administered. In some embodiments, the EGFR inhibitor is administered in a manner other than transdermal administration, e.g., orally administered about once to about one to six times per day, or administered by continuous infusion. In some embodiments, the EGFR inhibitor of the present application may be systemically administered, while the nitric oxide releasing agent is topically administered. In some embodiments, the EGFR inhibitor of the present application may be intravenously administered, while the nitric oxide releasing agent may be transdermal administered. In some embodiments, the EGFR inhibitor of the present application may be oral administered, while the nitric oxide releasing agent may be transdermal administered.

The Nitric Oxide Releasing Agent Administered in Combination with Other Therapeutic Substances In some embodiments, the nitric oxide releasing agent as described in the present application may be administered together with one or more additional therapeutic agents. The phrase "administered in combination" or "administered together" as used herein further means that when the nitric oxide releasing agent is administered before or after the administration of an additional therapeutic substance, it is also deemed to be "administered in combination" with therapeutic substance, even if the nitric oxide releasing agent is administered in a manner different from the second substance. If possible, the additional therapeutic substance administered in combination with the nitric oxide releasing agent as disclosed in the present application may be administered with reference to the product specification of the additional therapeutic substance, or to the Physicians' Desk Reference, 57th Ed; Medical Economics Company, ISBN: 1563634457, Edition 57 (November, 2002), or to other methods well known in the art.

In some embodiments, the one or more additional therapeutic agents may be administered separately from the nitric oxide releasing agent of the present invention as a part of the multi-dose regimen (e.g., administering the nitric oxide releasing agent sequentially, e.g., administering the nitric oxide releasing agent in different overlapping regimens). In other embodiments, these therapeutic agents may be a part of a single dosage form, and mixed with the currently disclosed nitric oxide releasing agent to form a single composition. In another embodiment, these agents may be administered approximately simultaneously with the nitric oxide releasing agent in separate doses. When the nitric oxide releasing agent as disclosed in the present invention is simultaneously administered with one or more additional therapeutic agents, the nitric oxide releasing agent is administered in a dose level of about 1-99% (e.g., about 1-99%, about 1-95%, about 5-99%, about 10-99%, about 20-99%, about 30-99%, about 40-99%, about 50-99%, about 60-99%, about 70-99%, about 80-99%, about 90-99%, about 95-99%) in relation to the total dosage. In some embodiments, the one or more additional therapeutic agents may be a medicament for treating epithelial diseases.

Medicaments for treating epithelial diseases may comprise anti-inflammatory agents, analgesics, local anesthetics, antihistamines, preservatives, immuosuppressors, antihemorrhagic agents and/or a mixture thereof.

Anti-inflammatory agents may comprise ibuprofen, naproxen, indomethacin, meloxicam, paracetamol, methyl salicylate, monoethylene glycol salicylate, aspirin, mefenamic acid, flufenamic acid, indomethacin, diclofenac, alclofenac, diclofenac sodium, ketoprofen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, clobetasol propionate, betamethasone dipropionate, halobetasol propionate, diflorasone diacetate, fluocinonide, halcinonide, amcinonide, desoximetasone, triamcinolone, mometasone furoate, fluticasone propionate, betamethasone dipropionate, luticasone propionate, desonide, hydrocortisone pentanoate, prednicarbate, triamcinolone acetonide, fluocinoloneacetonide, hydroprednisolone, dexamethasone, hydrocortisone acetate, hydroprednisolone acetate, methylprednisolone, dexamethasone acetate, betamethasone, betamethasone pentanoate, flumetasone, fluorometholone, beclomethasone dipropionate and/or fluocinonide.

Analgesics may comprise alfentanil, benzocaine, buprenorphine, butorphanol, butamben, capsaicine, clonidine, codeine, dibucaine, enkephalin, fentanyl, hydrocodone, hydromorphone, indomethacin, lidocaine, levorphanol, meperidine, adanon, morphine, nicomorphine, opium, oxybuprocaine, oxycodone, oxymorphone, pentazocine, pramoxine, proparacaine, propoxyphene, proxymetacaine, sufentanil, tetracaine and/or tramadol.

Local anesthetics may comprise dibucaine hydrochloride, dibucaine, lidocaine hydrochloride, lidocaine, benzocaine, p-butyl aminobenzonic acid 2-(diethylamino)ethyl hydrochloride, procaine hydrochloride, tetracaine, tetracaine hydrochloride, chloroprocaine hydrochloride, hydroxyprocaine hydrochloride, mepivacaine, cocaine hydrochloride, piperocaine hydrochloride, dyclonine and/or dyclonine hydrochloride.

Antihistamines may comprise diphenhydramine hydrochloride, diphenhydramine salicylate, diphenhydramine, chlorpheniramine hydrochloride, chlorphenamine maleate, isothipendyl hydrochloride, tripelennamine hydrochloride, promethazine hydrochloride and/or methdilazine hydrochloride.

Preservatives may comprise alcohols, quaternary ammonium compounds, boric acid, chlorhexidine and chlorhexidine derivatives, iodine, phenols, terpenes, merthiolate, thymol, benzakonium chloride, benzethonium chloride, chlorhexidine, povidone-iodine, cetylpyridinium chloride, eugenol and/or trimethylammonium bromide.

Antihemorrhagic agents may comprise thrombin, vitamin Kl, protamine sulfate, aminocaproic acid, tranexamic acid, carbazochrome, sodium carbazochrome sulfonate, rutin and/or hesperidin.

Medicament, Pharmaceutical Composition or Kit Containing Nitric Oxide Releasing Agent In some embodiments, the nitric oxide releasing agent may be administered partly in medicament or pharmaceutical composition.

In some embodiments, the medicament may comprise a nitric oxide releasing agent and one or more pharmaceutically acceptable carriers.

In some embodiments, the pharmaceutical composition or kit may comprise 1) an EGFR inhibitor; and 2) a nitric oxide releasing agent. In some embodiments, the EGFR inhibitor and the nitric oxide releasing agent are not mixed with each other. For example, the EGFR inhibitor can be present separately from the nitric oxide releasing agent in a separate container. For example, the EGFR inhibitor can be dispensed in one reagent bottle and the nitric oxide release agent can be dispensed in another reagent bottle.

The term "pharmaceutically acceptable" as used herein generally refers to the compounds, materials, compositions and/or dosage forms, which are adapted, within reasonable medical judgment, to contact the tissues of human and animals without excess of toxicity, irritation, allergic reaction, or other problems or complications, and have a reasonable ratio of benefit to risk. In some embodiments, the pharmaceutically acceptable compounds, materials, compositions and/or dosage forms refer to those for use in animals (especially, humans) as approved by a management institution (such as, the U.S. Food and Drug Administration (FDA), China's State Food and Drug Administration (CFDA), or European Medicines Agency (EMA)) or listed in commonly accepted pharmacopoeias (e.g., United States Pharmacopeia (USP), Chinese Pharmacopoeia or European Pharmacopoeia).

The pharmaceutically acceptable excipients for use in the medicament, pharmaceutical composition or kit of the present application may comprise but are not limited to, e.g., pharmaceutically acceptable liquids, gels or solid vehicles, aqueous mediums (e.g., sodium chloride injection, Ringer's injection, isotonic dextrose injection, sterile aqueous injection, dextrose or lactated Ringer's injection), non-aqueous mediums (e.g., vegetable-derived non-volatile oils, cottonseed oil, corn oil, sesame oil or peanut oil), antimicrobial substances, isotonic substances (e.g., sodium chloride or dextrose), buffer solutions (e.g., phosphate buffer or citrate buffer), anti-oxidative agents (e.g., sodium disulfate), anesthetics (e.g., procaine hydrochloride), suspending/dispersing agents (e.g., sodium carboxymethylcellulose, hydroxypropylmethylcellulose or polyvinylpyrrolidone), chelating agents (e.g., EDTA (ethylene diamine tetraacetic acid) or EGTA (ethylene glycol bi(2-aminoethylether)tetraacetic acid)), emulsifiers (e.g., polysorbate 80 (Tween-80)), diluents, adjuvants, excipients, non-toxic auxiliary substances, other ingredients well known in the art, or any combination of the foregoing. Suitable ingredients may comprise, e.g., fillers, adhesives, disintegrating agents, buffers, preservatives, lubricants, flavoring agents, thickeners, colorants or emulsifying agents.

In some embodiments, the medicament or the nitric oxide releasing agent may be an oral formulation. The oral formulations may comprise, but are not limited to, capsules, microcapsules, pills, tablets, troches (suitable for use with flavorous base, generally including sucrose and gum arabic or tragacanth), powders, particles, aqueous or non-aqueous solution or suspension, water-in-oil or oil-in-water emulsions, elixirs or syrups, pastilles (suitable for use with inert base, such as, gelatin, glycerol, sucrose or gum arabic) and/or mouthwashes and their analogues.

Oral solid formulations (e.g., capsules, tablets, pills, dragees, powders, or particles, etc.) may comprise the active substances and one or more pharmaceutically acceptable excipients, such as, sodium citrate or dicalcium phosphate, and/or the following substances: (1) fillers or supplements, e.g., starch, lactose, sucrose, dextrose, mannitol and/or silicic acid; (2) adhesives, e.g., carboxymethylcellulose, alginate, gelation, polyvinylpyrrolidone, sucrose and/or gum arabic; (3) wetting agents, e.g., glycerol; (4) disintegrating agents, e.g., agar, calcium carbonate, potato or tapioca starch, alginic acid, certain silicates and/or sodium carbonate; (5) blocker solution, e.g., paraffin; (6) absorption accelerator, e.g., quaternary ammonium compounds; (7) lubricants, e.g., acetyl alcohol and/or glycerol monostearate; (8) absorbers, e.g., kaolins and/or bentonites; (9) glidants, e.g., talc, calcium stearate, magnesium stearate, solid PEG, sodium lauryl sulfate and a mixture thereof; and (10) colorants.

Oral liquid formulations may comprise pharmaceutically acceptable emulsions, microemulsions, solutions, suspensions, syrups, and elixirs, etc. In addition to the active substances, the liquid dosage forms may further comprise common inert diluents, e.g., water or other solvents, solubilizers and emulsifiers, such as, ethanol, isopropyl alcohol, ethyl carbonate, ethyl acetate, benzyl alcohol, benzyl benzoate, propylene glycol, 1,3-butylene glycol, oils (especially, cottonseed oil, peanut oil, corn oil, olive oil, castor oil, and sesame oil), glycerol, tetrahydrofurfuryl alcohol, polyethylene glycol and sorbitan fatty acid esters, and a mixture of two or more of the foregoing. In addition to the inert diluents, the oral liquid formulations may further comprise adjuvants, e.g., wetting agents, emulsifiers, suspending agents, sweeteners, flavoring agents, pigments, fragrances, or preservatives.

In some embodiments, the medicament or the nitric oxide releasing agent may be an injectable formulation. The injectable formulations may comprise sterile aqueous solutions, dispersions, suspensions, or emulsions. In all cases, the injectable formulation should be sterile and should be a liquid to convenient injection. It should be stable under the production and storage conditions, and resistant to microbial contamination (e.g., bacteria and fungi). The carrier may be a solvent or dispersing medium, including, e.g., water, ethanol, polyhydroxy compounds (e.g., glycerol, propylene glycol or liquid polyethylene glycol, etc.) or a suitable mixture thereof and/or vegetable oil. The injectable formulation should have a suitable fluidity, which may be maintained by a variety of manners, e.g., by using a coating like lecithin, etc., by using surfactants, and the like. The resistance to microbial contamination may be achieved by adding various antibacterial and antifungal agents (e.g., p-hydroxylbenzoate, chlorbutanol, phenol, sorbic acid or thiomersalate, etc.).

In some embodiments, the medicament or the nitric oxide releasing agent of the present application may be used for topically oral administration. Suitable formulations for topically oral administration may comprise troches comprising the nitric oxide releasing agent in a flavorful base like sucrose and gum arabic or tragacanthin, troches comprising the nitric oxide releasing agent in an inert base like gelation and glycerol or sucrose and gum arabic, and mouthwashes comprising the nitric oxide releasing agent in a suitable liquid carrier. In some embodiments, the nitric oxide releasing agent may be oral or nasal spray formulations. The spray formulations may comprise, but not limited to, aqueous aerosols, non-aqueous suspensions, liposomes or solid particles, or the like. The aqueous aerosols may be produced by formulating the aqueous solution or suspension of the nitric oxide releasing agent with conventional pharmaceutically acceptable excipients and stabilizers. The carriers and stabilizers may vary depending the requirements of the particular compound, but generally comprise nonionic surfactants (Tweens, or polyethylene glycol), oleic acid, lecithin, amino acid (e.g., glycine), buffers, salts, sugars or sugar alcohol. The aerosols may generally be prepared from isotonic solutions, and may be delivered via a sprayer.

In the present application, the medicament or the nitric oxide releasing agent may be prepared for transdermal administration. In the present application, the medicament or the nitric oxide releasing agent may be formulated to be suitable for topical administration. In some embodiments, the medicament or the nitric oxide release agent may be prepared for topical skin application. For example, in the present application, the medicament or the nitric oxide releasing agent may be prepared as an ointment. For example, by suspending or dissolving the nitric oxide releasing agent in a mixture of one or more of the followings: mineral oils, liquid Vaseline, white Vaseline, propylene glycol, polyoxymethylene polyoxypropylene compound, emulsified wax and water. The nitric oxide releasing agent may also be formulated into a suitable lotion or cream, and suspended or dissolved in a mixture of one or more of the followings: mineral oils, sorbitan monostearate, polyethylene glycol, liquid paraffin, polysorbate 60, cetyl ester alcohol, 2-octyl lauryl alcohol, benzyl alcohol and water.

In the medicament, pharmaceutical composition or kit of the present application, the concentration of the nitric oxide releasing agent may be from about 0.0001% (w/w) to about 50% (w/w), for example, may be from about 0.0001% (w/w) to about 90% (w/w), from about 0.0001% (w/w) to about 80% (w/w), from about 0.0001% (w/w) to about 70% (w/w), from about 0.0001% (w/w) to about 60% (w/w), from about 0.0001% (w/w) to about 50% (w/w), from about 0.0001% (w/w) to about 40% (w/w), from about 0.0001% (w/w) to about 30% (w/w), from about 0.0001% (w/w) to about 20% (w/w), from about 0.0001% (w/w) to about 10% (w/w), from about 0.0001% (w/w) to about 5% (w/w), from about 0.0001% (w/w) to about 1% (w/w), from about 0.0001% (w/w) to about 0.5% (w/w), from about 0.0001% (w/w) to about 0.1% (w/w), from about 0.0001% (w/w) to about 0.05% (w/w), from about 0.0001% (w/w) to about 0.01% (w/w), from about 0.0001% (w/w) to about 0.005% (w/w), from about 0.0001% (w/w) to about 0.005% (w)/w) or from about 0.0001% (w/w) to about 0.0001% (w/w).

In the pharmaceutical composition or kit of the present application, the nitric oxide releasing agent in 2) may prevent or treat the disease or disorder caused by the EGFR inhibitor in 1).

In the pharmaceutical composition or kit of the present application, the nitric oxide releasing agent in 2) does not substantially affect the therapeutic effect of the EGFR inhibitor in 1).

In the present application, the term "substantially unaffected" may mean the use of the nitric oxide releasing agent in 2) of the pharmaceutical composition or kit as compared to the therapeutic effect of using the EGFR inhibitor alone, the therapeutic effect of the EGFR inhibitor in 1) is comparable or does not produce a significant disadvantage. For example, for any subject, the nitric oxide releasing agent in 2) of the pharmaeutical composition or kit and the method of 1) are used as compared to the therapeutic effect of using the EGFR inhibitor alone, the extent of tumor volume reduction caused by the EGFR inhibitor is the same, or the degree of reduction is not less than about 5%, not less than about 4%, not less than about 3%, not less than about 2%, not less than about 1%, not less than about 0.5%, not less than about 0.1%, not less than about 0.01%, not less than about 0.001% or less.

In the pharmaceutical composition or kit of the present application, the nitric oxide releasing agent in 2) may be administered before, simultaneously or after administration of the EGFR inhibitor in 1).

Use of Treatment

One aspect of the present application provides the use of the nitric oxide releasing agent in preparation of a medicament adapted to prevent or treat EGFR inhibition-associated epithelial diseases.

Another aspect of the present application provides a nitric oxide releasing agent, which is used for preventing or treating EGFR-inhibition associated diseases or illness (e.g., EGFR-inhibition associated epithelial diseases).

In another aspect, the present application provides a method of preventing or treating an EGFR-inhibition associated disease or disorder in a subject (e.g., an EGFR-inhibition associated epithelial disease), comprising administering an effective amount of a nitric oxide releasing agent for preventing or treating to a subject. In some embodiments, the subject may comprise a human or a non-human animal. For example, the non-human animal may comprise an animal selected from the group consisting of a monkey, a chicken, a goose, a cat, a dog, a mouse, and a rat. In some embodiments, the inhibition of the EGFR may be caused by administration of an EGFR INHIBITOR TO THE SUBJECT.

EXAMPLES

Example 1

Synthesis of S-Nitrosothiolsilica Nanosphere

A mixed solution of 4 ml of (3-mercaptopropyl) trimethoxysilane and 2 ml of tetraethyl orthosilicate was injected via an injection pump to a mixed solution of 30 ml of deionized water, 30 ml of ethanol and 30 ml of ammonia water at a rate of 0.5 ml/min. During injection, the reaction mixture was kept at 0° C. After completion of injection, the reaction mixture was stirred at room temperature for 2.5 hrs, and then centrifuged at 4000 rpm for 8 mins. The precipitates were washed for one time with 100 ml of ice water and 100 ml of ethanol, respectively, and dried under vacuum to give thiolated silica nanospheres.

150 mg thiolated silica nanosphere was dispersed in 4 ml of methanol, and cooled to 0° C. A mixed solution of 2 ml of 1 M sodium nitrite and 1 mM diethyltriaminepentaacetic acid was added under constant stirring, and then 2 ml of 5 M aqueous solution of hydrochloric acid was added. The reaction mixture was stirred in the dark at 0° C. for 2.5 hrs, centrifuged at 4° C. at 4000 rpm for 5 mins. The precipitates were washed for one time with 30 ml of 1 mM aqueous solution of diethyltriaminepentaacetic acid at 4° C. and 30 ml of methanol at 4° C., respectively, and centrifuged again for collecting the solid. In the dark and at a temperature below −30° C., the solid was dried under vacuum for 30 mins to give the dried final product, which was stored at −20° C. for use.

The final product was dissolved in a PBS buffer solution of pH=7.4, and it was measured by using ZS90 Type Particle Size and Zeta Potential Analyzer that the hydrodynamic radius of the product was 423 nm and the polydispersity index was 0.061. The UV-visible spectrum of the solution (as measured by using Thermo Fisher EV300 Type UV spectrophotometer) has a characteristic absorption peak at 330 nm. Under the conditions of 200 W light for 5 hrs, the NO storage was characterized by the total amount of the released nitric oxide as detected by Beyotime NO assay kit (Griess Method, purchased from Shanghai Beyotime Biotechnology Inc.). The NO storage of the final product was measured to be 1.87±0.55 μmol/mg.

Example 2

Synthesis of S-nitrosoethanedithiolchitin 2 g of chitin and 5 g of lithium chloride were dispersed in 50 ml of dimethylacetamide, and 20 ml of N,N-diisopropylethylamine was added at 0° C. 20 g of p-toluenesulfonyl chloride was dissolved in 20 ml of dimethylacetamide, and the resultant mixture was added into the chitin-containing solution as prepared above. The mixed solution was stirred at 4° C. for 20 hrs, and then poured into 300 ml of acetone for precipitation and filtration. The precipitates were washed for one time with 300 ml of methanol, 150 ml of DI water and 300 ml of acetone, respectively, and then dried under vacuum to give p-tosylated chitin.

1 g of p-tosylated chitin and 2.5 g of lithium chloride were dispersed into 40 ml of dimethylacetamide, and then 3 ml of N,N-diisopropylethylamine and 1.5 ml of 1,2-ethanedithiol were added. The mixed solution was stirred at 60° C. under nitrogen for 24 hrs, and then poured into 400 ml of acetone for precipitation and filtration. The precipitates were washed with once 400 ml of methanol and 400 ml of acetone, respectively, dried under vacuum, and then dispersed into a 25 ml solution of 10 mM 1,4-dithiothreitol and N,N-diisopropylethylamine in dimethylacetamide. The reaction mixture was stirred at room temperature for 1 hr, and filtered. The precipitates were washed for one time with 400 ml of methanol and 400 ml of acetone, respectively, and dried under vacuum to give thiolated chitin compound. 200 mg thiolated chitin compound was dispersed into a 5 ml mixed solution of dimethylacetamide/methanol (at a volume ratio of 3/1), and 1 ml of tert-butyl nitrite was added and stirred at room temperature for 12 hrs. Then, the mixed solution was added in to 100 ml of methanol and stirred for 30 mins, filtered, and dried under vacuum to give the final product.

The infrared spectroscopy of the final product (as detected by Nicolet 6700 Type infrared spectrometer) has main absorption peaks (wave numbers) of 3600-3200, 3285, 1652, 1537, and 1028. The diffuse reflectance UV-visible spectrum thereof (as detected by using Thermo Fisher EV300 Type UV spectrophotometer) shows a characteristic absorption peak at 549 nm. Under the conditions of 200 W light for 5 hrs, the NO storage was characterized by the total amount of the released nitric oxide as detected by Beyotime NO assay kit (Griess Method, purchased from Shanghai Beyotime Biotechnology Inc.). The NO storage of the final product was measured to be 0.37±0.08 μmol/mg.

Example 3

Synthesis of Oligo-Propylenediamine Grafted Chitosan NONOate

250 μL of 2-methylaziridine was mixed with 300 μL of 1 M aqueous solution of hydrochloride, and the mixture was added dropwise into 10 ml of 20 mg/mL chitosan. The mixed solution was stirred at room temperature for 4 days and at 78° C. for 20 hrs, and then poured into 300 ml of acetone for precipitation and centrifugation. The precipitates were washes twice with methanol, and dried under vacuum to give secondary amine modified chitosan. H NMR spectroscopy (by using Bruker Avance III Type NMR spectrometer, 400 MHz, $CD_3OD$) shows peaks at 0.8-1.1, 1.9, 2.3-2.7, 3.3-4.0, and 4.4.

50 mg secondary amine modified chitosan was dissolved in a mixed solution of 1 mL of water and 3 mL of methanol, and the mixed solution was added to Parr swing hydrogenator, together with 100 μL of 6 M solution of sodium methoxide. The hydrogenator was repeatedly purged with high purity nitrogen to remove oxygen, filled with gaseous nitric oxide, and kept at 10 atm at room temperature for 4 days for reaction. After completion of reaction, the reaction vessel was repeatedly purged with high purity nitrogen to remove unreacted nitric oxide. Then, the reaction mixture was added into 300 mL of acetone for precipitation, centrifuged to collect the precipitates, and dried under vacuum to give the final product (including diazeniumdiolate), which was stored at −20° C. for next use.

The infrared spectrum of the final product (as detected by using Nicolet 6700 Type infrared spectrometer) comprises main absorption peaks (wave numbers) of 3600-3200, 3285, 1650, 1587, 1284, and 1059. The UV-visible spectrum thereof (as detected by using Thermo Fisher EV300 Type UV spectrophotometer) comprises a characteristic absorption peak at 252 nm. The sample was dissolved in a PBS solution, and detected by Beyotime NO assay kit (Griess Method) for the total NO releasing amount, so as to determine that the NO storage of the sample which was 0.77±0.11 μmol/mL.

Example 4-46

Proliferative Toxicity of EGFR Inhibitor on Skin Cells HaCaT and Ameliorating Effect of Nitric Oxide Releasing Agents The cultured skin cell HaCaT were digested, counted, and seeded in a 96-well plate with 5000-10000 cells per well. After the cells were attached, the supernatant was discarded. The wells were divided to the blank control group, the EGFR inhibitor group, the EGFR inhibitor+nitric oxide releasing agent group and the blank solvent control group. The EGFR inhibitor group: 100 μL of the EGFR inhibitor solution was added (the final concentration was shown in Table 2; Cetuximab was in an aqueous solution, besides which each of other EGFR inhibitors were in a solution containing DMSO); the EGFR inhibitor+nitric oxide releasing agent group: the EGFR inhibitor solution and the nitric oxide releasing agent solution were added (the final concentration of the EGFR inhibitor and nitric oxide releasing agent were shown in Table 2, and depending on the solubility of the nitric oxide releasing agent, the nitric oxide releasing agent solution was an ethanol solution or an aqueous solution); the blank control group: except the normal replacement of the medium, no additional solution was added; a plurality of blank solvent control groups: an equal volume of the same type of solvent as the corresponding EGFR inhibitor group or the EGFR inhibitor+nitric oxide releasing agent was added. The blank solvent control groups were used for data correction, so as to eliminate the effect of solvent to the result in the EGFR inhibitor group and the EGFR inhibitor+nitric oxide releasing agent group. After additional culture for 48 hrs, the survival rate of cells was measured by Cell Counting Kit-8 (CCK-8) assay kit (C0037, purchased from Shanghai Beyotime Biotechnology Inc.) to calculate the proliferative toxicity of the EGFR inhibitor to cells and the ameliorating effect of the nitric oxide releasing agent to the proliferative toxicity. GraphPad Prism 6.0 Software and t-test were used to carry out a statistic analysis of the results and plot a graph.

Figure 4:
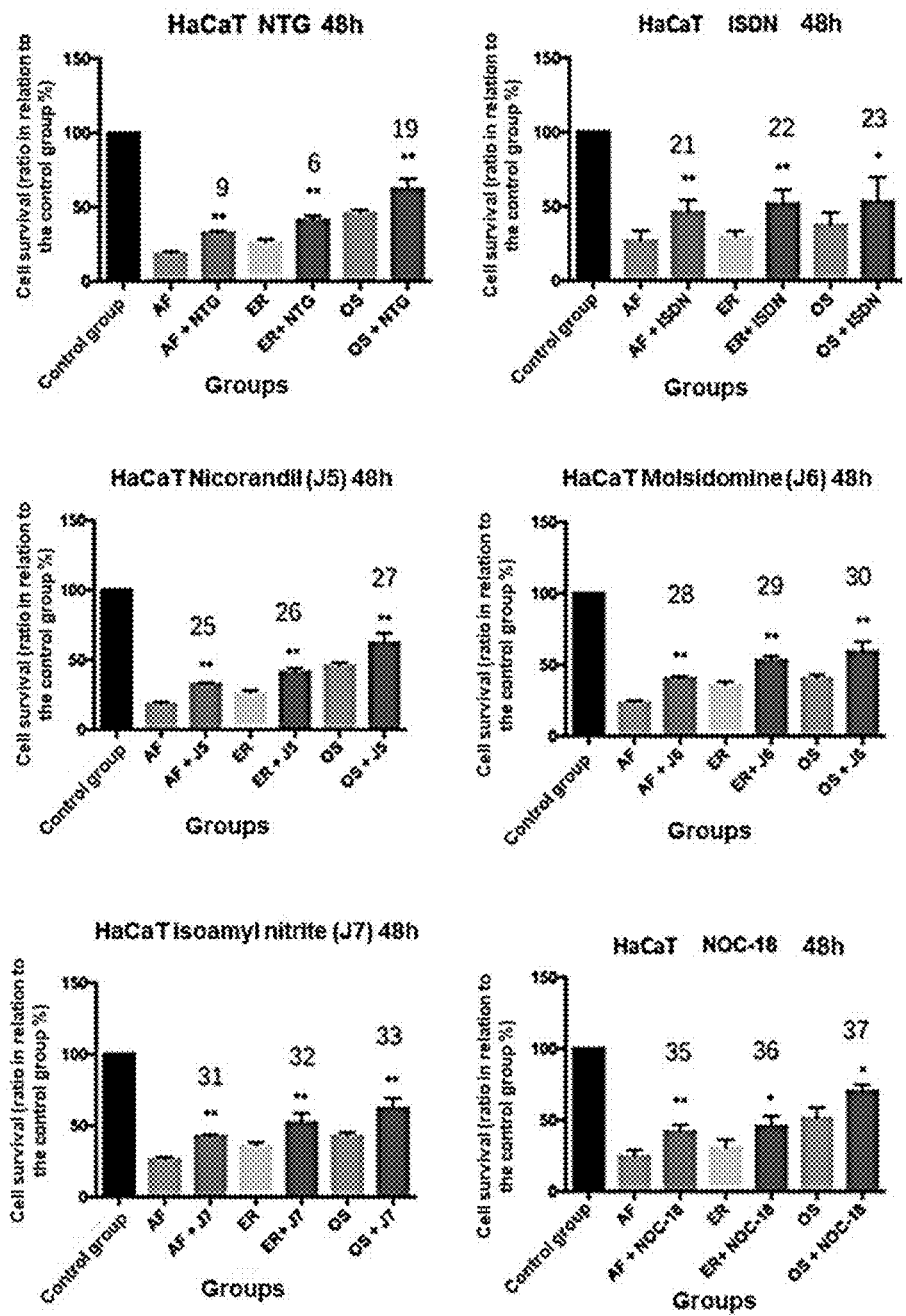
FIG. 4 depicts exemplary results of cell proliferation toxicity at 48 hours after simultaneous administration of an EGFR inhibitor and a nitric oxide releasing agent to HaCaT cells, as measured in accordance with the CCK-8 method (including the data of Examples 6, 9, 19, 21-23, 25-27, 28-33 and 35-37). In the figure, NTG represents nitroglycerin, ISDN represents isosorbide dinitrate, AF represents Afatinib, ER represents Erlotinib, OS represents Osimertinib. Among those, **represents $P<0.01$, indicating a significant difference as compared with the control group which is administered with the EGFR inhibitor alone; *represents $P<0.05$, indicating a significant difference as compared with the control group which is administered with the EGFR inhibitor alone, as statistically determined by using t-test. The numbers above the bar chart represent the serial numbers of the examples.

Table 2 lists various combinations of EGFR inhibitors and nitric oxide releasing agents and the corresponding experimental results (wherein the data in the cell survival rate column represent the percentages of viable cells increased by the corresponding the EGFR inhibitor+nitric oxide releasing agent group as compared to the EGFR inhibitor group). FIG. 4 listed several typical experimental results.

TABLE 2

Experimental Conditions and Results of Example 4-46

| Example No. | EGFR inhibitor | Final Concentration | Classification | Nitric Oxide Releasing Agent | Final Concentration | Cell Survival Rate |
|---|---|---|---|---|---|---|
| 4 | Cetuximab | 100-200 μg/mL | Monoclonal antibody | Nitroglycerin (NTG) | 200 μM | Increased by 35-45% |
| 5 | Gefitinib | 10 μM | The first generation EGFR small molecule inhibitor | | | Increased by 65-75% |
| 6 | Erlotinib | 10 μM | The first generation EGFR small molecule inhibitor | | | Increased by 65-75% |
| 7 | Icotinib | 10 μM | The first generation EGFR small molecule inhibitor | | | Increased by 65-75% |
| 8 | Sapitinib | 10 μM | The first generation EGFR small molecule inhibitor | | | Increased by 55-65% |
| 9 | Afatinib | 5 μM | The second generation EGFR small molecule inhibitor | | | Increased by 85-95% |
| 10 | Lapatinib | 10 μM | The second generation EGFR small molecule inhibitor | | | Increased by 55-65% |
| 11 | Vandetanib | 10 μM | The second generation EGFR small molecule inhibitor | | | Increased by 55-65% |
| 12 | Poziotinib | 10 μM | The second generation EGFR small molecule inhibitor | | | Increased by 55-65% |
| 13 | Neratinib | 10 μM | The second generation EGFR small molecule inhibitor | | | Increased by 65-75% |

TABLE 2-continued

Experimental Conditions and Results of Example 4-46

| Example No. | EGFR inhibitor | Final Concentration | Classification | Nitric Oxide Releasing Agent | Final Concentration | Cell Survival Rate |
|---|---|---|---|---|---|---|
| 14 | Canertinib | 10 μM | The second generation EGFR small molecule inhibitor | | | Increased by 55-65% |
| 15 | Varlitinib | 10 μM | The second generation EGFR small molecule inhibitor | | | Increased by 35-45% |
| 16 | Nazartinib | 10 μM | The third generation EGFR small molecule inhibitor | | | Increased by 55-65% |
| 17 | Rociletinib | 10 μM | The third generation EGFR small molecule inhibitor | | | Increased by 65-75% |
| 18 | Olmutinib | 10 μM | The third generation EGFR small molecule inhibitor | | | Increased by 35-45% |
| 19 | Osimertinib | 20 μM | The third generation EGFR small molecule inhibitor | | | Increased by 35-45% |
| 20 | EAI045 | 20 μM | The fourth generation EGFR small molecule inhibitor | | | Increased by 65-75% |
| 21 | Erlotinib | 10 μM | The first generation EGFR small molecule inhibitor | Isosorbide dinitrate (ISDN) | 400 μM | Increased by 75-85% |
| 22 | Afatinib | 5 μM | The second generation EGFR small molecule inhibitor | | | Increased by 85-95% |
| 23 | Osimertinib | 20 μM | The third generation EGFR small molecule inhibitor | | | Increased by 35-45% |
| 24 | Cetuximab | 100-200 μg/mL | Monoclonal antibody | | | Increased by 45-55% |
| 25 | Erlotinib | 10 μM | The first generation EGFR small molecule inhibitor | Nicorandil (J5) | 200 μM | Increased by 85-95% |
| 26 | Afatinib | 5 μM | The second generation EGFR small molecule inhibitor | | | Increased by 65-75% |
| 27 | Osimertinib | 20 μM | The third generation EGFR small molecule inhibitor | | | Increased by 30-40% |
| 28 | Erlotinib | 10 μM | The first generation EGFR small molecule inhibitor | Molsidomine (J6) | 200 μM | Increased by 75-85% |
| 29 | Afatinib | 5 μM | The second generation EGFR small molecule inhibitor | | | Increased by 35-45% |
| 30 | Osimertinib | 20 μM | The third generation EGFR small molecule inhibitor | | | Increased by 35-45% |
| 31 | Erlotinib | 10 μM | The first generation EGFR small molecule inhibitor | Isoamyl nitrite (J7) | 200 μM | Increased by 75-85% |
| 32 | Afatinib | 5 μM | The second generation EGFR small molecule inhibitor | | | Increased by 35-45% |
| 33 | Osimertinib | 20 μM | The third generation EGFR small molecule inhibitor | | | Increased by 35-45% |
| 34 | Cetuximab | 100-200 μg/mL | Monoclonal antibody | | | Increased by 35-45% |
| 35 | Erlotinib | 10 μM | The first generation EGFR small molecule inhibitor | NOC-18 | 200 μM | Increased by 75-85% |

TABLE 2-continued

Experimental Conditions and Results of Example 4-46

| Example No. | EGFR inhibitor | Final Concentration | Classification | Nitric Oxide Releasing Agent | Final Concentration | Cell Survival Rate |
|---|---|---|---|---|---|---|
| 36 | Afatinib | 5 μM | The second generation EGFR small molecule inhibitor | | | Increased by 35-45% |
| 37 | Osimertinib | 20 μM | The third generation EGFR small molecule inhibitor | | | Increased by 25-35% |
| 38 | Cetuximab | 100-200 μg/mL | Monoclonal antibody | | | Increased by 45-55% |
| 39 | Erlotinib | 10 μM | The first generation EGFR small molecule inhibitor | S-nitrosothiolsilica nanosphere | 0.30 mg/mL | Increased by 45-55% |
| 40 | Afatinib | 5 μM | The second generation EGFR small molecule inhibitor | | | |
| 41 | Osimertinib | 20 μM | The third generation EGFR small molecule inhibitor | | | |
| 42 | Cetuximab | 100-200 μg/mL | Monoclonal antibody | | | |
| 43 | Erlotinib | 10 μM | The first generation EGFR small molecule inhibitor | Oligomeric propanediamine-grafted chitosan NONOate | 1.80 mg/mL | Increased by 45-55% |
| 44 | Afatinib | 5 μM | The second generation EGFR small molecule inhibitor | | | |
| 45 | Osimertinib | 20 μM | The third generation EGFRs mall molecule inhibitor | | | |
| 46 | Cetuximab | 100-200 μg/mL | Monoclonal antibody | | | |

It can be concluded from the results in Table 2 and FIG. 4 that the EGFR inhibitor has a proliferative toxicity to skin cells HaCaT, while the nitric oxide releasing agent produces a significant ameliorating effect to the proliferative toxicity caused by the EGFR inhibitor.

Example 47-58

Proliferative Toxicity of EGFR Inhibitor to Small Intestine Epithelial Cell FHs 74 Int and Ameliorating Effect of Nitric Oxide Releasing Agent The cultured small intestine epithelial cells FHs 74 Int were digested, counted, and seeded to a 96-well plate with 5000-10000 cells per well. After the cells were attached, the supernatant was discarded. The wells were divided to the blank control group, the EGFR inhibitor group, the EGFR inhibitor+nitric oxide releasing agent group and blank solvent control group.

EGFR inhibitor group: 100 μL of the EGFR inhibitor solution was added (the final concentration was listed in Table 3, all the EGFR inhibitor solution are DMSO solution); the EGFR inhibitor+nitric oxide releasing agent group: the EGFR inhibitor solution and the nitric oxide releasing agent solution were added (the final concentrations of the EGFR inhibitor and the nitric oxide releasing agent were listed in Table 3, and depending on the solubility of the nitric oxide releasing agents, the nitric oxide releasing agent solution was ethanol solution or aqueous solution); the blank control group: except the normal replacement of medium, no additional solution was added; a plurality of blank solvent control group: an equal volume of the same type of solvent as the corresponding EGFR inhibitor group or the EGFR inhibitor+nitric oxide releasing agent group was added. The blank solvent control group was used for data correction to eliminate the effect of solvent to the result in the EGFR inhibitor group and the EGFR inhibitor+nitric oxide releasing agent group. After additional 48 hrs of culture, the survival rate of cells was determined by Cell Counting Kit-8 (CCK-8) assay kit (C0037, Shanghai Beyotime Biotechnology Inc., Beyotime Biotechnology), to calculate the proliferative toxicity of the EGFR inhibitor to cells and the ameliorating effect of the nitric oxide releasing agent to the proliferative toxicity. GraphPad Prism 6.0 Software and t-test were used to carry out a statistic analysis of the results and plot a graph.

Figure 5:
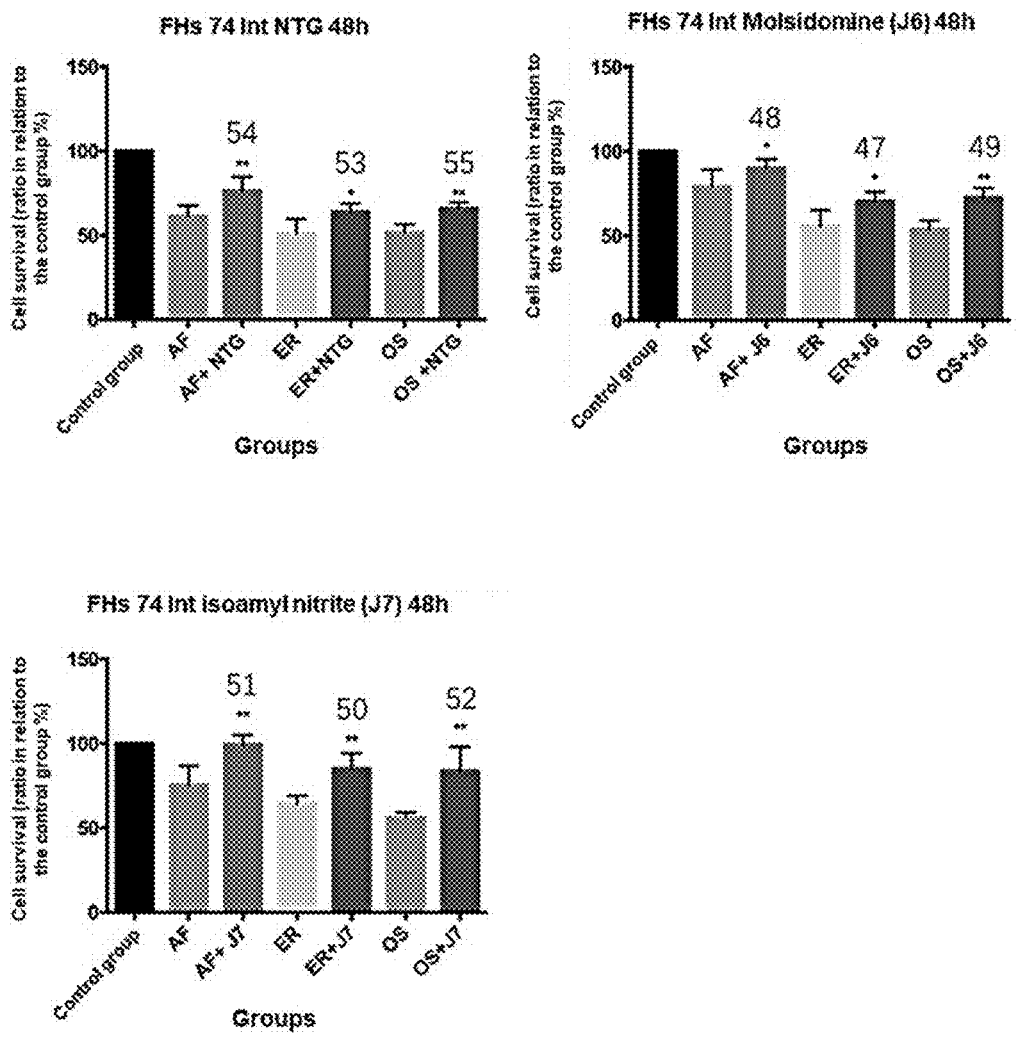
FIG. 5 depicts exemplary results of cell proliferation toxicity at 48 hours after simultaneous administration of an EGFR inhibitor and a nitric oxide releasing agent to FHs 74 Int cells, as measured in accordance with CCK-8 method (including the data of Examples 47-55). In the figure, NTG represents nitroglycerin, AF represents Afatinib, ER represents Erlotinib, OS represents Osimertinib. Among those, **represents $P<0.01$, indicating a significant difference as compared with the control group which is administered with the EGFR inhibitor alone; *represents $P<0.05$, indicating a significant difference as compared with the control group which is administered with the EGFR inhibitor alone, as statistically determined by using t-test. The numbers above the bar chart represent the serial numbers of the examples.

Table 3 lists various combinations of EGFR inhibitors and nitric oxide releasing agents and the corresponding experimental results (wherein the data in the cell survival rate column represent the percentages of viable cells increased by the corresponding the EGFR inhibitor+nitric oxide releasing agent group as compared to the EGFR inhibitor group). FIG. 5 lists several typical experimental results.

TABLE 3

Experimental Conditions and Results of Example 47-58

| Example No. | EGFR inhibitor | Final Concentration | Classification | Nitric Oxide Releasing Agent | Final Concentration | Cell Survival Rate |
|---|---|---|---|---|---|---|
| 47 | Erlotinib | 10 µM | The first generation EGFR small molecule inhibitor | Molsidomine (J6) | 200 µM | Increased by 15%-35% |
| 48 | Afatinib | 5 µM | The second generation EGFR small molecule inhibitor | | | |
| 49 | Osimertinib | 20 µM | The third generation EGFR small molecule inhibitor | | | |
| 50 | Erlotinib | 10 µM | The first generation EGFR small molecule inhibitor | Isoamyl nitrite (J7) | 200 µM | Increased by 25%-35% |
| 51 | Afatinib | 5 µM | The second generation EGFR small molecule inhibitor | | | |
| 52 | Osimertinib | 20 µM | The third generation EGFR small molecule inhibitor | | | |
| 53 | Erlotinib | 10 µM | The first generation EGFR small molecule inhibitor | Nitroglycerin (NTG) | 200 µM | Increased by 15%-35% |
| 54 | Afatinib | 5 µM | The second generation EGFR small molecule inhibitor | | | |
| 55 | Osimertinib | 20 µM | The third generation EGFR small molecule inhibitor | | | |
| 56 | Erlotinib | 10 µM | The first generation EGFR small molecule inhibitor | S-nitrosoethane-dithiolchitin | 0.30 mg/mL | Increased by 15-20% |
| 57 | Afatinib | 5 µM | The second generation EGFR small molecule inhibitor | | | |
| 58 | Osimertinib | 20 µM | The third generation EGFR small molecule inhibitor | | | |

It can be concluded from the results in Table 3 and FIG. 5 that the EGFR inhibitor has a proliferative toxicity to the small intestine epithelial cells FHs 74 Int, and the nitric oxide releasing agent produces a significant ameliorating effect to the proliferative toxicity caused by the EGFR inhibitor.

Example 59-70

Proliferative Toxicity of EGFR Inhibitor on Human Oral Keratinocytes (HOK) and Ameliorating Effect of Nitric Oxide Releasing Agent The cultured Human Oral Keratinocytes (HOK) were digested, counted, and seeded to a 96-well plate with 5000-10000 cells per well. After the cells were attached, the supernatant was discarded. The wells were divided to the blank control group, the EGFR inhibitor group, the EGFR inhibitor+nitric oxide releasing agent group and blank solvent control group. EGFR inhibitor group: 100 µL of the EGFR inhibitor solution was added (the final concentration was listed in Table 4, all the EGFR inhibitor solution that are DMSO solution); the EGFR inhibitor+nitric oxide releasing agent group: the EGFR inhibitor solution and the nitric oxide releasing agent solution were added (the final concentrations of the EGFR inhibitor and the nitric oxide releasing agent were listed in Table 4, and depending on the solubility of the nitric oxide releasing agents, the nitric oxide releasing agent solution was ethanol solution or aqueous solution); the blank control group: except the normal replacement of medium, no additional solution was added; a plurality of blank solvent control group: an equal volume of the same type of solvent as the corresponding EGFR inhibitor group or the EGFR inhibitor+nitric oxide releasing agent group was added. The blank solvent control group was used for data correction to eliminate the effect of solvent to the result in the EGFR inhibitor group and the EGFR inhibitor+nitric oxide releasing agent group. After additional 48 hrs of culture, the survival rate of cells was determined by Cell Counting Kit-8 (CCK-8) assay kit (C0037, Shanghai Beyotime Biotechnology Inc., Beyotime Biotechnology), to calculate the proliferative toxicity of the EGFR inhibitor to cells and the ameliorating effect of the nitric oxide releasing agent to the proliferative toxicity. GraphPad Prism 6.0 Software and t-test were used to carry out a statistic analysis of the results and plot a graph.

Figure 6:
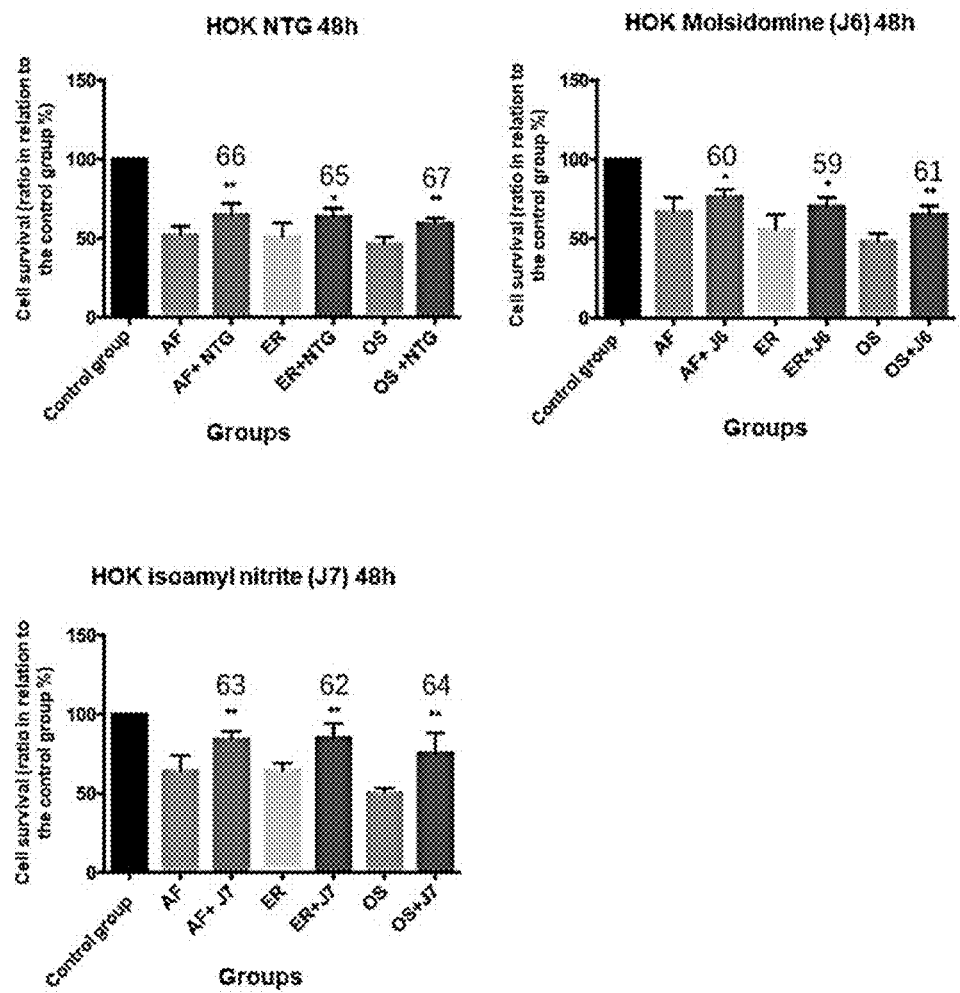
FIG. 6 depicts exemplary results of cell proliferation toxicity at 48 hours after simultaneous administration of an EGFR inhibitor and a nitric oxide releasing agent to Human Oral Keratinocytes (HOK), as measured in accordance with CCK-8 method (including the data of Examples 59-67). In the figure, NTG represents nitroglycerin, AF represents Afatinib, ER represents Erlotinib, OS represents Osimertinib. Among those, **represents $P<0.01$, indicating a significant difference as compared with the control group which is administered with the EGFR inhibitor alone; *represents $P<0.05$, indicating a significant difference as compared with the control group which is administered with the EGFR inhibitor alone, as statistically determined by using t-test. The numbers above the bar chart represent the serial numbers of the examples.

Table 4 lists various combinations of EGFR inhibitors and nitric oxide releasing agents and the corresponding experimental results (wherein the data in the cell survival rate column represent the percentages of viable cells increased by the corresponding the EGFR inhibitor+nitric oxide releasing agent group as compared to the EGFR inhibitor group). FIG. 6 lists several typical experimental results.

Human Oral Keratinocytes (HOK), and the nitric oxide releasing agent produces a significant ameliorating effect to the proliferative toxicity caused by the EGFR inhibitor.

Example 71-73

Proliferative Toxicity of EGFR Inhibitor on Human Umbilical Vein Endothelial Cells (HUVEC) and Ameliorating Effect of Nitric Oxide Releasing Agent The cultured human umbilical vein endothelial cells (HUVECs) were digested, counted, and seeded to a 96-well plate with 5000-10000 cells per well. After the cells were attached, the supernatant was discarded. The wells were divided to the blank control group, the EGFR inhibitor

TABLE 4

Experimental Conditions and Results of Example 59-70

| Example No. | EGFR inhibitor | Final Concentration | Classification | Nitric Oxide Releasing Agent | Final Concentration | Cell Survival Rate |
|---|---|---|---|---|---|---|
| 59 | Erlotinib | 10 μM | The first generation EGFR small molecule inhibitor | Molsidomine (J6) | 200 μM | Increased by 20-30% |
| 60 | Afatinib | 5 μM | The second generation EGFR small molecule inhibitor | | | |
| 61 | Osimertinib | 20 μM | The third generation EGFR small molecule inhibitor | | | |
| 62 | Erlotinib | 10 μM | The first generation EGFR small molecule inhibitor | Isoamyl nitrite (J7) | 200 μM | Increased by 25-35% |
| 63 | Afatinib | 5 μM | The second generation EGFR small molecule inhibitor | | | |
| 64 | Osimertinib | 20 μM | The third generation EGFR small molecule inhibitor | | | |
| 65 | Erlotinib | 10 μM | The first generation EGFR small molecule inhibitor | Nitroglycerin (NTG) | 200 μM | Increased by 20-30% |
| 66 | Afatinib | 5 μM | The second generation EGFR small molecule inhibitor | | | |
| 67 | Osimertinib | 20 μM | The third generation EGFR small molecule inhibitor | | | |
| 68 | Erlotinib | 10 μM | The first generation EGFR small molecule inhibitor | S-nitrosoethane-dithiolchitin | 0.30 mg/mL | Increased by 15-20% |
| 69 | Afatinib | 5 μM | The second generation EGFR small molecule inhibitor | | | |
| 70 | Osimertinib | 20 μM | The third generation EGFR small molecule inhibitor | | | |

It can be concluded from the results in Table 4 and FIG. 6 that the EGFR inhibitor has a proliferative toxicity to the group, the EGFR inhibitor+nitric oxide releasing agent group and blank solvent control group.

EGFR inhibitor group: 100 μL of the EGFR inhibitor solution was added (the final concentration was listed in Table 5, the EGFR inhibitor solution are DMSO solution); the EGFR inhibitor+nitric oxide releasing agent group: the EGFR inhibitor solution and the nitric oxide releasing agent solution were added (the final concentrations of the EGFR inhibitor and the nitric oxide releasing agent were listed in Table 5, and depending on the solubility of the nitric oxide releasing agents, the nitric oxide releasing agent solution was ethanol solution or aqueous solution); the blank control group: except the normal replacement of medium, no additional solution was added; a plurality of blank solvent control group: an equal volume of the same type of solvent solution as the corresponding EGFR inhibitor group or the EGFR inhibitor+nitric oxide releasing agent group was added. The blank solvent control group was used for data correction to eliminate the effect of solvent to the result in the EGFR inhibitor group and the EGFR inhibitor+nitric oxide releasing agent group. After additional 48 hrs of culture, the survival rate of cells was determined by Cell Counting Kit-8 (CCK-8) assay kit (C0037, Shanghai Beyotime Biotechnology Inc., Beyotime Biotechnology), to calculate the proliferative toxicity of the EGFR inhibitor to cells and the ameliorating effect of the nitric oxide releasing agent to the proliferative toxicity. GraphPad Prism 6.0 Software and t-test were used to carry out a statistic analysis of the results and plot a graph.

Figure 7:
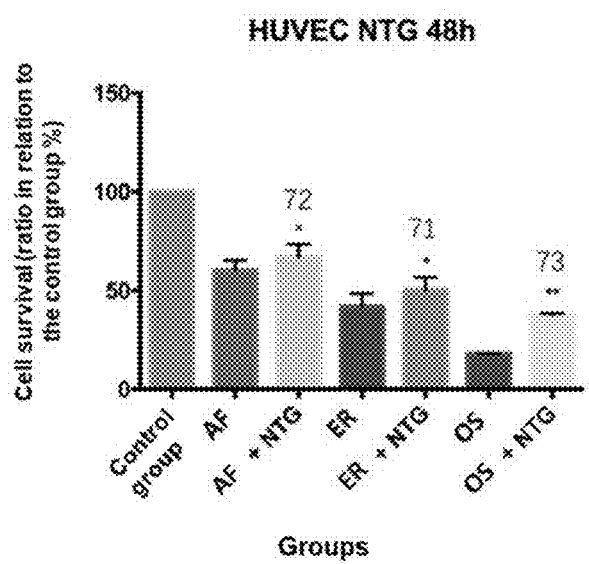
FIG. 7 depicts exemplary results of cell proliferation toxicity at 48 hours after simultaneous administration of an EGFR inhibitor and a nitric oxide releasing agent to HUVEC cells, as measured in accordance with CCK-8 method (including the data of Examples 71-73). In the figures, NTG represents nitroglycerin, AF represents Afatinib, ER represents Erlotinib, OS represents Osimertinib. Of those, **represents $P<0.01$, indicating a significant difference as compared with the control group which is administered with the EGFR inhibitor alone; *represents $P<0.05$, indicating a significant difference as compared with the control group which is administered with the EGFR inhibitor alone, as statistically determined by using t-test. The numbers above the bar chart represent the serial numbers of the examples.

Table 5 lists various combinations of EGFR inhibitors and nitric oxide releasing agents and the corresponding experimental results (wherein the data in the cell survival rate column represent the percentages of viable cells increased by the corresponding the EGFR inhibitor+nitric oxide releasing agent group as compared to the EGFR inhibitor group). FIG. 7 lists the experimental results.

Example 74-85

Proliferative Toxicity of EGFR Inhibitor on Human Foreskin Fibroblasts (HFF) and Ameliarating Effect of Nitric Oxide Releasing Agent The cultured human foreskin fibroblasts (HFF) were digested, counted, and seeded to a 96-well plate with 5000-10000 cells per well. After the cells were attached, the supernatant was discarded. The wells were divided to the blank control group, the EGFR inhibitor group, the EGFR inhibitor+nitric oxide releasing agent group and blank solvent control group. EGFR inhibitor group: 100 μL of the EGFR inhibitor solution was added (the final concentration was listed in Table 6, the EGFR inhibitor solutionare DMSO solution); the EGFR inhibitor+nitric oxide releasing agent group: the EGFR inhibitor solution and the nitric oxide releasing agent solution were added (the final concentrations of the EGFR inhibitor and the nitric oxide releasing agent were listed in Table 6, and depending on the solubility of the nitric oxide releasing agents, the nitric oxide releasing agent solution was ethanol solution or aqueous solution); the blank control group: except the normal replacement of medium, no additional solution was added; a plurality of blank solvent control group: an equal volume of the same type of solvent as the corresponding EGFR inhibitor group or the EGFR inhibitor+nitric oxide releasing agent group was added. The blank solvent control group was used for data correction to eliminate the effect of solvent to the result in the EGFR inhibitor group and the EGFR inhibitor+nitric oxide releasing agent group. After additional 48 hrs of culture, the survival rate of cells was determined by Cell Counting Kit-8 (CCK-8) assay kit (C0037, Shanghai Beyotime Biotechnology Inc., Beyotime Biotechnology), to calculate the proliferative toxicity of the EGFR inhibitor to cells and the ameliorating effect of the nitric oxide releasing agent to the proliferative toxicity. GraphPad Prism 6.0 Software and t-test were used to carry out a statistic analysis of the results and plot a graph.

TABLE 5

Experimental Conditions and Results of Example 71-73

| Example No. | EGFR inhibitor | Final Concentration | Classification | Nitric Oxide Releasing Agent | Final Concentration | Cell Survival Rate |
|---|---|---|---|---|---|---|
| 71 | Erlotinib | 10 μM | The first generation EGFR small molecule inhibitor | Nitroglycerin (NTG) | 200 μM | Increased by 20-30% |
| 72 | Afatinib | 5 μM | The second generation EGFR small molecule inhibitor | | | Increased by 15-20% |
| 73 | Osimertinib | 20 μM | The third generation EGFR small molecule inhibitor | | | Increased by 90-100% |

It can be concluded from the results in Table 5 and FIG. 7 that the EGFR inhibitor has a proliferative toxicity to the human umbilical vein endothelial cells (HUVEC), and the nitric oxide releasing agent produces a significant ameliorating effect to the proliferative toxicity caused by the EGFR inhibitor.

Figure 8:
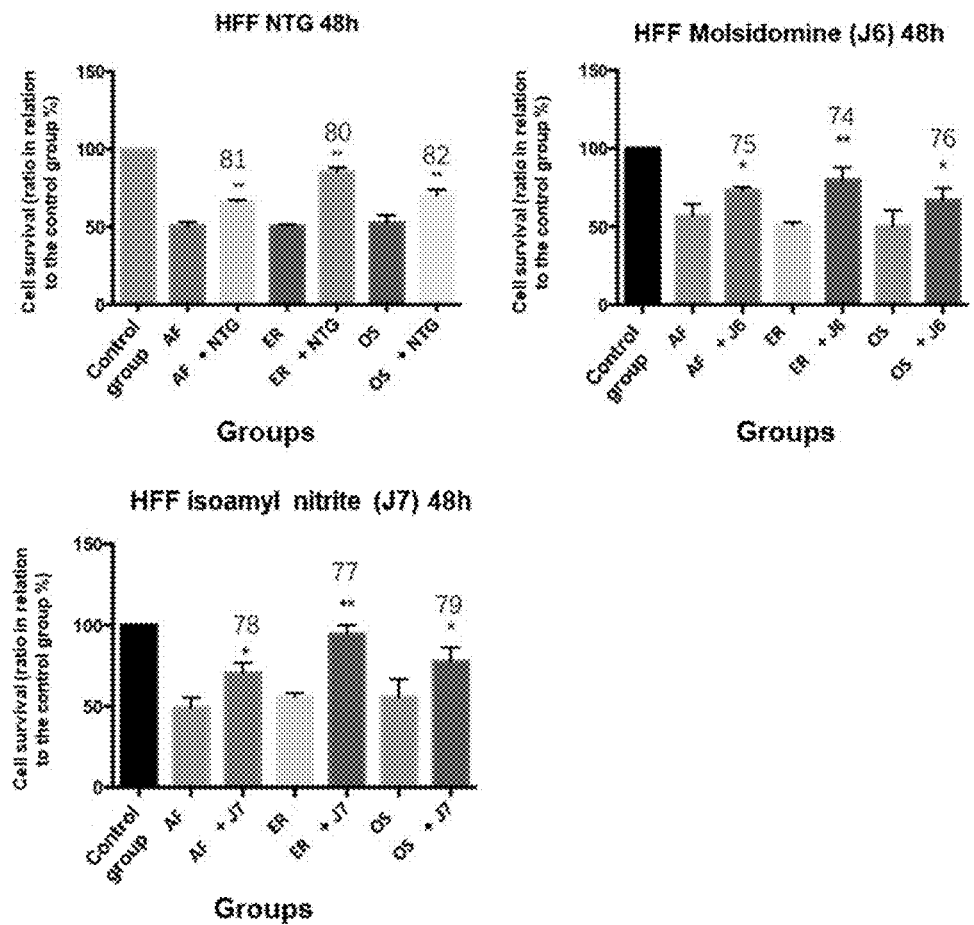
FIG. 8 depicts exemplary results of cell proliferation toxicity at 48 hours after simultaneous administration of an EGFR inhibitor and a nitric oxide releasing agent to HFF cells, as measured in accordance with CCK-8 method (including the data of Examples 74-82). In the figure, NTG represents nitroglycerin, AF represents Afatinib, ER represents Erlotinib, OS represents Osimertinib. Among those, **represents $P<0.01$, indicating a significant difference as compared with the control group which is administered with the EGFR inhibitor alone; *represents $P<0.05$, indicating a significant difference as compared with the control group which is administered with the EGFR inhibitor alone, as statistically determined by using t-test. The numbers above the bar chart represent the serial numbers of the examples.

Table 6 lists various combinations of EGFR inhibitors and nitric oxide releasing agents and the corresponding experimental results (wherein the data in the cell survival rate column represent the percentages of viable cells increased by the corresponding the EGFR inhibitor+nitric oxide releasing agent group as compared to the EGFR inhibitor group). FIG. 8 lists several typical experimental results.

TABLE 6

Experimental Conditions and Results of Example 74-85

| Example No. | EGFR inhibitor | Final Concentration | Classification | Nitric Oxide Releasing Agent | Final Concentration | Cell Survival Rate |
|---|---|---|---|---|---|---|
| 74 | Erlotinib | 10 μM | The first generation EGFR small molecule inhibitor | Molsidomine (J6) | 200 μM | Increased by 20-70% |
| 75 | Afatinib | 5 μM | The second generation EGFR small molecule inhibitor | | | |
| 76 | Osimertinib | 20 μM | The third generation EGFR small molecule inhibitor | | | |
| 77 | Erlotinib | 10 μM | The first generation EGFR small molecule inhibitor | Isoamyl nitrite (J7) | 200 μM | Increased by 30-80% |
| 78 | Afatinib | 5 μM | The second generation EGFR small molecule inhibitor | | | |
| 79 | Osimertinib | 20 μM | The third generation EGFR small molecule inhibitor | | | |
| 80 | Erlotinib | 10 μM | The first generation EGFR small molecule inhibitor | Nitroglycerin (NTG) | 200 μM | Increased by 30-90% |
| 81 | Afatinib | 5 μM | The second generation EGFR small molecule inhibitor | | | |
| 82 | Osimertinib | 20 μM | The third generation EGFR small molecule inhibitor | | | |
| 83 | Erlotinib | 10 μM | The first generation EGFR small molecule inhibitor | S-nitrosoethane-dithiolchitin | 0.30 mg/mL | Increased by 30-50% |
| 84 | Afatinib | 5 μM | The second generation EGFR small molecule inhibitor | | | |
| 85 | Osimertinib | 20 μM | The third generation EGFR small molecule inhibitor | | | |

It can be concluded from the results in Table 6 and FIG. 8 that the EGFR inhibitor has a proliferative toxicity to the human foreskin fibroblasts (HFF), and the nitric oxide releasing agent produces a significant ameliorating effect to the proliferative toxicity caused by the EGFR inhibitor.

Example 86-91

Determination of the Effect of the EGFR Inhibitor on the Intracellular NO Levels The cultured HaCaT, HUVEC and hMSC were respectively digested, counted, and seeded into 6-well plates with 100,000-600,000 cells per well. After the cells were attached, the supernatant was discarded, and 1.5 mL of the EGFR inhibitor solution diluted to the final concentration as shown in Table 7 was added into the wells of the 6-well plates, wherein no additional solution was added to the blank control group, except the normal replacement of basic medium. After 12-24 hrs of addition of the EGFR inhibitor, the supernatant was discarded, while 100 μL of a cell lysis solution was added to the cells in the 6-well plates (specifically for the detection of nitric oxide, S3090, Beyotime Inc.). After 30 s of lysis, 50 μL cell lysis solution was taken. The NO level in the cell lysis solution was detected by using NO assay kit (S0021, Beyotime Inc.). GraphPad Prism 6.0 Software and t-test were used to carry out a statistic analysis of the results and plot a graph.

Figure 9:
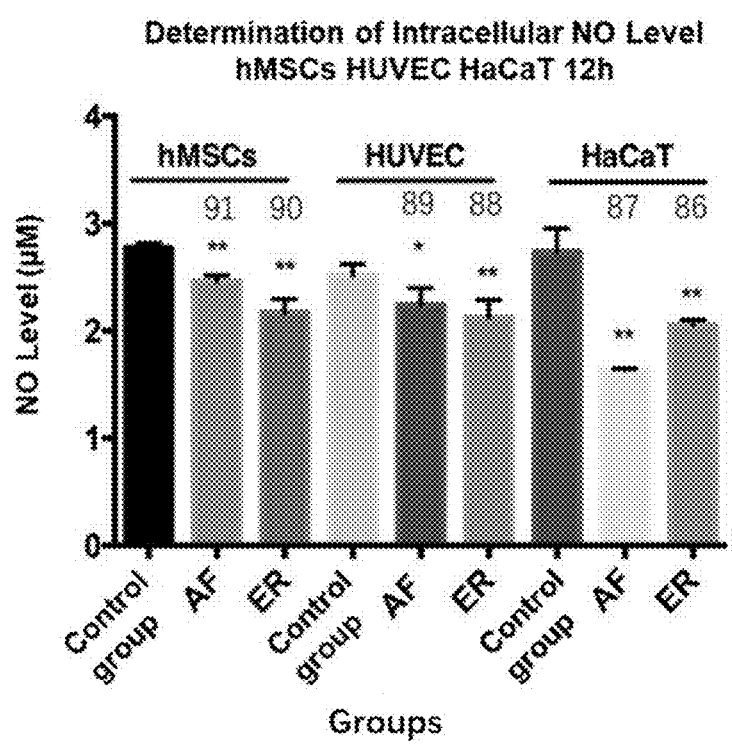
FIG. 9 depicts exemplary results of the intracellular NO levels at 12 hours after administration of an EGFR inhibitor to hMSC, HUVEC and HaCaT cells, respectively, as measured by using a NO assay kit (S0021, Beyotime Inc.) (including the data of Examples 86-91). In the figure, AF represents Afatinib, ER represents Erlotinib, and the control group is a basic medium representing a biological level. Of those, ** represents $P<0.01$, indicating a significant difference as compared with the control group; * represents $P<0.05$, indicating a significant difference as compared with the control group, as statistically determined by using t-test. The numbers above the bar chart represent the serial numbers of the examples.

Table 7 lists the results of the effect of various EGFR inhibitors to the intracellular NO levels of various cell lines (wherein the data in the NO level column represents the percentages of NO concentration decreased by the corresponding EGFR inhibitor as compared to the control group). FIG. 9 lists the experimental results.

TABLE 7

Experimental Conditions and Results of Example 86-91

| Example No. | Cells | EGFR inhibitor | Final Concentration | Classification | NO Level |
|---|---|---|---|---|---|
| 86 | HaCaT | Erlotinib | 20 µM | The first generation EGFR small molecule inhibitor | Decreased by 28% |
| 87 | HaCaT | Afatinib | 10 µM | The second generation EGFR small molecule inhibitor | Decreased by 42% |
| 88 | HUVEC | Erlotinib | 20 µM | The first generation EGFR small molecule inhibitor | Decreased by 22% |
| 89 | HUVEC | Afatinib | 10 µM | The second generation EGFR small molecule inhibitor | Decreased by 15% |
| 90 | hMSCs | Erlotinib | 20 µM | The first generation EGFR small molecule inhibitor | Decreased by 30% |
| 91 | hMSCs | Afatinib | 10 µM | The second generation EGFR small molecule inhibitor | Decreased by 10% |

It can be concluded from the results in Table 7 and FIG. 9 that the EGFR inhibitor significantly reduces the intracellular NO level.

Example 92-95

Figure 10:
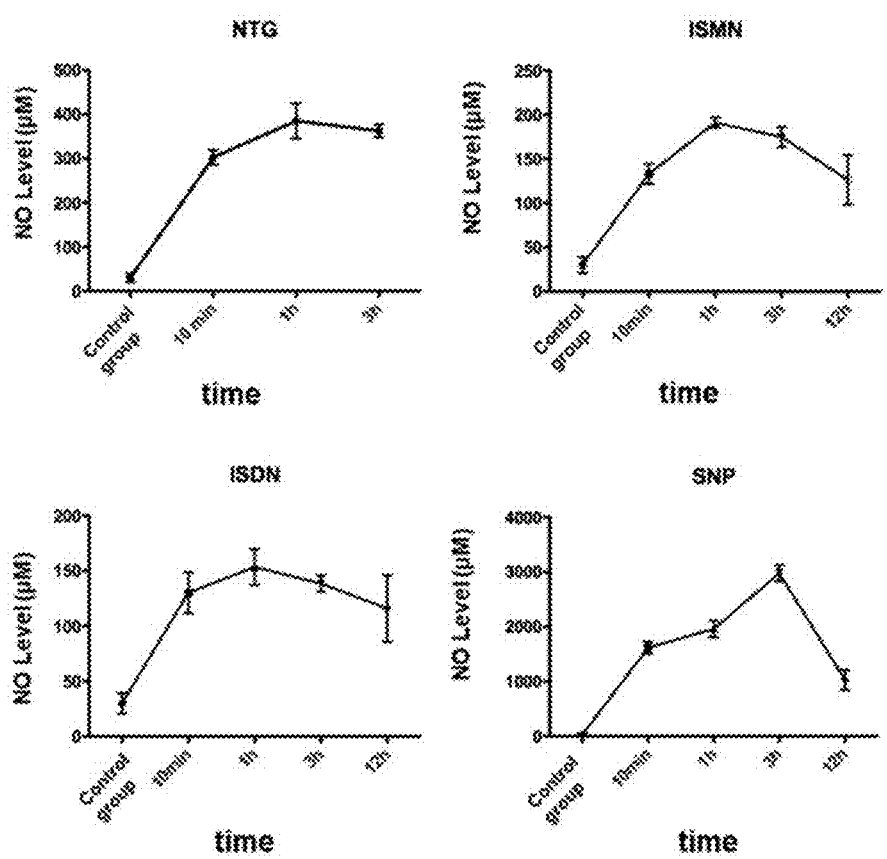
FIG. 10 depicts exemplary results of the extracellular NO levels at 12 hours after administration of a nitric oxide releasing agent to HFF cells, as measured by using a NO assay kit (S0021, Beyotime Inc.) (including the data of Examples 92-95). In the figure, NTG represents nitroglycerin, ISMN represents isosorbide mononitrate, ISDN represents isosorbide dinitrate, SNP represents sodium nitroprusside, and the control group is a basic medium representing a biological level.

Determination of the Effect of the Nitric Oxide Releasing Agent on the Extracellular NO Levels The cultured HFF cells were digested, counted, and seeded into a 96-well plate with 5,000-10,000 cells per well. After the cells were attached, the supernatant was discarded, 100 µL of the nitric oxide releasing agent solution diluted to a specific concentration (Example 92: 0.2 mM nitroglycerin (NTG); Example 93: 4 mM isosorbide mononitrate (ISMN); Example 94: 0.4 mM isosorbide dinitrate (ISDN); Example 95: 20 mM sodium nitroprusside (SNP)) was added into the wells of the 96-well plate. No additional solution was added into the blank control group except the normal replacement of medium. At various time points after the addition of the nitric oxide releasing agent (10 mins, 1 hr, 3 hrs and 12 hrs), 50 µL of supernatant of each group was collected. The NO level in the cell culture supernatant was detected by using NO assay kit (S0021, Beyotime Inc.). FIG. 10 lists the experimental results.

It can be concluded from FIG. 10 that the administration of the nitric oxide releasing agent may increase the extracellular NO levels, and different concentrations of the nitric oxide releasing agent result in different increasing of the NO levels. During the therapy, the concentrations of nitric oxide releasing agent may be selected in accordance with the disease condition.

Example 96-128

Figure 11:
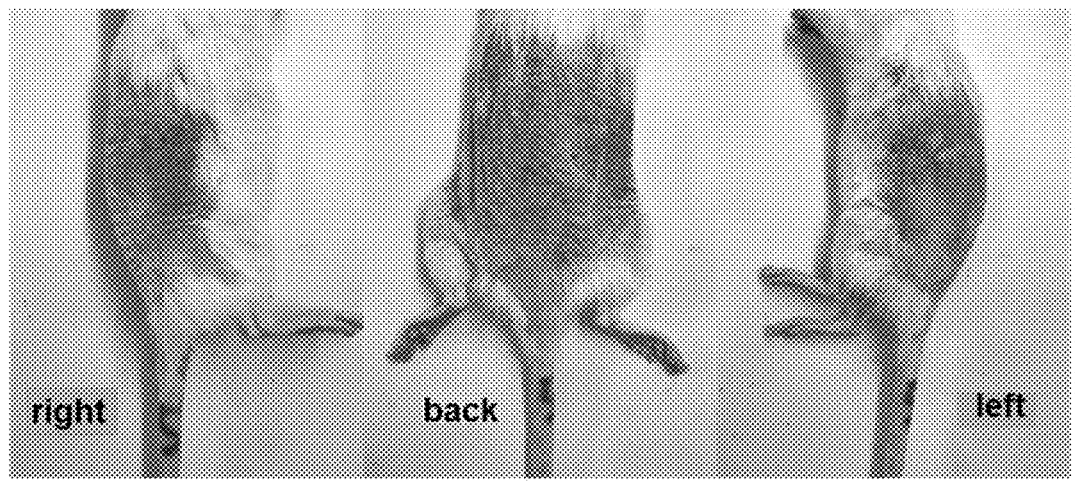
FIG. 11 depicts the photographs of right side, back side, and left side of a rat model where rashes are caused by the EGFR inhibitor. As seen from the photographs, there is no difference between the rash locations on left and right sides, and the degrees of rash are similar on both sides.
Figure 12:
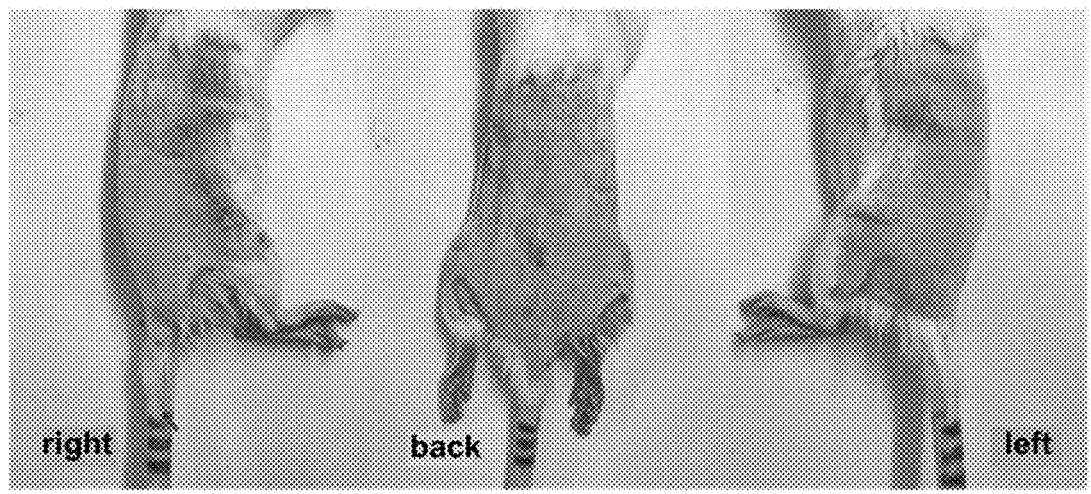
FIG. 12 depicts the photographs of right side, back side and left side of a typical rat (which the medicament is topically administered on the left side) in the administration group of examples 96-132. As seen from the photographs, the rashes on the left side which the medicament was administered are significangtly less serious than those on the right side which the medicament was not administered.
Figure 13:
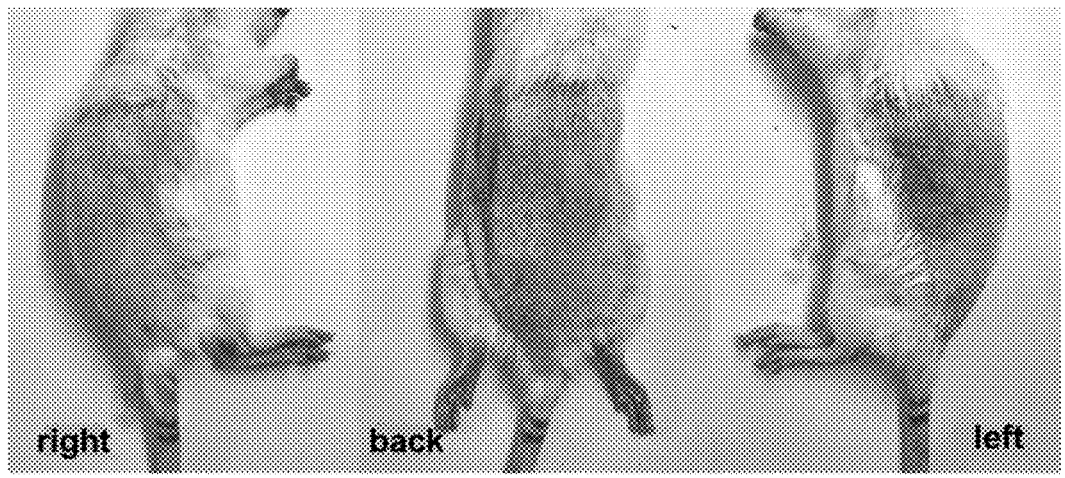
FIG. 13 depicts the photographs of right side, back side and left side of a typical rat (which the medicament is topically administered on the right side) in the administration group of examples 96-132. As seen from the photographs, the rash on the right side which the medicament was administered are significangtly less serious than those on the left side which the medicament was not administered.
Figure 14:
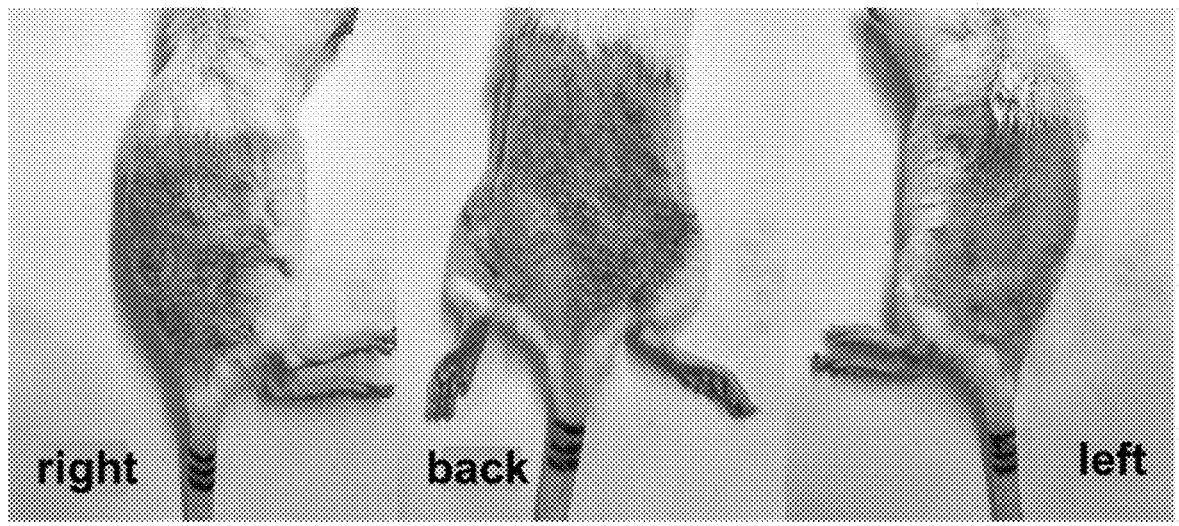
FIG. 14 depicts the photographs of right side, back side and left side of a typical administration rat (which the medicament is topically administered on the left side) in the administration group of examples 133-142. As seen from the photographs, the rashes on the left side which the medicament was administered are significangtly less serious than those on the right side which the medicament was not administered.
Figure 15:
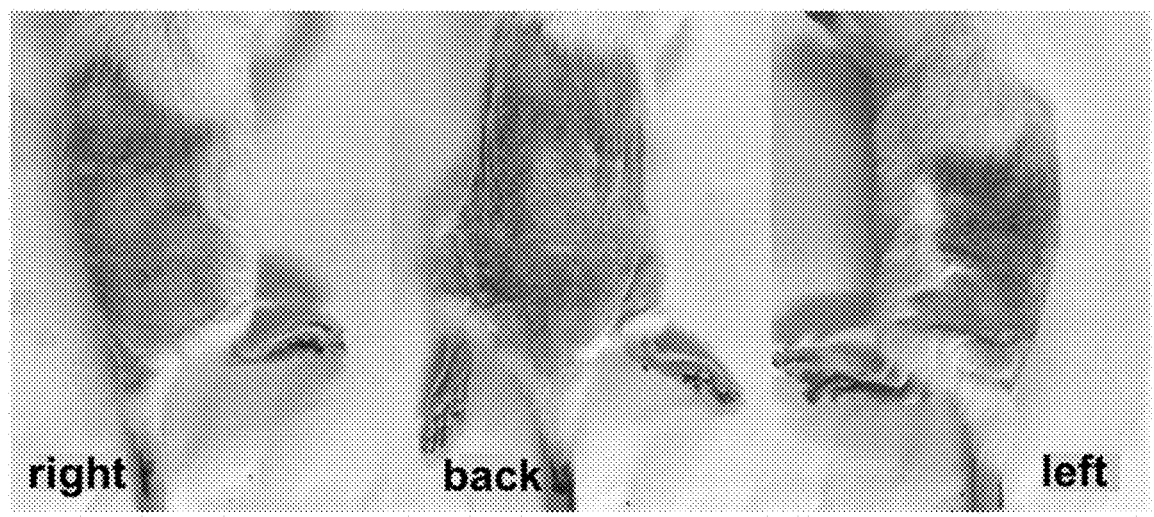
FIG. 15 depicts the photographs of right side, back side and left side of a typical administration rat (which the medicament was administered on the right side) in the administration group of examples 133-142. As seen from the photographs, the rashes on the right side which the medicament was administered are significangtly less serious than those on the left side which the medicament was not administered.

Experiments for Demonstrating the Ability of Preventing the Occurrence of Rash Caused by a Small Molecular EGFR Inhibitor in Rat Models Construction of a rat model: A small molecular EGFR inhibitor was administered to a 6-week female rat by daily gavage, and after several days, a large area of rashes appeared on the back of the rat (the photographs are shown in FIG. 11). There was no difference between the left and right side of the rash area, and the rash degree was similar on both sides. Similar to humans, the rat develops rash on its body after oral administration of a small molecular EGFR inhibitor. Both of them have exactly the same cause, and exhibit similar symptoms. Thus, this rat model is a very good animal model to mimick the rash caused by the EGFR inhibitor.

SD rats were fed for 1 week (about 200 g), and then divided into groups, each of which comprised 10 rats. The hair on the back of the rats were gently shaved with an electric shaver at the day before the experiments, and then the intragastric administration was initiated. The EGFR inhibitor was dissolved in a mixed solution (Cremophor EL:ethanol=1:1) and 3× diluted with a PBS buffer solution when administration. The gavage amount was less than 2 mL each time, and the dosage was shown in Table 8. After gavage, one side of the rat (about 1.2 cm×3 cm area) was topically administered with an ointment of the nitric oxide releasing agent (the type and concentration thereof were shown in Table 8), while the other side was not administered (as a blank control). After administration, the rat was fixed by a cylinder for about 4 hrs. Then, the rat was released, wiped with water to remove the residual medicament at the administration site, and returned to the cage. The gavage frequency of the EGFR inhibitor was shown in Table 8, while the nitric oxide releasing agent was administered only once a day. The oral gavage of EGFR inhibitor and topical administration of ointment were repeated every day, until the side of rat back, as blank control, developed apparent rash. At this point, the number of rats on which the skin of the ointment treated side kept normal or remarkably less serious as compared with the untreated side was recorded as the number of rats whose rash was effectively controlled.

Table 8 lists various combinations of small molecular EGFR inhibitors and the nitric oxide releasing agent ointments, as well as the corresponding experiment results (wherein the values in the control rate column=the number of rats whose rash was effectively controlled in each group/the number of rats successfully developed rash×100%).

TABLE 8

Experimental Conditions and Results of Example 96-128

| Example No. | EGFR inhibitor | Classification of Inhibitor | Dosage | Frequency | Administration | Concentration wt % | Administration side | Days | Control Rate |
|---|---|---|---|---|---|---|---|---|---|
| 96 | Afatinib | The second generation EGFR small molecule inhibitor | 50 mg/kg | once per day | Nitroglycerin ointment | 0.05% | Left | 8 | 20% |
| 97 | Afatinib | The second generation EGFR small molecule inhibitor | 50 mg/kg | once per day | Nitroglycerin ointment | 0.1% | Left | 8 | 80% |
| 98 | Afatinib | The second generation EGFR small molecule inhibitor | 50 mg/kg | once per day | Nitroglycerin ointment | 0.2% | Left | 8 | 60% |
| 99 | Gefitinib | The first generation EGFR small molecule inhibitor | 80 mg/kg | twice per day | Nitroglycerin ointment | 0.1% | Left | 10 | 62.5% |
| 100 | Erlotinib | The first generation EGFR small molecule inhibitor | 70 mg/kg | once per day | Nitroglycerin ointment | 0.1% | Left | 14 | 85.71% |
| 101 | Osimertinib | The third generation EGFR small molecule inhibitor | 60 mg/kg | twice per day | Nitroglycerin ointment | 0.1% | Left | 12 | 62.5% |
| 102 | EAI045 | The fourth generation EGFR small molecule inhibitor | 80 mg/kg | once per day | Nitroglycerin ointment | 0.1% | Left | 10 | 57.14% |
| 103 | Erlotinib | The first generation EGFR small molecule inhibitor | 70 mg/kg | once per day | Isosorbide mononitrate/isosorbide dinitrate mixed ointment | 0.1% | Left | 10 | 71.43% |
| 104 | Afatinib | The second generation EGFR small molecule inhibitor | 50 mg/kg | once per day | Isosorbide mononitrate/isosorbide dinitrate mixed ointment | 0.1% | Left | 8 | 66.67% |
| 105 | Erlotinib | The first generation EGFR small molecule inhibitor | 70 mg/kg | once per day | Nicorandil ointment | 0.1% | Left | 10 | 62.5% |
| 106 | Afatinib | The second generation EGFR small molecule inhibitor | 50 mg/kg | once per day | Nicorandil ointment | 0.1% | Left | 7 | 70% |
| 107 | Erlotinib | The first generation EGFR small molecule inhibitor | 70 mg/kg | once per day | Sodium nitrate ointment | 0.1% | Left | 8 | 28.57% |
| 108 | Afatinib | The second generation EGFR small molecule inhibitor | 50 mg/kg | once per day | Sodium nitrate ointment | 0.1% | Left | 5 | 30% |
| 109 | Erlotinib | The first generation EGFR small molecule inhibitor | 70 mg/kg | once per day | Isoamyl nitrite ointment | 0.1% | Left | 9 | 57.14% |
| 110 | Afatinib | The second generation EGFR small molecule inhibitor | 50 mg/kg | once per day | Isoamyl nitrite ointment | 0.1% | Left | 6 | 77.78% |
| 111 | Erlotinib | The first generation EGFR small molecule inhibitor | 70 mg/kg | once per day | Sodium nitrite ointment | 0.1% | Left | 11 | 50% |
| 112 | Afatinib | The second generation EGFR small molecule inhibitor | 50 mg/kg | once per day | Sodium nitrite ointment | 0.1% | Left | 8 | 60% |
| 113 | Erlotinib | The first generation EGFR small molecule inhibitor | 70 mg/kg | once per day | Molsidomine ointment | 0.1% | Left | 11 | 37.5% |

TABLE 8-continued

Experimental Conditions and Results of Example 96-128

| Example No. | EGFR inhibitor | Classification of Inhibitor | Dosage | Frequency | Administration | Concentration wt % | Administration side | Days | Control Rate |
|---|---|---|---|---|---|---|---|---|---|
| 114 | Afatinib | The second generation EGFR small molecule inhibitor | 50 mg/kg | once per day | Molsidomine ointment | 0.1% | Left | 8 | 44.44% |
| 115 | Erlotinib | The first generation EGFR small molecule inhibitor | 70 mg/kg | once per day | Sodium nitroprusside ointment | 0.1% | Left | 10 | 57.14% |
| 116 | Afatinib | The second generation EGFR small molecule inhibitor | 50 mg/kg | once per day | Sodium nitroprusside ointment | 0.1% | Left | 7 | 60% |
| 117 | Erlotinib | The first generation EGFR small molecule inhibitor | 70 mg/kg | once per day | S-nitrosothiolsilica nanosphere ointment | 0.1% | Left | 10 | 50% |
| 118 | Afatinib | The second generation EGFR small molecule inhibitor | 50 mg/kg | once per day | S-nitrosothiolsilica nanosphere ointment | 0.1% | Left | 7 | 66.67% |
| 119 | Erlotinib | The first generation EGFR small molecule inhibitor | 70 mg/kg | once per day | S-nitrosoethanedithiol-chitin ointment | 0.1% | Left | 11 | 44.44% |
| 120 | Afatinib | The second generation EGFR small molecule inhibitor | 50 mg/kg | once per day | S-nitrosoethanedithiol-chitin ointment | 0.1% | Left | 7 | 60% |
| 121 | Erlotinib | The first generation EGFR small molecule inhibitor | 70 mg/kg | once per day | Oligo-propylenediamine grafted chitosan NONOate ointment | 0.1% | Right | 11 | 25% |
| 122 | Afatinib | The second generation EGFR small molecule inhibitor | 50 mg/kg | once per day | Oligo-propylenediamine grafted chitosan NONOate ointment | 0.1% | Right | 7 | 44.44% |
| 123 | Erlotinib | The first generation EGFR small molecule inhibitor | 70 mg/kg | once per day | N-nitrosodibutylamine ointment | 0.1% | Right | 8 | 33.33% |
| 124 | Afatinib | The second generation EGFR small molecule inhibitor | 50 mg/kg | once per day | N-nitrosodibutylamine ointment | 0.1% | Right | 7 | 44.44% |
| 125 | Erlotinib | The first generation EGFR small molecule inhibitor | 70 mg/kg | once per day | Hydroxyldiazenesulfonic acid-1-oxide disodium salt ointment | 0.1% | Right | 10 | 37.5% |
| 126 | Afatinib | The second generation EGFR small molecule inhibitor | 50 mg/kg | once per day | Hydroxyldiazenesulfonic acid-1-oxide disodium salt ointment | 0.1% | Right | 8 | 40% |
| 127 | Erlotinib | The first generation EGFR small molecule inhibitor | 70 mg/kg | once per day | Streptozocin ointment | 0.1% | Right | 10 | 42.86% |
| 128 | Afatinib | The second generation EGFR small molecule inhibitor | 50 mg/kg | once per day | Streptozocin ointment | 0.1% | Right | 8 | 44.44% |

It can be concluded from the results in Table 8 that the nitric oxide releasing agent ointment can effectively prevent the rash caused by the small molecular EGFR inhibitor.

Example 129-131

Experiments for Demonstrating the Ability of Preventing the Occurrence of Rash Caused by the Small Molecule EGFR Inhibitors in Rat Models A rat animal model was constructed. See Examples 96, 99 and 101.

*Nitrosomonas* Wash Solution Preparation

*Nitrosomonas europaea* (Cat. No. ATCC 19718) was inoculated into an inorganic culture solution (Cat. No. ATCC 2265) at about 200 rpm, at 26° C., and expanded for 3-5 days in the dark. Get the mother liquor of the bacteria, dilute the mother liquor with the inorganic culture solution to different bacterial concentrations (such as $10^7, 10^8, 10^9, 10^{10}$ bacteria/ml), the bacterial concentration is measured by a blood cell counter and get *Nitrosomonas*.

Table 9 lists the animal experimental combinations of various small molecule EGFR inhibitors and nitric oxide releasing agents (*Nitrosomonas*), and the corresponding experimental results (where the value of the control rate column=the number of rats whose rash was effectively controlled in each group/each group of rash models was only completed×100%).

on the back of the rats were gently shaved with an electric shaver at the day before the experiments, and then the administration test was performed. The Cetuximab monoclonal antibody solution diluted with physiological saline was injected twice per week into the tail vein of rats at an injection rate of 1.3 ml/kg/min, wherein the injection time to a single rat would not be less than 15 mins, and the injection dose was 100 mg/kg. After injection, 0.1% nitroglycerin ointment (about 0.1 g) was topically administered to the left side of the rat (about 1.2 cm*3 cm area), while the right side was not administered as a blank control. After topical administration, the rat was fixed by cylinder for about 4 hrs. Then, the rat was released, wiped with water to remove the residual medicament at the administration site, and returned to the cage. The rate was subjected to tail vein injection twice per week, and was topically administrated once a day with the nitric oxide releasing agent at one side of the back, until the control side developed apparent rash. After 15 days of administration, the number of rats in which the skin condition of the administered side (left side) kept normal or remarkably less serious than the untreated side (right side), was recorded as the number of rats whose rash was effectively inhibited.

TABLE 9

Experimental conditions and experimental results of Examples 129-131

| Example No. | EGFR inhibitor | Classification of Inhibitor | Dosage | Frequency | Administration | Concentration wt % | Administration side | Day | Control Rate |
|---|---|---|---|---|---|---|---|---|---|
| 129 | Afatinib | The second generation EGFR small molecule inhibitor | 50 mg/kg | once per day | Nitrosomonas solution | $10^9$ bacteria/mL | Left | 8 | 37.5% |
| 130 | Gefitinib | The first generation EGFR small molecule inhibitor | 80 mg/kg | twice per day | Nitrosomonas solution | $10^9$ bacteria/mL | Left | 10 | 40% |
| 131 | Osimertinib | The third generation EGFR small molecule inhibitor | 60 mg/kg | twice per day | Nitrosomonas solution | $10^9$ bacteria/mL | Left | 12 | 33.3% |

Example 132

Experiments for Demonstrating the Ability of Preventing the Occurrence of Rash Caused by the Anti-EGFR Monoclonal Antibodies in Rat Models SD rats were fed for 1 week (about 200 g), and then divided to groups, each of which comprised 10 rats. The hair Table 10 lists various combinations of anti-EGFR monoclonal antibodies and nitric oxide releasing agent ointments in animal models and the corresponding experiment results (wherein the values in the control rate column=the number of rats whose rash was effectively controlled in each group/the number of rats successfully developed rash×100%).

TABLE 10

Experimental Conditions and Results of Example 132

| Example No. | EGFR inhibitor | Classification of Inhibitor | Dosage | Frequency | Administration | Concentration | Administration Side | Days | Control Rate |
|---|---|---|---|---|---|---|---|---|---|
| 132 | Cetuximab | Monoclonal antibody | With an injection rate of 1.3 ml/kg/min | Tail vein injection twice per week | Nitroglycerin ointment | 0.1% | Left | 15 | 57.14% |

It can be concluded from the results in Table 10 that the nitric oxide releasing agent ointment can effectively prevent the rash caused by the anti-EGFR monoclonal antibodies.

Example 133-142

Experiments for Demonstrating the Ability of Treating the Occurrence of Rash Caused by the Small Molecular EGFR Inhibitors in Rat Models SD rats were fed for 1 week (about 200 g), and then divided into groups, each of which comprised 10 rats. The hair on the back of the rats were gently shaved with an electric shaver at the day before the experiments, and then the intragastric administration was initiated. The EGFR inhibitor was dissolved in a mixed solution (cremophor EL:ethanol=1:1), and 3× diluted with a PBS buffer solution when administration. The gavage amount was less than 2 mL every time, and the dosage was shown in Table 11. The gavage was performed every day, until the rat developed the symptom of rash, and at this time the therapeutic experiments were initiated. During the treatment, the rat was continuously subject to gavage with the EGFR inhibitor every day, and then topically administered with the nitric oxide releasing agent ointment at one side of the rat (about 1.2 cm×3 cm area), while the other side was not administered (as a blank control). After administration, the rat was fixed by a cylinder for about 4 hrs. After 4 hrs, the rat was released, wiped with water to remove the residual medicament at the administration site, and returned to the cage. The gavage frequency of the EGFR inhibitor was shown in Table 11, but the nitric oxide releasing agent was administered only once a day. The rat was continuously subject to gavage with the EGFR inhibitor every day, and topically administered with the nitric oxide releasing agent at one side of the back. After 15 days of administration, the number of rats on which the skin of the administered side kept normal or remarkably less serious than the untreated side was recorded as the number of rats whose rash was effectively treated.

Table 11 lists various combinations of the small molecular EGFR inhibitors and the nitric oxide releasing agent ointments, as well as the corresponding experimental results (wherein the values in the relief rate column=the number of rats whose rash was effectively treated in each group/the number of rats successfully developed rash×100%).

TABLE 11

Example 133-142 Experimental Conditions and Results

| Example No. | EGFR inhibitor | Classification of Inhibitor | Dosage | Frequency | Administration Modeling Days | Administration | Concentration | Administration Side | Ameliorating Rate |
|---|---|---|---|---|---|---|---|---|---|
| 133 | Erlotinib | The first generation EGFR small molecule inhibitor | 70 mg/kg | once per day | 10 | Nitroglycerin ointment | 0.1% | Left | 50% |
| 134 | Afatinib | The second generation EGFR small molecule inhibitor | 30 mg/kg | once per day | 6 | Nitroglycerin ointment | 0.1% | Left | 55.56% |
| 135 | Osimertinib | The third generation EGFR small molecule inhibitor | 60 mg/kg | twice per day | 14 | Nitroglycerin ointment | 0.1% | Left | 28.57% |
| 136 | EAI045 | The fourth generation EGFR small molecule inhibitor | 80 mg/kg | once per day | 14 | Nitroglycerin ointment | 0.1% | Left | 25% |
| 137 | Afatinib | The second generation EGFR small molecule inhibitor | 30 mg/kg | once per day | 6 | Nicorandil ointment | 0.1% | Left | 33.33% |
| 138 | Afatinib | The second generation EGFR small molecule inhibitor | 30 mg/kg | once per day | 6 | Isosorbide mononitrate/ isosorbide dinitrate mixed ointment | 0.1% | Left | 30% |
| 139 | Afatinib | The second generation EGFR small molecule inhibitor | 30 mg/kg | once per day | 6 | Sodium nitroprusside ointment | 0.1% | Left | 22.22% |
| 140 | Afatinib | The second generation EGFR small molecule inhibitor | 30 mg/kg | once per day | 6 | A polymer ointment | 0.1% | Left | 44.44% |
| 141 | Afatinib | The second generation EGFR small molecule inhibitor | 30 mg/kg | once per day | 6 | Molsidomine ointment | 0.1% | Left | 37.5% |
| 142 | Afatinib | The second generation EGFR small molecule inhibitor | 30 mg/kg | once per day | 6 | Nitroglycerin ointment | 0.1% | Right | 55.56% |

It can be concluded from the results in Table 11 that the nitric oxide releasing agent ointment can effectively treat the rash caused by the small molecular EGFR inhibitors.

Example 143

Experiments for Demonstrating the Ability of Treating the Occurrence of Rash Caused by the Anti-EGFR Monoclonal Antibodies in Rat Models SD rats were fed for 1 week (about 200 g), and then divided to groups, each of which comprised 10 rats. The hair on the back of the rats were gently shaved with an electric shaver at the day before the experiments, and then the intragastric administration was initiated. The Cetuximab monoclonal antibody solution diluted with physiological saline was injected twice per week into the tail vein of rats at an injection rate of 1.3 ml/kg/min, wherein the injection time to a single rat would not be less than 15 mins, and the injection dose was 100 mg/kg. The rat was continuously administered for 1 to 2 weeks, until the rat developed rash, and at this time the treatment experiments were initiated. During the treatment, the rat was subject to injection of the anti-EGFR monoclonal antibodies twice a week, and subject to topical administration of the nitric oxide releasing agent ointment at the left side of the rat (about 1.2 cm×3 cm area) every day, while the right side was not administered (as a blank control). After administration, the rat was fixed by a cylinder for about 4 hrs. Then, the rat was released, wiped with water to remove the residual medicament at the administration site, and returned to the cage. After 15 days of administration, the number of rats on which the skin of the ointment treated side (left side) kept normal or remarkably less serious as compared with the unadministered side (right side) was recorded as the number of rats whose rash was effectively treated.

Table 12 lists various combination of the anti-EGFR monoclonal antibodies and the nitric oxide releasing agent ointment, as well as the corresponding experimental results (wherein the values in the relief rate column=the number of rats whose rash was effectively treated in each group/the number of rats successfully developed rash×100%).

Example 144-153

Comparison of 0.1% Nitroglycerin Ointment with Other Currently Clinically Available Dermatological Medicaments, and with Other Nitric Oxide Releasing Agents in the Experiments of Preventing the Rash Occurrence Caused by the Small Molecular EGFR Inhibitors The rats were fed for 1 week (about 200 g), and then divided into groups, each of which comprised 10 rats. The hair on the back of the rats were gently shaved with an electric shaver at the day before the experiments, and then the intragastric administration was initiated. The EGFR inhibitor was dissolved in a mixed solution (Cremophor EL:ethanol=1:1), and 3× diluted with a PBS buffer solution when administration. The gavage amount was less than 2 mL each time, and the dosage was shown in Table 13. After gavage, the rat was topically administered with a 0.1% nitroglycerin ointment at the left side (about 1.2 cm×3 cm area), and a clinically available topical medicament (Examples 144-150) or another nitric oxide releasing agent ointment (Examples 151-153) at the right side. After administration, the rat was fixed by a cylinder for about 4 hrs. After 4 hrs, the rat was released, wiped with water to remove the residual medicament at the administration site, and returned to the cage. The gavage frequency of the EGFR inhibitor was shown in Table 13, while the currently clinically available dermatological medicament and the other nitric oxide releasing agents were administered only once. The rat was repeatedly subject to gavage with the EGFR inhibitor every day, and topically administered on the back, until developed apparent rash at the right side. Upon occurrence of a large area of rash on the right side, the number of rats in which the rash at the left side was less serious than that at the right side was counted.

Table 13 lists various combinations of animal experiments of 0.1% nitroglycerin ointment with currently clinically available dermatological medicaments (or other nitric oxide releasing agent ointments), and the corresponding experiment results (wherein the data in the relative relief rate column=the number of rats whose rash on the left side was

TABLE 12

Experimental Conditions and Results of Example 143

| Example No. | EGFR inhibitor | Classification of Inhibitor | Dosage | Frequency | Time of Administration | Administration | Concentration | Administration side | Days | Relief Rate |
| --- | --- | --- | --- | --- | --- | --- | --- | --- | --- | --- |
| 143 | Cetuximab | McAb | 100 mg/kg, at an injection rate of 1.3 ml/kg/min | Tail vein injection twice per week | 10 (3-4 times) | Nitroglycerin ointment | 0.1% | Left | 15 | 37.5% |

It can be concluded from the results in Table 12 that the nitric oxide releasing agent ointment can effectively treat rash caused by the anti-EGFR monoclonal antibodies.

remarkably less serious than those on the right side/the number of rats successfully developed rash in each group× 100%).

TABLE 13

Example 144-153 Experimental Conditions and Results

| Example No. | EGFR inhibitor | Classification of Inhibitor | Dosage | Frequency | Administration Left side | Administration Right side | Days of administration | Relative Relief Rate |
|---|---|---|---|---|---|---|---|---|
| 144 | Erlotinib | The first-generation EGFR small molecule inhibitor | 70 mg/kg | once per day | 0.1% nitroglycerin ointment | Vk1 ointment (0.1%) | 10 | 77.78% |
| 145 | Afatinib | The second generation EGFR small molecule inhibitor | 30 mg/kg | once per day | 0.1% nitroglycerin ointment | Vk1 ointment (0.1%) | 8 | 75% |
| 146 | Osimertinib | The third generation EGFR small molecule inhibitor | 60 mg/kg | twice per day | 0.1% nitroglycerin ointment | Vk1 ointment (0.1%) | 10 | 71.43% |
| 147 | EAI045 | The fourth generation EGFR small molecule inhibitor | 80 mg/kg | once per day | 0.1% nitroglycerin ointment | Vk1 ointment (0.1%) | 10 | 62.5% |
| 148 | Afatinib | The second generation EGFR small molecule inhibitor | 30 mg/kg | once per day | 0.1% nitroglycerin ointment | triamcinolone ointment | 12 | 71.42% |
| 149 | Afatinib | The second generation EGFR small molecule inhibitor | 30 mg/kg | once per day | 0.1% nitroglycerin ointment | erythrocin ointment | 10 | 66.67% |
| 150 | Afatinib | The second generation EGFR small molecule inhibitor | 30 mg/kg | once per day | 0.1% nitroglycerin ointment | hydrocortisone ointment | 14 | 77.78% |
| 151 | Afatinib | The second generation EGFR small molecule inhibitor | 30 mg/kg | once per day | 0.1% nitroglycerin ointment | 0.1% Isoamyl nitrite ointment | 10 | 62.5% |
| 152 | Afatinib | The second generation EGFR small molecule inhibitor | 30 mg/kg | once per day | 0.1% nitroglycerin ointment | 0.1% streptozocin ointment | 10 | 77.78% |
| 153 | Afatinib | The second generation EGFR small molecule inhibitor | 30 mg/kg | once per day | 0.1% nitroglycerin ointment | 0.2% sodium nitroprusside | 8 | 77.78% |

It can be concluded from the results in Table 13 that as compared with the currently clinically available topical medicaments (which produces almost no therapeutic effect to the rash caused by the EGFR inhibitors), the 0.1% nitroglycerin ointment can effectively control the rash caused by the EGFR inhibitors; and as compared with the other nitric oxide releasing agent ointments, the 0.1% nitroglycerin ointment can more effectively control the rash caused by the EGFR inhibitors.

Examples 154-156

Experiments for Demonstrating the Ability of Preventing the Hand-Foot Syndrome Caused by the Small-Molecule EGFR Inhibitors in Rat Models Construction of a rat model: A small molecule EGFR inhibitor shown in Table 14 was administered to the 8-week female SD rats by daily gavage, and after several days, the symptoms of hand-foot syndrome appeared in the paws of the rats. Similar to the humans, the rats develop symptoms of hand-foot syndrome after oral administration of EGFR inhibitors, and exhibits similar symptoms. Thus, this rat model is a very good animal model to mimic side effects caused by EGFR inhibitors (such as hand-foot syndrome).

SD rats (about 200 g) were fed for 1 week (about 200 g), and then divided into groups, each of which comprised 10 rats. Intragastric administration was performed. The EGFR inhibitor was dissolved in a mixed solution (Cremophor EL:ethanol=1:1), and 3× diluted with a PBS buffer solution when administration. The gavage amount was less than 2 mL each time, and the dosage was shown in Table 14. After intragastric administration, the left paws of the rats (claw palms and claw seams) were topically administered with an ointment of the nitric oxide releasing agent (about 0.05 g), and the right paw was not administered (as a blank control). After administration, the rat was fixed by a cylinder for about 4 hrs. Then, the rat was released, wiped with water to remove the residual medicament at the administration site, and returned to the cage. The gavage frequency of the EGFR inhibitor was shown in Table 14, while the nitric oxide releasing agent was administered only once a day. The oral gavage of EGFR inhibitor and topical administration of ointment were repeated every day and the symptoms of the paws of the rats were observed continuously. After 10-20 days of administration, the number of rats with effective inhibition of hand-foot syndrome were counted (the number of rats was counted as the number of rats with effective inhibition of hand-foot syndrome when the administered side kept normal or remarkably less serious as compared to the unadministered side).

Table 14 lists various combinations of small molecular EGFR inhibitors and the nitric oxide releasing agent ointments, as well as the corresponding experiment results (wherein the values in the relief rate column=the number of rats whose rash was effectively controlled in each group/the number of rats successfully developed rash×100%, the establishment rate of hand-foot syndrome model in each group was 70%-90%, which is about 7-9 of 10 rats showed hand-foot syndrome model. There were cases of individual rat death or unsuccessful model during the development of hand-foot syndrome model in different administration groups of rats).

istered daily until the hand-foot syndrome appeared in the rat. At this time, the rats were started to undergo therapeutic experiments. During the course of treatment, EGFR inhibitors were continuously administered by intragastric administration. After intragastric administration, the rats' left paws (claw palms and claw seams) were coated with nitric oxide releasing agent ointment (0.05 g), and the right paw was used as a blank control. After the application, the rats were fixed in cylinder for 4 hours. After 4 hours, the rats were released, and the residual medicament in the application site was wiped off with water, and the rats were returned to the cage. The gavage frequency of the EGFR inhibitor is shown

TABLE 14

Experimental conditions and experimental results of Examples 154-156

| Example No. | EGFR inhibitor | Classification of Inhibitor | Dosage | Frequency | Administration | Concentration | Administration side | Days | Relief Rate |
|---|---|---|---|---|---|---|---|---|---|
| 154 | Gefitinib | The first generation of small molecule EGFR inhibitor | 100 mg/kg | Once per day | Nitroglycerin ointment | 0.1% | Left | 20 | 75% |
| 155 | Erlotinib | The first generation of small molecule EGFR inhibitor | 70 mg/kg | Once per day | Nitroglycerin ointment | 0.1% | Left | 15 | 66.67% |
| 156 | Afatinib | The second generation of small molecule EGFR inhibitor | 50 mg/kg | Once per day | Nitroglycerin ointment | 0.1% | Left | 10 | 57.14% |

It can be seen from the results in Table 14 that the nitric oxide releasing agent can effectively prevent the hand-foot syndrome caused by the EGFR inhibitor.

Examples 157-159

Experiments for Demonstrating the Ability of Treating the Hand-Foot Syndrome Caused by the Small-Molecule EGFR Inhibitors in Rat Models After the rats (about 200 g) were cultivated for adaption for one week, the rats were divided into groups with 10 in each group, and a intragastric administration was performed. The EGFR inhibitor was dissolved in a mixed solution (cremophor EL:ethanol=1:1), and 3× diluted with a PBS buffer solution when administration. The gavage amount was less than 2 mL every time, and the dosage was shown in Table 15. The EGFR inhibitor was continuously administered in Table 15, while the nitric oxide releasing agent is only applied once a day. After 5-8 days of application, the number of rats effectively treated for hand-foot syndrome was counted (The number of rats was accounted as the number of rats that effectively inhibited hand-foot syndrome when the administration side kept normal or remarkably less serious as compared with the unadministered side).

Table 15 lists various combinations of small molecular EGFR inhibitors and nitric oxide releasing agent ointments as well as the corresponding experimental results (where the values in the relief rate column=the number of rats whose hand-foot syndrome was effectively controlled in each group/the number of rats successfully developed hand-foot syndrome in each group×100%. The establishment rate of hand-foot syndrome model in each group was 60%-90%, which is about 6-9 of 10 rats showed hand-foot syndrome model. There were cases of individual rat death or unsuccessful model during the development of hand-foot syndrome model in different administration groups of rats).

TABLE 15

Experimental conditions and experimental results of Examples 157-159

| Example No. | EGFR inhibitor | Classification of Inhibitor | Dosage | Frequency | Modelling time | Administration | Concentration | Administration side | Relief Rate |
|---|---|---|---|---|---|---|---|---|---|
| 157 | Gefitinib | The first generation of small molecule EGFR inhibitor | 80 mg/kg | Once per day | 16 | Nitroglycerin ointment | 0.1% | Left | 55.56% |
| 158 | Erlotinib | The first generation of small molecule EGFR inhibitor | 70 mg/kg | Once per day | 10 | Nitroglycerin ointment | 0.1% | Left | 50% |
| 159 | Aftatinib | The second generation of small molecule EGFR inhibitor | 40 mg/kg | Once per day | 8 | Nitroglycerin ointment | 0.1% | Left | 33.33% |

It can be seen from the results in Table 15 that the nitric oxide releasing agent can effectively treat the hand-foot syndrome caused by the EGFR inhibitor.

Example 160

Determination of the Effect of the Nitric Oxide Releasing Agent on Treatment of EGFR Inhibitors BALB/C nude mice (Lung cancer cell A549 xenografts) model was constructed. After the model was stabilized, the model mice were divided into 4 groups (the average tumor size of the 4 groups of mice was as consistent as possible), except for the blank group (5 mice), other groups (10 mice in each group) were taken for experiments giving intragastric administration of medicaments and topical administration of medicaments.

The EGFR inhibitor was dissolved in a mixed solution of Cremophor EL:ethanol=1:1 (volume ratio), and the volume was adjusted to the required concentration (diluted about 3 times with PBS solution) before gavage, and the gavage amount did not exceed 0.2 mL. The medicament was administered by intragastric administration for 5 days per week, and the dose was gradually increased. Except the blank group, the other three groups of tumor-bearing mice took afatinib orally to control or shrink the tumor. At the same time, by transdermal administration, a medicament for preventing or treating epithelial tissue diseases caused by inhibition of EGFR is applied to the back of the mouse, and the specific implementation is as follows:

A) blank group: 5 tumor-bearing mice, no intragastric administration and no topical administration; B) blank substrate ointment group: 10 mice with tumor, oral administration of Afatinib (10 mg/kg in the first week, 15 mg/kg in the second week, 20 mg/kg in the third week), topical administration of a blank ointment on the back (administer once per day for 21 days); C) 0.1% nitroglycerin group: 10 mice with tumor, oral administration of afatinib, 0.1% nitroglycerin ointment (the same administration method and frequency as group B); D) 0.2% nitroglycerin group: 10 mice with tumor, oral administration of afatinib, 0.2% nitroglycerin ointment (the same administration method and frequency as group B); mark a topical administered area with an area of about 5.8 cm$^2$, which can not be reached by the mouth of the mice nor close to the tumor region. In the B, C, and D experimental groups, after the daily gavage, the corresponding ointment was administered with a cotton swab in the marked area on the back of the model mice, and administered evenly to ensure the skin is moisturized; after the administraation, each mouse was stabilized in a relatively independent space for 4 hours to ensure transdermal absorption of the medicament on the back; after 4 hours, the residual ointment on the back of the mouse was gently wiped off with a paper towel or a wet paper towel; then the mice can return to the cage where they were previously raised and could moved freely. The size of the tumor was measured and recorded every 2 days. After 21 days of the experiment, the mice were dissected, the tumors were removed, weighed and recorded, and the changes in tumor volume of different experimental groups were observed.

Figure 16:
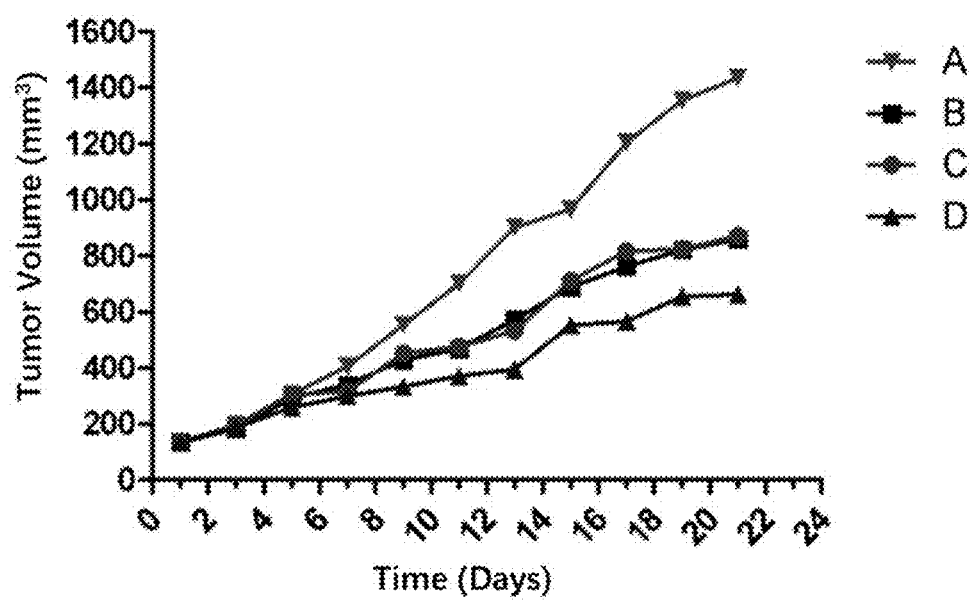
FIG. 16 indicates the effect of the nitric oxide releasing agent of the present application on the therapeutic effect of an EGFR inhibitor.

Results can be seen in FIG. 16. It is shown in the results that the volume of tumor tissue in group B, C, and D (afatinib administered by gavage) was significantly smaller than that in group A (afatinib unadministered group); the tumor volume of nitroglycerin ointment group (Group C and D) was close to or slightly smaller than the blank ointment group (Group B). It can be seen that the transdermal ointment of nitric oxide releasing agent does not affect the therapeutic effect of EGFR inhibitors on tumors.

All references as cited herein, including publications, patent applications and patents, are hereby incorporated by reference, as if it is individually and in particular stated that each of the references is incorporated by reference and to the extent that the reference is completely set forth herein.

In the context of the present application (especially in the context of the following claims, unless otherwise stated herein or clearly contradictory to the context, the terms "a" and "an" and "the" and "at least a/an/one" and similar referents are to be understood as comprising both singular and plural forms. Unless otherwise stated herein or clearly contradictory to the context, when the term "at least one" is followed by one or more of items as listed (for example, "at least one of A and B"), it is to be understood as one of the listed items (A or B) or any combination of two or more of the listed items (A and B). Unless otherwise noted, the terms "comprise," "have," "include," and "contain," are intended to mean an open term (i.e., meaning "including, but not limited to"). Unless otherwise defined in the context, recitation of ranges of values as used herein are merely intended to serve as a shorthand of a plural of each individual value falling within the range as individually listed, and each individual value is incorporated in the specification as if it is individually listed herein. Unless otherwise stated herein or clearly contradictory to the context, all the methods as described herein can be performed in any suitable order. Unless otherwise defined in the claims, any and all examples or exemplary languages (e.g., "such as") as used herein are merely intended to illustrative, and not to limit the scope of the application. Any language in the specification should not be construed as indicating that any element which is not claimed in the claims is necessary to practice the application.

Preferred embodiments of the present application are described herein, including the mode known by the inventors for carrying out the application. Upon reading of the description, variations of those preferred embodiments will be apparent to those of ordinary skill in the art. The inventors expect that the skilled person can apply such variants if required, and the inventors intend to implement the present application in a manner other than those specifically described herein. Thus, the present application includes all the modifications and equivalents of the subject matter described in the appended claims as permitted by applicable laws. Moreover, the present application comprises any combination of all possible variations of the aforesaid elements, unless otherwise indicated or clearly contradict with the context.

The invention claimed is:

1. A method for treating EGFR-inhibition associated rash in a subject, comprising administering to the subject a medicament comprising an effective amount of a nitric oxide releasing agent.

2. The method of claim 1, wherein the nitric oxide releasing agent is isosorbide dinitrate or isosorbide mononitrate.

3. The method of claim 2, wherein the medicament is administered topically.

4. The method of claim 3, wherein the medicament is an ointment, lotion, gel, or cream.

5. The method of claim 3, wherein the concentration of the nitric oxide releasing agent in the medicament is from about 0.05% (w/w) to about 5.0% (w/w).

6. The method of claim 3, wherein the nitric oxide releasing agent is isosorbide dinitrate.

7. The method of claim 3, wherein the nitric oxide releasing agent is isosorbide mononitrate.

8. The method of claim 3, wherein the medicament comprises isosorbide dinitrate and isosorbide mononitrate.

9. The method of claim 5, wherein the subject is a cancer patient.

10. The method of claim 9, wherein the subject has been or is being administered an EGFR inhibitor.

11. A method for treating an EGFR-inhibition associated epithelial disease in a subject, which comprises administering to the subject an effective amount of a nitric oxide releasing agent for treating the disease.

12. The method of claim 11, wherein the EGFR inhibition is caused by administration of an EGFR inhibitor.

13. The method of claim 12, wherein the EGFR inhibitor is or comprises: Cetuximab, Gefitinib, Erlotinib, Icotinib, Sapitinib, Afatinib, Lapatinib, Vandetanib, Neratinib, Brigatinib, Panitumumab, Necitumumab, Nimotuzumab, Tesevatinib, Allitinib, Theliatinib, Rociletinib, Canertinib, AZD3759, YZJ-0318, Neptinib, Naquotinib, PF-06747775, SPH1188-11, Poziotinib, Epitinib, Varlitinib, Alflutinib, HM61713, CK-101, Pyrotinib, Larotinib, HS-10296, AP32788, Simotinib, GMA204, Virlitinib, Yinlitinib, Nazartinib, Rociletinib, Olmutinib, Osimertinib, Dacomitinib, Avitinib or EAI045.

14. The method of claim 11, wherein said epithelial disease comprises EGFR-inhibition associated rash, EGFR-inhibition associated acne, EGFR-inhibition associated skin pruritus, EGFR-inhibition associated hand-foot syndrome, EGFR-inhibition associated alopecia, EGFR-inhibition associated hair changes, EGFR-inhibition associated erythema, EGFR-inhibition associated skin exfoliation, EGFR-inhibition associated herpes, EGFR-inhibition associated hirsutism, EGFR-inhibition associated hyperpigmentation, EGFR-inhibition associated nail disorders, EGFR-inhibition associated paronychia and schizonychia, EGFR-inhibition associated xerosis cuits, EGFR-inhibition associated hypersensitivity, EGFR-inhibition associated mucositis, EGFR-inhibition associated nasopharyngitis, EGFR-inhibition associated epistaxis, EGFR-inhibition associated xerostomia, EGFR-inhibition associated cheilitis, EGFR-inhibition associated mouth ulcer and/or EGFR-inhibition associated gastrointestinal mucosal injury.

15. The method of claim 11, wherein said epithelial disease comprises EGFR-inhibition associated rash.

16. The method of claim 14, wherein the severity grading of the epithelial disease is Grade 1 or above, Grade 2 or above, Grade 3 or above, Grade 4 or above, or Grade 5, as evaluated in accordance with NCI-CTCAE V5.0.

17. The method of claim 11, wherein said nitric oxide releasing agent is nitroglycerin, isosorbide mononitrate, or isosorbide dinitrate.

18. The method of claim 11, wherein said nitric oxide releasing agent is administered topically.

19. The method of claim 18, wherein said nitric oxide releasing agent is topically administered at a site that is not the occurrence site of cancer or potential metastatic site of cancer.

20. The method of claim 18, wherein said nitric oxide releasing agent is formulated into an ointment, lotion, gel, or cream.

21. The method of claim 20, wherein the subject is a cancer patient.

22. The method of claim 21, wherein the cancer patient has been or is being administered with an EGFR inhibitor.

* * * * *